United States Patent
Yu et al.

(10) Patent No.: US 10,802,014 B2
(45) Date of Patent: *Oct. 13, 2020

(54) APPARATUS FOR IMPROVED DISEASE DETECTION

(71) Applicant: AnPac Bio-Medical Science (Shanghai) Co., Ltd., Shanghai (CN)

(72) Inventors: Chris C. Yu, Conneautville, PA (US); Xuedong Du, Shanghai (CN)

(73) Assignee: AnPac Bio-Medical Science (Shanghai) Co., Ltd., Shanghai (CN)

( * ) Notice: Subject to any disclaimer, the term of this patent is extended or adjusted under 35 U.S.C. 154(b) by 81 days.

This patent is subject to a terminal disclaimer.

(21) Appl. No.: 14/759,364

(22) PCT Filed: Jan. 7, 2014

(86) PCT No.: PCT/CN2014/070219
§ 371 (c)(1),
(2) Date: Jul. 6, 2015

(87) PCT Pub. No.: WO2014/106493
PCT Pub. Date: Jul. 10, 2014

(65) Prior Publication Data
US 2015/0369798 A1    Dec. 24, 2015

Related U.S. Application Data

(60) Provisional application No. 61/749,661, filed on Jan. 7, 2013.

(51) Int. Cl.
*G01N 33/50*    (2006.01)
*B01L 3/00*    (2006.01)

(52) U.S. Cl.
CPC .... *G01N 33/5091* (2013.01); *B01L 3/502761* (2013.01); *B01L 2200/0652* (2013.01); *B01L 2300/0645* (2013.01); *B01L 2300/0816* (2013.01); *B01L 2300/0864* (2013.01); *B01L 2300/0887* (2013.01)

(58) Field of Classification Search
CPC ....... B01L 3/502761; B01L 2200/0647; B01L 2200/0636; B01L 2200/0652; B01L 2300/0636; B01L 2300/0887; B01L 3/502707; B01L 2300/0627; B01L 2300/0877; B01L 2300/163; B01L 3/502715; B01L 7/52
See application file for complete search history.

(56) References Cited

U.S. PATENT DOCUMENTS

2008/0302732 A1* 12/2008 Soh .................. B01L 3/502761
                                                                  210/695
2014/0017670 A1*  1/2014 Yu ......................... G01N 35/08
                                                                     435/5

* cited by examiner

*Primary Examiner* — Sally A Merkling
(74) *Attorney, Agent, or Firm* — Weisun Rao; Jun Chen; Venture Partner, LLC

(57) ABSTRACT

An apparatus for detecting a disease in a biological subject comprises a delivery system and at least two sub-equipment units which are combined or integrated in the apparatus, wherein the delivery system is capable of delivering the biological subject to at least one of the sub-equipment units and each sub-equipment unit is capable of detecting at least one property of the biological subject. Methods for detecting a disease with the apparatus are also provided.

46 Claims, 47 Drawing Sheets

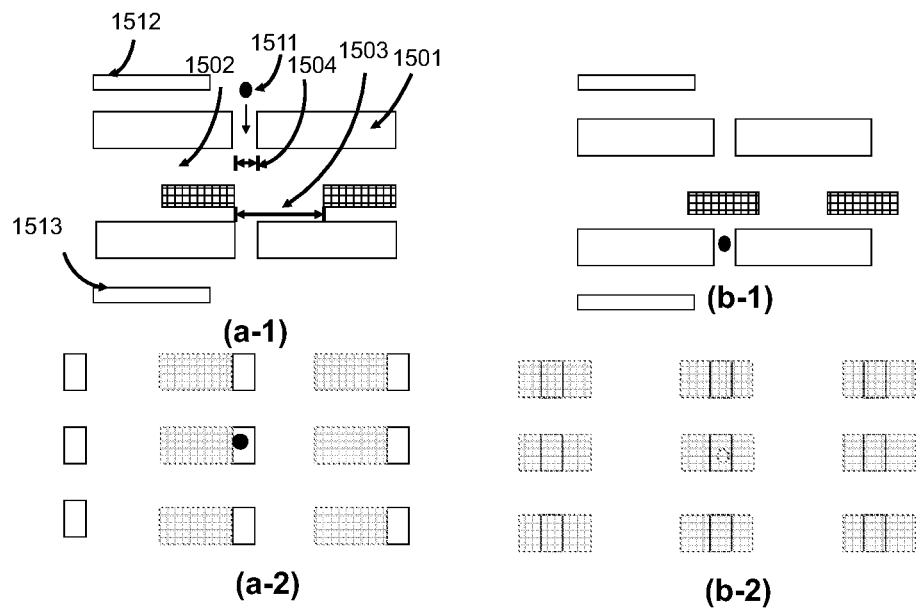
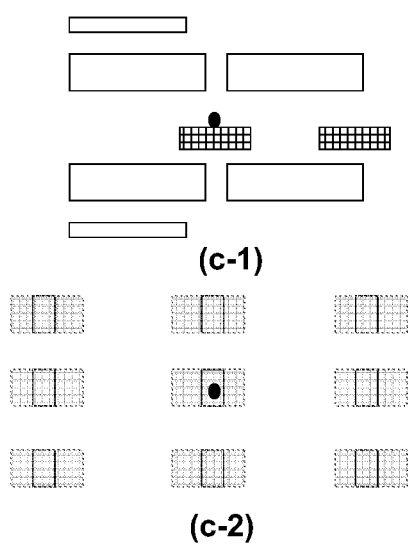
FIGURE 15
FIGURE 15 (Cont.)

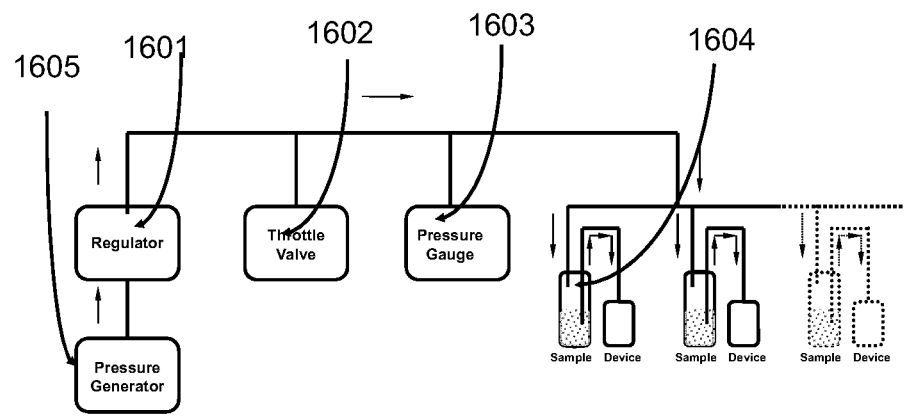
FIGURE 16
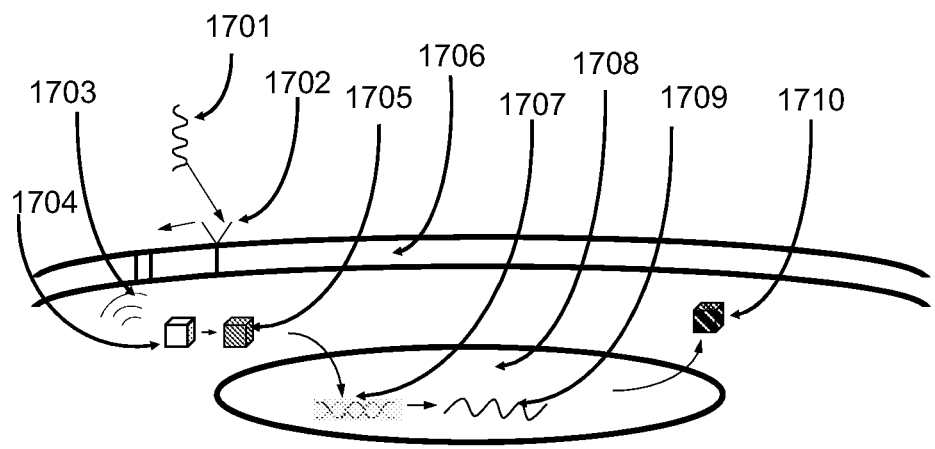
FIGURE 17-a

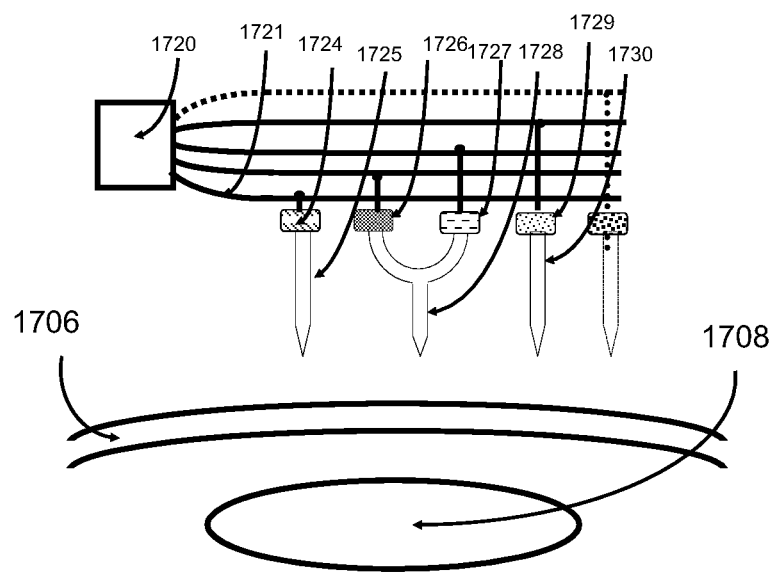
FIGURE 17-b
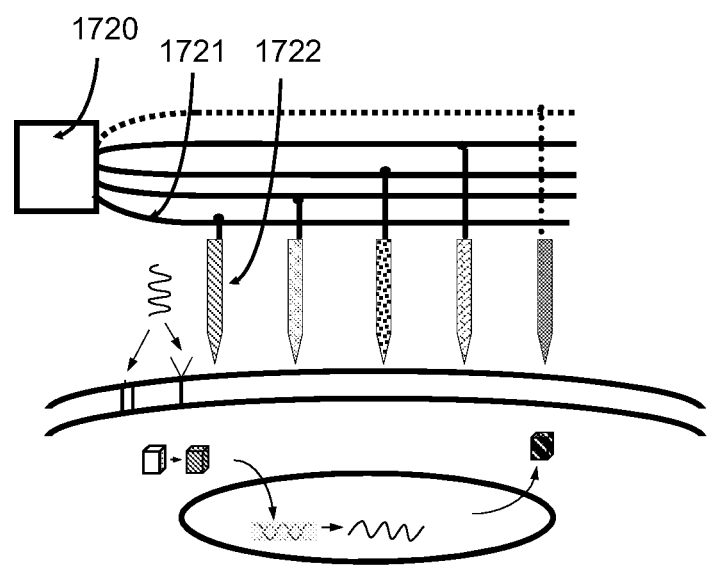
FIGURE 17-c

**Detecting device covered with
transparent panel**

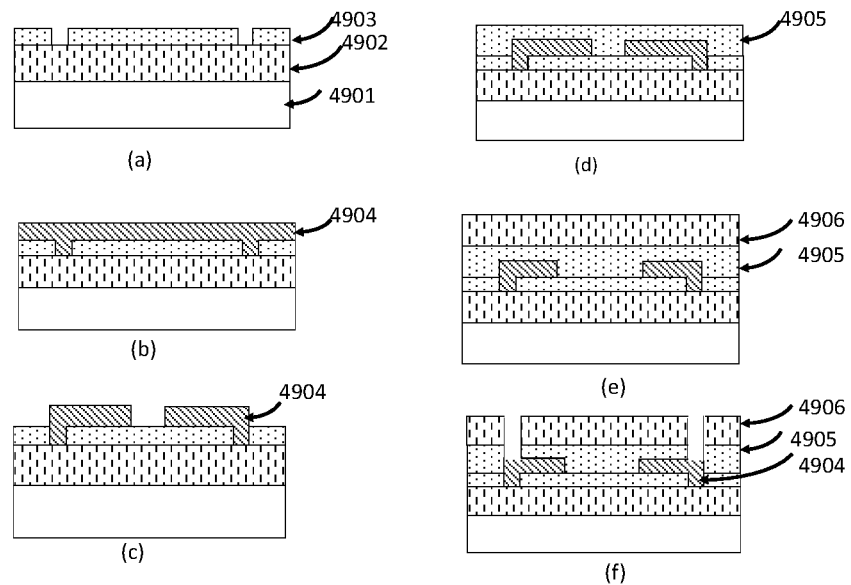
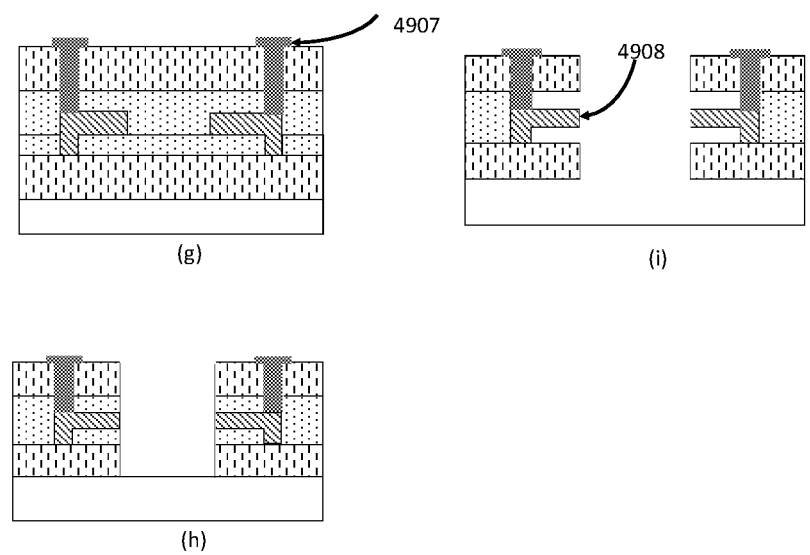
FIGURE 49

(k)

(l)

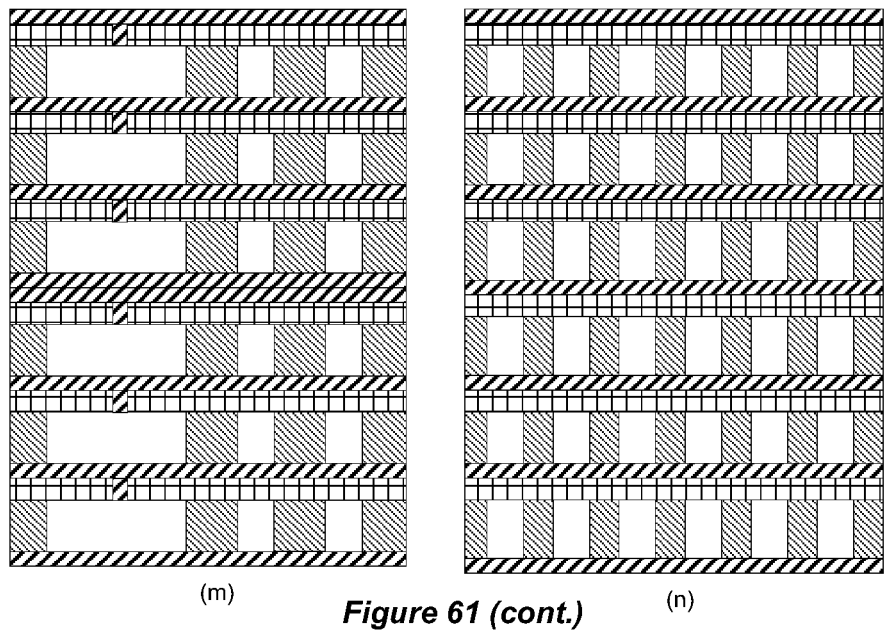
(m)  Figure 61 (cont.)  (n)
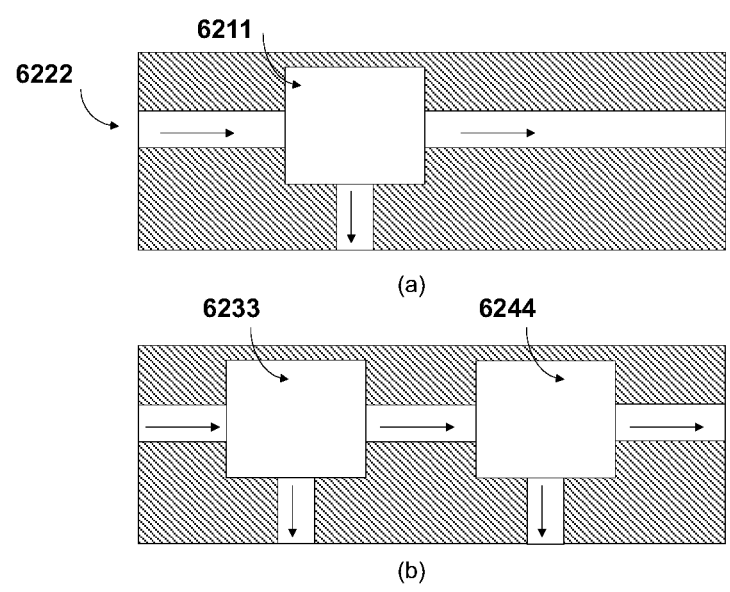
Figure 62

APPARATUS FOR IMPROVED DISEASE DETECTION

CROSS-REFERENCE TO RELATED APPLICATION

This application is a U.S. national phase application of international application No. PCT/CN2014/070219, filed on Jan. 7, 2014, which claims priority to U.S. Application No. 61/749,661, filed on Jan. 7, 2013, the contents of which are incorporated herein by reference in their entireties.

BACKGROUND OF THE INVENTION

Many diseases are difficult to be detected by a single approach or methodology. In particular, many serious diseases with high morbidity and mortality, including cancer and heart diseases, are difficult to diagnose at an early stage with high sensitively, specificity and efficiency, by using one detection equipment. Current disease diagnosis devices typically detect and rely on a single type of macroscopic data and information such as body temperature, blood pressure, or scanned images of the body. For example, to detect serious diseases such as cancer, each of the diagnosis apparatus commonly used today is based on one imaging technology, such as x-ray, CT scan, or nuclear magnetic resonance (NMR). While used in combination, these diagnosis apparatus provide various degrees of usefulness in disease diagnosis. However, each of them alone cannot provide accurate, conclusive, efficient, and cost-effective diagnosis of such serious diseases as cancer at an early stage. Further, many of the existing diagnosis apparatus have a large size and are invasive with large footprint, such as x-ray, CT scan, or nuclear magnetic resonance (NMR).

Even the newly emerged technologies such as those deployed in DNA tests usually rely on a single diagnosis technology and cannot provide a comprehensive, reliable, accurate, conclusive, and cost-effective detection for a serious disease. In recent years, there have been some efforts in using nano technologies for various biological applications, with most of the work focused on one type of gene mapping and moderate developments in the field of disease detection. For instance, Pantel et al. discussed the use of a MicroElectroMechanical Systems (MEMS) sensor for detecting cancer cells in blood and bone marrow in vitro (see, e.g., Klaus Pantel et al., *Nature Reviews*, 2008, 8, 329); Kubena et al. disclose in U.S. Pat. No. 6,922,118 the deployment of MEMS for detecting biological agents; and Weissman et al. disclose in U.S. Pat. No. 6,330,885 utilizing MEMS sensor for detecting accretion of biological matter.

In sum, to date, most of above described technologies have been limited to isolated diagnosis technology for sensing, using systems of relatively simple constructions and large dimensions but often with limited functions, and lack sensitivities and specificities. Further, the existing technologies require multiple times detection by multiple apparatus. This will increase costs and affect achieved degree of sensitivity and specificity as well.

These drawbacks call for novel solutions that provide reliable and flexible diagnosis apparatus using multiple diverse technologies and bring improved accuracy, sensitivity, specificity, efficiency, non-invasiveness, practicality, conclusive, and speed in early-stage disease detection at reduced costs.

SUMMARY OF THE INVENTION

The present invention in general relates to a class of innovative and integrated apparatus for carrying out disease detection at microscopic levels, in vivo or in vitro, on a single cell, a single biological molecule (e.g., DNA, RNA, or protein), a single biological subject (e.g., a single virus), or other sufficiently small unit or fundamental biological composition. This class of apparatus can be made by using state-of-the-art micro-device fabrication technologies and novel process flows such as integrated circuit fabrication technologies. As used herein, the term "disease detection apparatus" can be interchanged with such terms as disease detection device or apparatus integrated with micro-devices, or any other similar terms of the same meaning. The apparatus of this invention contain a delivery system to delivery the biological subject to multiple sub-equipment units to perform different diagnosis functions and detect multiple parameters of a biological subject to be detected or analyzed. Optional components of the apparatus include means to perform at least the function of addressing, controlling, forcing, receiving, amplifying, manipulating, processing, analyzing, making decisions (e.g., logic decisions), or storing information from each probe. Such means can be, e.g., a central control unit that includes a controlling circuitry, an addressing unit, an amplifier circuitry, a logic processing circuitry, an analog device, a memory unit, an application specific chip, a signal transmitter, a signal receiver, or a sensor. Optional components of the apparatus also include means for reclaiming or treatment medical waste from each sub-equipment unit.

These disease detection apparatus are capable of using or combing multiple diagnosis technologies and sub-equipment units in one apparatus to detect diseases at their early stages with a higher and much improved degree of sensitivity, specificity, speed, simplicity, practicality, convenience (e.g., simpler operating procedures or reduced apparatus size), reduced apparatus volume, or affordability (e.g., reduced costs), with substantially reduced or even no invasiveness and side effects. Accordingly, the apparatus of this invention are capable of performing at a much higher level than those of conventional disease detection apparatus or technologies.

Examples of inventive fabrication techniques or processes that can be used to make the apparatus of this invention include, but are not limited to, mechanical, chemical, physical-chemical, chemical mechanical, electrical, physical, biochemical, bio-physical, bio-physical mechanical, electro-mechanical, electro-optical, bio-electro-optical, bio-thermal optical, electro-chemical optical, bio-electro-mechanical, micro-electro-mechanical, electro-chemical-mechanical, electro-bio-chemical-mechanical, nano-fabrication techniques, integrated circuit and semiconductor manufacturing techniques and processes. For a general description of some of the applicable fabrication technologies, see, e.g., R. Zaouk et al., *Introduction to Microfabrication Techniques*, in Microfluidic Techniques (S. Minteer, ed.), 2006, Humana Press; *Microsystem Engineering of Lab-on-a-chip Devices*, 1st Ed. (Geschke, Klank & Telleman, eds.), John Wiley & Sons, 2004. Micro-device functionalities would at least include sensing, detecting, measuring, diagnosing, monitoring, and analyzing for disease diagnosis. Multiple sub-equipment units or micro-devices can be integrated onto a piece of detection apparatus to make the apparatus more advanced and sophisticated for further enhanced measurement sensitivity, specificity, speed and functionalities, with ability to measure the same parameter or a set of different parameters.

Specifically, one aspect of this invention provides apparatus for detecting a disease in a biological subject with improved accuracy, sensitivity, specificity, efficiency, non-invasiveness, practicality, simplicity, or speed, at reduced costs and tool size. Each apparatus includes: a delivery system and at least two sub-equipment units, wherein the delivery system is capable of delivering the biological subject to one or more of the desired sub-equipment units, and each sub-equipment unit is capable of detecting at least a property of the biological subject. By integrating multiple sub-equipment units, various micro-devices are integrated into one piece of the apparatus of this invention.

In some embodiments, at least one of the sub-equipment units comprises a first layer of material having an exterior surface and an interior surface, wherein the interior surface defines an inter-unit channel in which the biological subject flows through the sub-equipment unit. In some other embodiments, at least one of the sub-equipment units further comprises a first sorting unit capable of detecting a property of the biological subject at the microscopic level and sorting the biological subject by the detected property; a first detection unit capable of detecting the same or different property of the sorted biological subject at the microscopic level; wherein the first sorting unit and the first detection unit are integrated into the first layer of material and positioned to be at least partially exposed in the inter-unit channel.

In some embodiments, the sub-equipment unit further comprises a second sorting unit, wherein the biological subject flows by the first sorting unit before reaching the second sorting unit, and the second sorting unit is capable of detecting the same or different property of the biological subject as the first sorting unit and further sorting the biological subject by the property it detects. Alternatively, the sub-equipment unit may further include a second detection unit, wherein the biological subject flows by the first detection unit before reaching the second detection unit, and the second detection unit is capable of detecting the same or different property of the biological subject as the first detection unit. Optionally, a portion of the biological subject from the exit of sorting unit, which is a likely suspect of diseased biological subject, continues to flow to the detection unit, while the rest of the biological subject is directed to another direction for separate disposal (e.g., being dispelled to a system for reclaiming or treatment of waste or for other types of tests).

In some embodiments, the biological subject that flows out of the detection unit is transported back to the sorting unit for further sorting and detection of a same or different property at the microscopic level. This process can be repeated to further concentrate the number of suspected, diseased biological entity (e.g., to increase the number of the diseased biological entities to be detected per unit volume).

In some embodiments, each property to be detected by a sub-equipment unit, or specifically by its sorting unit or a detection unit, is independently a thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, electrical, magnetic, electromagnetic, physical or mechanical property, or a combination thereof. For example, the thermal property can be temperature or vibrational frequency; the optical property can be optical absorption, optical transmission, optical reflection, optical-electrical property, brightness, or fluorescent emission; the chemical property can be pH value, chemical reaction, bio-chemical reaction, bio-electro-chemical reaction, reaction speed, reaction energy, speed of reaction, oxygen concentration, oxygen consumption rate, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property can be density, shape, volume, or surface area; the electrical property can be surface charge, surface potential, resting potential, electrical current, electrical field distribution, electrical dipole, electrical quadruple, three-dimensional electrical or charge cloud distribution, electrical properties at telomere of DNA and chromosome, capacitance, impedance, change in surface charge, change in surface potential, change in resting potential, change in electrical current, change in electrical field distribution, change in electrical dipole, change in electrical quadruple, change in three-dimensional electrical or charge cloud distribution, change in electrical properties at telomere of DNA and chromosome, change in capacitance, or change in impedance; the biological property can be surface shape, surface area, surface charge, surface biological property, surface chemical property, pH, electrolyte, ionic strength, resistivity, cell concentration, or biological, electrical, physical or chemical property of solution; the acoustic property can be frequency, speed of acoustic waves, acoustic frequency and intensity spectrum distribution, acoustic intensity, acoustical absorption, or acoustical resonance; the mechanical property can be internal pressure, hardness, flow rate, viscosity, shear strength, elongation strength, fracture stress, adhesion, mechanical resonance frequency, elasticity, plasticity, or compressibility. The properties to be detected by any two of the sub-equipment units can be same or different. In some embodiments, one of the sub-equipment units uses a property detected by another sub-equipment unit to detect the same or different property of the biological subject.

In some embodiments, the sub-equipment unit, or optionally each of its sorting unit and the detection unit, comprises one or more sensors positioned to be partially in the channel and capable of detecting a property of the biological subject at the microscopic level, wherein the property to be detected by the sensors in the sorting unit and the detection unit can be the same or different. In some embodiments, one of the sensors is positioned in the interior surface defining the channel and capable of detecting the same or different property as another sensor. For example, the sorting unit or the detection unit may further comprise at least three additional sensors each of which is positioned in the same interior surface defining the channel and detects the same or different property as the first sensor. These sensors can be arranged in one group or at least two groups.

In some embodiments, at least one of the sensors, the sub-equipment unit, the sorting units and the detection units is fabricated by microelectronics technologies. For instance, the sensors can be fabricated to be integral part of the interior surface that defines the first inter-unit channel, or the sensors can be fabricated separately from and then bonded to the interior surface that defines the first inter-unit channel.

In some embodiments, at least one of the sensors is positioned through the exterior and interior surfaces of the first layer of material and exposed in the inter-unit channel defined by the interior surface and the space outside the exterior surface In some embodiments, the first sensor is connected to a circuitry outside the exterior surface.

In some embodiments, the sorting unit or the detection unit further comprises a read-out circuitry which is connected to the first sensor and transfers data from the first sensor to a recording device. The connection between the read-out circuit and the first sensor can be digital, analog, optical, thermal, piezo-electrical, piezo-photronic, piezo-electrical photronic, opto-electrical, electro-thermal, opto-thermal, electrical, electromagnetic, electromechanical, or mechanical.

In some embodiments, each sensor is independently a thermal sensor, optical sensor, acoustical sensor, biological sensor, chemical sensor, electro-mechanical sensor, electro-chemical sensor, electro-optical sensor, electro-thermal sensor, electro-chemical-mechanical sensor, bio-chemical sensor, bio-mechanical sensor, bio-optical sensor, bio-thermal sensor, bio-physical sensor, bio-electro-mechanical sensor, bio-electro-chemical sensor, bio-electro-optical sensor, bio-electro-thermal sensor, bio-mechanical-optical sensor, bio-mechanical thermal sensor, bio-thermal-optical sensor, bio-electro-chemical-optical sensor, bio-electro-mechanical optical sensor, bio-electro-thermal-optical sensor, bio-electro-chemical-mechanical sensor, electrical sensor, magnetic sensor, electro-magnetic sensor, physical sensor, mechanical sensor, piezo-electrical sensor, piezo-electro photronic sensor, piezo-photronic sensor, piezo-electro optical sensor, bio-electrical sensor, bio-marker sensor, image sensor, or radiation sensor. For example, the thermal sensor can comprise a resistive temperature micro-sensor, a micro-thermo-couple, a thermo-diode and thermo-transistor, and a surface acoustic wave (SAW) temperature sensor; electrical sensor, magnetic sensor, electromagnetic sensor, the image sensor comprises a charge coupled device (CCD) or a CMOS image sensor (CIS); the radiation sensor can comprise a photoconductive device, a photovoltaic device, a gyro-electrical device, or a micro-antenna; the mechanical sensor can comprise a pressure micro-sensor, micro-accelerometer, flow meter, viscosity measurement tool, micro-gyrometer, or micro flow-sensor; the magnetic sensor can comprise a magneto-galvanic micro-sensor, a magneto-resistive sensor, a magneto diode, or magneto-transistor; the biochemical sensor can comprise a conductimetric device or a potentiometric device.

In some embodiments, at least one sensor is a probing sensor and can apply a probing or disturbing signal to the biological subject to be tested. Optionally, at least one sensor (i.e., not the just-mentioned probing sensor) or another sensor (along with the just-mentioned probing sensor) is a detection sensor and detects a response from the biological subject upon which the probing or disturbing signal is applied.

In some embodiments, the one or more sensors are fabricated on the interior surface of the layer of material. For example, at least two sensors can be fabricated on the interior surface of the layer of material and are arranged in an array.

In some embodiments, the channel defined by the interior surface has a symmetric configuration, e.g., an oval, circular, triangular, square, or rectangular configuration. In some particular embodiments, the channel has a rectangular configuration and 4 sides of walls.

In some embodiments, the channel has a length ranging from 1 micron to 50,000 microns.

In some embodiments, at least two sensors are located on one side or two opposite sides of the interior surface defining the channel. For example, at least four sensors can be located on one side, two opposite sides, or four sides of the interior surface defining the channel.

In some embodiments, the sorting unit or the detection unit comprise two panels, at least one of the two panels is fabricated by microelectronic technologies and comprises a read-out circuitry and a sense, and the sensor is positioned on the interior surface which defines the channel.

In some embodiments, the sorting unit or the detection unit further comprises two micro-cylinders that are placed between and bonded with the two panels, wherein each of the micro-cylinders is solid, hollow, or porous, and optionally fabricated by microelectronics technologies.

In some embodiments, the micro-cylinders are solid and at least one of them comprises a sensor fabricated by microelectronics technologies. The sensor in the micro-cylinder can detect the same or different property as a sensor in the panel does.

In some embodiments, the sensor in the micro-cylinder applies a probing signal to the biological subject.

In some embodiments, at least one of the micro-cylinders comprises at least two sensors fabricated by microelectronics technologies, and every two of the at least two sensors are so located in the micro-cylinder to form an array of the sensors on the panel.

In some embodiments, the two sensors in the micro-cylinder are apart by a distance ranging from 0.1 micron to 500 microns, from 0.1 micron to 50 microns, form 1 micron to 100 microns, from 2.5 microns to 100 microns, or from 5 microns to 250 microns.

In some embodiments, at least one of the panels comprises at least two sensors that are arranged in at least two arrays each separated by at least a micro sensor in a cylinder.

In some embodiments, at least one array of the sensors in the panel comprises two or more sensors.

In some embodiments, the sorting unit or the detection unit further comprises an application specific integrated circuit chip which is internally bonded to or integrated into one of the panels or a micro-cylinder.

In some embodiments, the sub-equipment unit or the sorting unit or the detection unit further comprises an optical device, imaging device, camera, viewing station, acoustic detector, piezo-electrical detector, piezo-photronic detector, piezo-electro photronic detector, electro-optical detector, electro-thermal detector, electrical detector, bio-electrical detector, bio-marker detector, bio-chemical detector, chemical sensor, thermal detector, ion emission detector, photo-detector, x-ray detector, radiation material detector, or thermal recorder, each of which is integrated into the a panel or a micro cylinder.

In some embodiments, the interior surface defines at least one additional inter-unit channel for transporting and sorting or detecting the biological subject.

In some embodiments, the interior surface defines at least one additional inter-unit channel for transporting away a portion of the biological subject that is an unlikely suspect of being diseased based on the sorting and/or detection.

In some embodiments, the interior surface defines at least one additional inter-unit channel for transporting the biological subjects suspected of disease based on the sorting and/or detection for further sorting and/or detection. The further sorting and/or detection may include, e.g., transporting such a suspected biological subject back to the sorting unit and/or detection unit where it has been processed for further concentration (i.e., increasing the number of diseased biological subject, or the number of diseased biological entities in the biological subject, per unit volume).

In some embodiments, any or each sub-equipment unit has numerous (e.g., from a few to hundreds or millions) channels for transporting and sorting or detecting the biological subject.

In some embodiments, the inter-unit channel has a diameter or height or width ranging from 0.1 micron to 150 microns, from 0.5 micron to 5 microns, from 1 micron to 2.5 microns, from 3 microns to 15 microns, from 5 microns to 25 microns, from 5 microns to 50 microns, from 25 microns to 50 microns, or from 50 microns to 80 microns; and the channel has a length ranging from 0.5 micron to 50,000 microns.

In some embodiments, the sub-equipment unit or the sorting unit or the detection unit comprises and is capable of releasing a bio-marker, a nano-particle, a magnetic particle, an enzyme, a protein, a light emitting component, an radio-active material, a dye, a polymer component, an organic component, a catalyst, an oxidant, a reducing agent, an ionic component, or a nano-particle attached to a bio-marker, or a combination thereof, for mixing with and sorting or detecting the biological subject.

In some embodiments, the nano-particle attached to a bio-marker is a magnetic nano-particle; and one or more magnetic nano-particles are mixed with the biological subject for separating and detecting the biological subject. For example, the bio-marker can be attached with a light emitting item and mixed with the biological subject. The light emitting item can be a florescence generating component.

In some embodiments, the mixed biological subject flows through a inter-unit channel; a signal of the mixed biological subject is detected and collected by a sensor in a sorting or detection unit; and the signal is a thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, electrical, magnetic, electromagnetic, physical or mechanical signal, or a combination thereof.

In some embodiments, the biological subject flows through the first inter-unit channel and, after the sorting unit, is separated into a suspected component and an unsuspected component, and the two components continue to flow through the inter-unit channel in two different directions.

In some embodiments, each sub-equipment unit further comprises one or more additional inter-unit channels each of which is defined by the interior surface of the first or additional layer of material and is integrated to the first channel, and the separated suspected component or unsuspected component flows through the additional channel(s) for further separation.

In some embodiments, any or each of the sub-equipment units further comprises multiple additional channels, each of the additional channels is defined by the interior surface of the first layer of material or additional layer(s) of material, is directly or indirectly integrated to the first channel and other channel(s), and optionally comprises a sorting unit or a detection unit attached to the interior surface defining the channel; and the biological subject flows through these multiple channels simultaneously and are sorted and separated therein.

In some embodiments, the first inter-unit channel is centrally positioned in the sub-equipment unit as compared to the other additional inter-unit channels and is connected to at least two other inter-unit channels; and a designed component injected into the first inter-unit channel flows from this first inter-unit channel to the other connected inter-unit channels.

In some embodiments, the designed component is a bio-marker, a nano-particle, a magnetic particle, an enzyme, a protein, a light emitting component, an radio-active material, a dye, a polymer component, an organic component, a catalyst, an oxidant, a reducing agent, an ionic component, or a nano-particle attached to a bio-marker, a disturbing fluid, or a combination thereof.

In some embodiments, the amount, timing or speed of the designed component injected into the first channel is pre-programmed or controlled in real time.

In some embodiments, the apparatus of this invention further comprises a probing unit which is capable of applying a probing or disturbing signal to the biological subject or a media in which the biological subject is contained, thereby changing the nature or value of a property of the biological subject or of the media.

In some embodiments, the probing signal can be of the same or different type as the property to be detected and can change the value of the property to be detected. The probing signal or the property to be detected can be independently a thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, electrical, magnetic, electromagnetic, physical or mechanical property, or a combination thereof. The thermal property can be temperature or vibrational frequency; the optical property can be optical absorption, optical transmission, optical reflection, optical-electrical property, brightness, or fluorescent emission; the chemical property can be pH value, chemical reaction, bio-chemical reaction, bio-electro-chemical reaction, reaction speed, reaction energy, speed of reaction, oxygen concentration, oxygen consumption rate, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property can be density, shape, volume, or surface area; the electrical property can be surface charge, surface potential, resting potential, electrical current, electrical field distribution, electrical dipole, electrical quadruple, three-dimensional electrical or charge cloud distribution, electrical properties at telomere of DNA and chromosome, capacitance, impedance, or a change therein; the biological property can be surface shape, surface area, surface charge, surface biological property, surface chemical property, pH, electrolyte, ionic strength, resistivity, cell concentration, or biological, electrical, physical or chemical property of solution; the acoustic property can be frequency, speed of acoustic waves, acoustic frequency and intensity spectrum distribution, acoustic intensity, acoustical absorption, or acoustical resonance; the mechanical property can be internal pressure, hardness, flow rate, viscosity, shear strength, elongation strength, fracture stress, adhesion, mechanical resonance frequency, elasticity, plasticity, or compressibility.

In some embodiments, the probing signal is changed from a static value to a dynamic value or to a pulsed value, or from a lower value to a higher value.

In some embodiments, at least one of the properties of the media is changed from a static value to a dynamic value or to a pulsed value, or from a lower value to a higher value.

In some embodiments, the probing signal or a property of the media is a thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, electrical, magnetic, electromagnetic, physical or mechanical property, or a combination thereof. For example, the probing signal or a property of the media can be laser intensity, temperature, catalyst concentration, acoustic energy, bio-maker concentration, electrical voltage, electrical current, fluorescent dye concentration, the amount of agitation of the biological sample, or fluid flow rate.

In some embodiments, the sub-equipment unit further comprises a pre-screening unit which is capable of pre-screening a diseased biological subject from a non-diseased biological subject based on the difference in a property between a diseased biological subject and a non-diseased biological subject.

In some embodiments, the disease to be detected is a cancer. Examples of the cancer include breast cancer, lung cancer, esophageal cancer, intestine cancer, cancer related to blood (e.g., leukemia), liver cancer, and stomach cancer. Yet, additional examples include circulating tumor cells (CTCs) which are very important and can occur in late stage cancer patients (sometime, they occur after cancer treatment related surgeries).

In some embodiments, the delivery system comprises a second layer of material having an interior surface, wherein the interior surface defines an intra-unit channel in which the biological subject flows to the inter-unit channel of one or more desired sub-equipment units.

The material defines an intra-unit channel and the material defines an inter-channel channel can be same or different.

Any section of the intra-unit channels and the inter-unit channels can be same or different. In some embodiment, the intra-unit channel has a symmetric configuration, e.g., an oval, circular, triangular, square, or rectangular configuration. For example, the intra-unit channel has a rectangular configuration and 4 sides of walls.

In some embodiments, the intra-unit channel has a length ranging from 1 micron to 50,000 microns, from 1 micron to 15,000 micron, from 1 micron to 10,000 microns, from 1.5 microns to 5,000 microns, from 3 microns to 1,000 microns.

In some embodiments, the intra-unit channel has a width or height ranging from 0.5 micron to 100 microns; from 0.5 micron to 25 microns, from 1 micron to 15 microns, or from 1.2 microns to 10 microns.

In some embodiments, at least two sensors are located on one side or two opposite sides of the interior surface defining the intra-unit channel. For example, at least four sensors are located on one side, two opposite sides, or four sides of the interior surface defining the intra-unit channel.

In some embodiments, the delivery system further comprises at least one additional intra-unit channel and any of the additional intra-unit channels can be the same or different channel as the first intra-unit channel. In some embodiments, the delivery system comprises multiple intra-unit channels (e.g., hundreds to thousands), which are capable of transporting the biological subject to one or more desired sub-equipment units at the same or different time.

In some embodiments, the delivery system is a fluid delivery system including a pressure generator, a pressure regulator, a flow meter, a flow regulator, a throttle valve, a pressure gauge, and distributing kits. As examples of these embodiments, the pressure generator can include a motor piston system and a bin containing compressed gas; the pressure regulator (which can consist of multiple regulators) can down-regulate or up-regulate the pressure to a desired value; the pressure gauge feeds back the measured value to the throttle valve which then regulates the pressure to approach the target value.

The biological fluid to be delivered can be a sample of a biological entity to be detected for disease or something not necessarily to be detected for disease. In some embodiments, the fluid to be delivered is liquid (e.g., a blood sample, a urine sample, a saliva sample, a tear sample, a sweat sample, or a lymph sample). The pressure regulator can be a single pressure regulator or multiple pressure regulators which are placed in succession to either down-regulate or up-regulate the pressure to a desired level, particularly when the initial pressure is either too high or too low for a single regulator to adjust to the desired level or a level that is acceptable for an end device or target.

Optionally, the apparatus has one or more additional features and structures each capable of delivering a second liquid solution containing an enzyme, protein, oxidant, reducing agent, catalyst, radio-active component, optical emitting component, or ionic component; and the second liquid solution can be delivered and added to the biological subject sample to be measured before or during sorting of the biological subject sample, or before or during the measurement (detection) of the biological subject sample, thereby resulting in further enhanced measurement sensitivity.

In some embodiments, the apparatus of this invention further comprises a central control unit that is connected to each sub-equipment unit and the delivery system, and capable of controlling the biological subject matter to be transported to one or more desired sub-equipment units and reading and analyzing a detected data from each sub-equipment unit. The central control unit comprises a controlling circuitry, an addressing unit, an amplifier circuitry, a logic processing circuitry, an analog device, a memory unit, an application specific chip, a signal transmitter, a signal receiver, or a sensor. The sensor comprises a thermal sensor, a flow meter, an optical sensor, an acoustic detector, a current meter, a pH meter, a hardness measurement sensor, an imaging device, a camera, a piezo-electrical sensor, a piezo-photronic sensor, a piezo-electro photronic sensor, an electro-optical sensor, an electro-thermal sensor, a bio-electrical sensor, a bio-marker sensor, a bio-chemical sensor, a chemical sensor, an ion emission sensor, a photo-detector, an x-ray sensor, a radiation material sensor, an electrical sensor, a magnetic sensor, an electro-magnetic sensor, a voltage meter, a thermal sensor, a flow meter, or a piezo-meter. In some embodiments, the central control unit also includes a pre-amplifier, a lock-in amplifier, a thermal sensor, a flow meter, an optical sensor, an acoustic detector, an imaging device, a camera, a piezo-electrical sensor, a piezo-photronic sensor, a piezo-electro photronic sensor, an electro-optical sensor, an electro-thermal sensor, a bio-electrical sensor, a bio-marker sensor, a bio-chemical sensor, a chemical sensor, an ion emission sensor, a photo-detector, an electrical meter, a switching matrix, a system bus, a nonvolatile storage device, or a random access memory.

In some embodiments, the central control unit comprises a display unit for displaying the detected result or analysis result. In some other embodiments, the central control unit is connected to a computer and operated with computer software.

In some embodiments, the apparatus of this invention further comprises a system that is connected to each sub-equipment unit for reclaiming or treatment medical waste from each sub-equipment unit. The reclaiming and treatment of medical waste can be performed by the same system or two different systems.

In some embodiments, multiple fabricated micro-devices can be coupled, joined, and connected by physical or electrical method to constitute the more advanced devices.

In some embodiments, the apparatus of this invention can be integrated on a single device (e.g., by using a semiconductor processing technology) or assembled on a board (e.g., by using a computer packaging technology).

In some embodiments, the layer of material that defines the inter-unit or intra-unit channel comprises silicon dioxide biocompatible material on its interior surface. The biocompatible material is a synthetic polymeric material, phosphate based material, carbone based material, carbone oxide based material, carbone oxynitride based material, or naturally occurring biological material.

In some embodiments, the sub-equipment unit or the delivery system or the central control unit is fabricated by microelectronics technologies.

In some embodiments, the disease to be detected by the apparatus of this invention is a cancer, e.g., breast cancer, lung cancer, esophageal cancer, cervical cancer, ovarian cancer, rectum cancer, intestine cancer, cancer related to blood, liver cancer, stomach cancer, or circulating tumor cells.

Experiments utilizing the novel apparatus disclosed in this application have been carried out on multiple types of cancer. Good cancer detection results in terms of measurement sensitivity and specificity have been obtained on multiple types of cancer tested, demonstrating the validity of the apparatus of this invention for improved ability to detect diseases (e.g., cancers), particularly in their early stages. The experimental results have also shown that multiple cancer types can be detected using the apparatus of this invention, which is an improvement over many existing detection apparatus.

Another aspect of this invention provides a method for detecting a disease, comprising contacting the diseased biological subject with a detection apparatus which comprises:

a first sub-equipment unit for detecting a property of the biological subject;

at least one additional sub-equipment unit for detecting the same or different property of the biological subject as the first sub-equipment unit;

a delivery system comprises at least one intra-unit channels for transporting the biological subject to one or more desired sub-equipment units;

optionally, a central control system that is connected to each sub-equipment unit and the delivery system, and capable of controlling the biological subject matter to be transported to one or more desired sub-equipment units and reading, analyzing or displaying a detected data from each sub-equipment unit;

optionally, a reclaiming or treatment system that is connected to each sub-equipment unit for reclaiming or treatment medical waste from each sub-equipment unit;

wherein each sub-equipment unit optionally comprises an inter-unit channel, a sorting unit, a detection unit, a probing unit, or a pre-screening unit.

In some embodiments, the diseased biological subject is cells, a sample of an organ or tissue, DNA, RNA, virus, or protein. For example, the cells are circulating tumor cells or cancer cells, e.g., breast cancer, lung cancer, esophageal cancer, cervical cancer, ovarian cancer, rectum cancer, intestine cancer, cancer related to blood, liver cancer, stomach cancer, or circulating tumor cells. In some other embodiments, the biological subject is contained in a media and transported into the first intra-unit channel.

As used herein, the term "or" is meant to include both "and" and "or". It may be interchanged with "and/or."

As used herein, a singular noun is meant to include its plural meaning. For instance, a micro device can mean either a single micro device or multiple micro-devices.

As used herein, the term "patterning" means shaping a material into a certain physical form or pattern, including a plane (in which case "patterning" would also mean "planarization.")

As used herein, the term "a biocompatible material" refers to a material that is intended to interface with a living organism or a living tissue and can function in intimate contact therewith. When used as a coating, it reduces the adverse reaction a living organism or a living tissue has against the material to be coated, e.g., reducing the severity or even eliminating the rejection reaction by the living organism or living tissue. As used herein, it encompasses both synthetic materials and naturally occurring materials. Synthetic materials usually include biocompatible polymers, made either from synthetic or natural starting materials, whereas naturally occurring biocompatible materials include, e.g., proteins or tissues.

As used herein, the term "a biological subject" or "a biological sample" for analysis or test or diagnosis refers to the subject to be analyzed by a disease detection apparatus. It can be a single cell, a single biological molecular (e.g., DNA, RNA, or protein), a single biological subject (e.g., a single cell or virus), any other sufficiently small unit or fundamental biological composition, or a sample of a subject's organ or tissue that may having a disease or disorder.

As used herein, the term "disease" is interchangeable with the term "disorder" and generally refers to any abnormal microscopic property or condition (e.g., a physical condition) of a biological subject (e.g., a mammal or biological species).

As used herein, the term "subject" generally refers to a mammal, e.g., a human person.

As used herein, the term "microscopic level" refers to the subject being analyzed by the disease detection apparatus of this invention is of a microscopic nature and can be a single cell, a single biological molecular (e.g., DNA, RNA, or protein), a single biological subject (e.g., a single cell or virus), and other sufficiently small unit or fundamental biological composition.

As used herein, a "micro-device" or "micro device" can be any of a wide range of materials, properties, shapes, and degree of complexity and integration. The term has a general meaning for an application from a single material to a very complex device comprising multiple materials with multiple sub units and multiple functions. The complexity contemplated in the present invention ranges from a very small, single particle with a set of desired properties to a fairly complicated, integrated unit with various functional units contained therein. For example, a simple micro-device could be a single spherical article of manufacture of a diameter as small as 100 angstroms with a desired hardness, a desired surface charge, or a desired organic chemistry absorbed on its surface. A more complex micro device could be a 1 millimeter device with a sensor, a simple calculator, a memory unit, a logic unit, and a cutter all integrated onto it. In the former case, the particle can be formed via a fumed or colloidal precipitation process, while the device with various components integrated onto it can be fabricated using various integrated circuit manufacturing processes. In some places, a micro-device or micro device represents a sub-equipment unit.

As used herein, if not specifically defined, a "channel" can be either an inter-unit channel or an intra-unit channel.

An apparatus or micro-device used in the present invention can range in size (e.g., diameter) from on the order of about 1 angstrom to on the order of about 5 millimeters. For instance, a detection apparatus ranging in size from on the order of about 10 angstroms to on the order of 100 microns can be used in this invention for targeting biological molecules, entities or compositions of small sizes such as cell structures, DNA, and bacteria. Or, a micro-device ranging in size from on the order of about one micron to the order of about 5 millimeters can be used in the present invention for targeting relatively large biological matters such as a portion of a human organ. As an example, a simple apparatus defined in the present application can be a single particle of a diameter less than 100 angstroms, with desired surface properties (e.g., with surface charge or a chemical coating) for preferential absorption or adsorption into a targeted type of cell.

The present invention further provides an apparatus for detecting a disease in a biological subject, which comprises a pre-processing unit, a delivery system, a probing and detecting unit comprising at least two sub-equipment units, a signal processing unit, and a disposal processing unit.

In some embodiments of the apparatus, the pre-processing unit includes a sample filtration unit, a recharging unit, a constant pressure delivery unit, and a sample pre-probing disturbing unit. This increases the contraction ratio of certain substance of interests (such as cancer cells) and therefore makes the apparatus more effective and efficient in detecting the targeted biological subject (such as cancer cells).

In some embodiments, the filtration unit can filter off unwanted substance by physical filtration (e.g., based on the electronic charge or size of the substance) or separation by chemical reaction (thereby completely removing the undesirable substances), biochemical reaction, electro-mechanical reaction, electro-chemical reaction, or biological reaction.

In some embodiments, the sample filtration unit can include an entrance channel, a disturbing fluid channel, an accelerating chamber, and a slit. The slit and the interior walls of the entrance channel define two channels (e.g., a top channel and a bottom channel) wherein the biological subject can be separated due to the differences in its property (e.g., electrical or physical property).

In some embodiments, a bio-compatible fluid can be injected into the disturbing fluid channel to separate the biological subject. For example, the bio-compatible fluid can be injected from the entrance of the disturbing fluid channel and deliver to an opening in the entrance channel wall. The bio-compatible fluid can be liquid or semi-liquid, and can include saline, water, plasma, an oxygen-rich liquid, or any combination thereof.

In some other embodiments, the angle between the entrance channel and the disturbing fluid channel ranges from about 0° to about 180° (e.g., from about 30° to about 150°, from about 60° to about 120°, or from about 75° to about 105°, or about 90°).

In some other embodiments, the width of each channel (e.g., inter-unit channel, intra-unit channel, entrance unit, disturbing fluid channel, etc.) can range from about 1 nm to about 1 mm (e.g., from about 2 nm to about 0.6 mm or from about 10 nm to about 0.2 mm).

In some other embodiments, at least one of the channels comprises one probing device attached to the channel's sidewall, and the probing device is capable of measuring at the microscopic level a thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical optical, bio-electro-thermal-optical, bio-electro-chemical-mechanical, electrical, magnetic, electromagnetic, physical or mechanical property, or a combination thereof, of the biological subject.

In some embodiments, at least one of the channels (e.g., inter-unit channel, intra-unit channel, entrance unit, disturbing fluid channel, etc.) comprises at least two probing devices attached to the channel's sidewalls, and the probing devices are capable of measuring at the microscopic level a thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical optical, bio-electro-thermal-optical, bio-electro-chemical-mechanical, electrical, magnetic, electromagnetic, physical or mechanical property, or a combination thereof, of the biological subject. The probing devices measure the same or different properties at the same time or different times.

The two or more probing devices can be placed with a desired distance between each other (at least 10 angstroms). Examples of the desired distance include from about 5 nm to about 100 mm, from about 10 nm to about 10 mm, from about 10 nm to about 5 mm, from about 10 nm to about 1 mm, from about 15 nm to about 500 nm.

In some embodiments, the apparatus of this invention comprises at least one probe and at least one detector. The probe can be utilized to launch a probing (disturbing or simulating) signal to probe (i.e., disturb or stimulate) the biological subject, and the detector can detect the biological subject's response (signal) to the probing signal. As an example, a micro-device with at least one acoustic probe (such as an acoustic transducer or microphone) and at least one detector (such as an acoustic signal receiver) is utilized for biological subject detection, wherein the acoustic probe and detector may be constructed with, among others, one or more piezo-electrical materials. In this example, an acoustic signal is first launched, and scanned across its frequency range (e.g., from sub Hz to over MHz) by the probe. The response signal to the launched acoustic signal by the probe is then collected by the detector, and subsequently recorded, amplified (e.g., by a lock-in amplifier), and analyzed. The response signal contains characteristic information of a biological subject that is tested. For example, depending on certain properties of the tested biological subject, the detected acoustic resonant frequency, intensity, frequency versus intensity spectrum, or intensity distribution by the detector may indicate characteristic information about the tested biological subject. Such information includes density, density distribution, absorption properties, shape, surface properties, and other static and dynamic properties of the biological subject.

In some embodiments, the sample filtration unit can include an entrance channel, a biocompatible filter, an exit channel, or any combination thereof. When a biological subject passes through the entrance channel toward the exit channel, the biological subject of a size larger than the filter hole will be blocked against the exit channel, resulting in the smaller biological subject being flushed out through the exit channel. A biocompatible fluid is injected from the exit to carry the biological subject accumulated around the filter and flush out from the channel. The biological subject with a large size is then filtered for further analysis and detection in the detecting component or unit of the apparatus.

In some embodiments, the sample pre-probing disturbing unit can include one micro-device with a channel, a slit located inside the channel, and optionally two plates outside the channel. The two plates can apply a signal, e.g., an electronic voltage, to the biological subject traveling through the channel and separates it based on the electronic charge the biological subject carries. The slit and the interior channels of the channel define two channels where the separated biological subjects enter and optionally are detected for its property at the microscopic level.

In some embodiments, the sample pre-probing disturbing unit applies to the biological subject a thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical optical, bio-electro-thermal-optical, bio-electro-chemical-mechanical, electrical, magnetic, electromagnetic, physical or mechanical signal, or a combination thereof. The signal can be applied, e.g., with the two plates described above or in other means (depending on the nature of the signal). The signal as applied can be pulsed or constant.

In some embodiments, the recharging unit recharges nutrient or respiring gas (such as oxygen) to the biological subject. Alternatively, it can also clean up the metabolite of the biological subject. With such a recharging unit, the life stability of the biological subject in the sample is sustained and its use is extended, thereby giving more accurate and reliable detecting results. Examples of nutrient include biocompatible strong or weak electrolyte, amino acid, mineral, ions, oxygen, oxygen-rich liquid, intravenous drip, glucose, and protein. Another example of the nutrient is a solution containing nano-particles that can be selectively absorbed by certain biological subjects (e.g., cells or viruses).

The recharging system can be separate from and outside of the other components of the apparatus. Alternatively, it can also be installed within one of the other components, e.g., the probing and detecting unit or the disposal processing unit.

In some other embodiments, the signal processing unit comprises an amplifier (e.g., a lock-in amplifier), an A/D (alternate/direct electrical current or analog to digital) converter, a micro-computer, a manipulator, a display, and network connections.

In some instance, the signal processing unit collects more than one signal (i.e., multiple signals), and the multiple signals can be integrated to cancel out noise or to enhance the signal to noise ratio. The multiple signals can be signals from multiple locations or from multiple times.

The invention further provides a method for detecting a disease with enhanced sensibility in a subject in need thereof, which comprises: taking a biological sample from the subject and taking a biological sample from a disease-free subject; optionally placing the biological sample in a biocompatible media; analyzing the two biological samples to measure a property thereof at the microscopic level with a micro-device which comprises a first micro sensor for detecting a property of the biological samples at the microscopic level, and an interior wall defining a channel, wherein the micro sensor is located in the interior wall of the micro-device and detects the property of the biological samples at the microscopic level, and the biological sample is transported within the channel; and comparing the measured property of the two biological samples.

In some embodiments, the apparatus further comprises a second micro sensor for applying a probing signal on the biological samples or on the optional media, thereby changing and optimizing (enhancing) the nature or value of the property to be detected at the microscopic level. This process would result in amplified or enhanced value of the property to be detected, which in turn makes the property easier to detect and measure, thus increasing the sensibility of the detection and measure. The probing signal and the property to be detected can be of the same type or different types. For example, the probing signal and the property to be detected can both be an electrical property or an optical property or a mechanical property or a thermal property. Or, the probing signal and the property to be detected can be, e.g., an optical property and an electrical property, an optical property and a magnetic property, an electrical property and a mechanic property, a mechanical property and an electrical property, a chemical property and a biological property, a physical property and an electrical property, an electrical property and a thermal property, a bio-chemical property and a physical property, a bio-electro-mechanical property and a thermal property, a bio-chemical property and an electrical property, a bio-chemical property and an optical property, a bio-chemical property and a thermal property, a bio-chemical property and a chemical property, a biological property and an electrical property, a biological property and an optical property, and a biological property and a thermal property, respectively.

Each of the probing signal and the property to be detected can be a thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical optical, bio-electro-thermal-optical, bio-electro-chemical-mechanical, electrical, magnetic, electromagnetic, physical or mechanical property of the biological subject, or a combination thereof.

In some embodiments, the change of the property is from a static state to a dynamic or pulse state, or from a lower value to a higher value.

In some other embodiments, the probing signal or at least one of the parameters of the environmental setting in which the biological subject to be measured resides is changed from one value to a new value, or from a static state to a dynamic state, in order to further enhance the property to be detected and thus optimize the measure sensibility of the micro-device. Such parameters or probing signal include, but are not limited to, optical, thermal, bio-chemical, chemical, mechanical, physical, acoustical, bio-electrical, bio-optical, electro-optical, electro-chemical, electro-chemical optical, electrical, electro-magnetic, or a combination thereof. Specifically, examples of the probing signal and a property of the media include, but are not limited to, laser intensity, temperature, catalyst concentration, acoustic energy, bio-marker concentration, electrical voltage, electrical current, fluorescent dye concentration, the amount of agitation in the biological samples, and fluid flow rate.

Specifically, in order to enhance measurement sensitivity and maximize the difference in signals between normal biological samples and diseased biological samples, applied probing (disturbing) signal and/or at least one of the parameters of the environmental surrounding in which the biological sample resides is intentionally changed from one value to a new value, or from a static value (DC value) to a pulsed value (AC value). The new value can be optimized to trigger maximum response from the biological sample. The new value can also be optimized to obtain enhanced difference in measured signals between the normal biological sample and diseased sample, resulting in enhanced measurement sensitivity. For example, for making dynamic measurements to further enhance measurement sensitivity, during measurements, at least one of the parameters applied to the biological sample being measured or at least one of the properties in the surrounding media (in which the biological sample resides) is intentionally changed from a static state (constant value) to a dynamic state (for example, a pulsed value or an alternating value), or from one value to a new value. As a novel example, in a measurement, a DC current applied to a biological sample is intentionally changed to an AC current. In another novel example, a constant temperature applied to a biological sample is changed to a higher temperature, or a pulsed heat wave (for example, from 30° C. to 50° C., then from 50° C. back to 30° C.). The above disclosed inventive method (the utilization of dynamic probing (disturbing or stimulating) signal, optimized probing (disturbing or stimulating) value and probing signal ramp-up speed) can also be used in conjunction with various lock-in techniques including but not limited to phase lock-in technique and/or the use of pulsed or alternating probing signal with signal amplification synchronized to the frequency of the probing signal.

Biological subjects that can be detected by the apparatus include, e.g., blood, urine, saliva, tear, and sweat. The detection results can indicate the possible occurrence or presence of a disease (e.g., one in its early stage) in the biological subject.

As used herein, the term "absorption" typically means a physical bonding between the surface and the material attached to it (absorbed onto it, in this case). On the other hand, the word "adsorption" generally means a stronger, chemical bonding between the two. These properties are very important for the present invention as they can be effectively used for targeted attachment by desired micro devices for measurement at the microscopic level.

As used herein, the term "contact" (as in "the first micro-device contacts a biologic entity") is meant to include both "direct" (or physical) contact and "non-direct" (or indirect or non-physical) contact. When two subjects are in "direct" contact, there is generally no measurable space or distance between the contact points of these two subjects; whereas when they are in "indirect" contact, there is a measurable space or distance between the contact points of these two subjects.

As used herein, the term "probe" or "probing," in addition to its dictionary meaning, could mean applying a signal (e.g., an acoustic, optical, magnetic, chemical, electrical, electro-magnetic, bio-chemical, bio-physical, or thermal signal) to a subject and thereby stimulating the subject and causing it to have some kind of intrinsic response.

As used herein, the term "thermal property" refers to temperature, freezing point, melting point, evaporation temperature, glass transition temperature, or thermal conductivity.

As used herein, the term "optical property" refers to reflection, optical absorption, optical scattering, wave length dependent properties, color, luster, brilliance, scintillation, or dispersion.

As used herein, the term "electrical property" refers to surface charge, surface potential, electrical field, charge distribution, electrical field distribution, resting potential, action potential, or impedance of a biological subject to be analyzed.

As used herein, the term "magnetic property" refers to diamagnetic, paramagnetic, or ferromagnetic.

As used herein, the term "electromagnetic property" refers to property that has both electrical and magnetic dimensions.

As used herein, the term "acoustical property" refers to the characteristics found within a structure that determine the quality of sound in its relevance to hearing. It can generally be measured by the acoustic absorption coefficient. See, e.g., U.S. Pat. No. 3,915,016, for means and methods for determining an acoustical property of a material; T. J. Cox et al., *Acoustic Absorbers and Diffusers*, 2004, Spon Press.

As used herein, the term "biological property" is meant to generally include chemical and physical properties of a biological subject.

As used herein, the term "chemical property" refers to pH value, ionic strength, or bonding strength within the biological sample.

As used herein, the term "physical property" refers to any measurable property the value of which describes a physical system's state at any given moment in time. The physical properties of a biological sample may include, but are not limited to absorption, albedo, area, brittleness, boiling point, capacitance, color, concentration, density, dielectrical, electrical charge, electrical conductivity, electrical impedance, electrical field, electrical potential, emission, flow rate, fluidity, frequency, inductance, intrinsic impedance, intensity, irradiance, luminance, luster, malleability, magnetic field, magnetic flux, mass, melting point, momentum, permeability, permittivity, pressure, radiance, solubility, specific heat, strength, temperature, tension, thermal conductivity, flow rate, velocity, viscosity, volume, surface area, shape, and wave impedance.

As used herein, the term "mechanical property" refers to strength, hardness, flow rate, viscosity, toughness, elasticity, plasticity, brittleness, ductility, shear strength, elongation strength, fracture stress, or adhesion of the biological sample.

As used herein, the term "disturbing signal" has the same meaning as "probing signal" and "stimulating signal."

As used herein, the term "disturbing unit" has the same meaning as "probing unit" and "stimulating unit."

As used herein, the term "conductive material" (or its equivalent "electrical conductor") is a material which contains movable electrical charges. A conductive material can be a metal (e.g., copper, silver, or gold) or non-metallic (e.g., graphite, solutions of salts, plasmas, or conductive polymers). In metallic conductors, such as copper or aluminum, the movable charged particles are electrons (see electrical conduction). Positive charges may also be mobile in the form of atoms in a lattice that are missing electrons (known as holes), or in the form of ions, such as in the electrolyte of a battery.

As used herein, the term "electrically insulating material" (also known as "insulator" or "dielectric") refers to a material that resists the flow of electrical current. An insulating material has atoms with tightly bonded valence electrons. Examples of electrically insulating materials include glass or organic polymers (e.g., rubber, plastics, or Teflon).

As used herein, the term "semiconductor" (also known as "semiconducting material") refers to a material with electrical conductivity due to electron flow (as opposed to ionic conductivity) intermediate in magnitude between that of a conductor and an insulator. Examples of inorganic semiconductors include silicon, silicon-based materials, and germanium. Examples of organic semiconductors include such aromatic hydrocarbons as the polycyclic aromatic compounds pentacene, anthracene, and rubrene; and polymeric organic semiconductors such as poly(3-hexylthiophene), poly(p-phenylene vinylene), polyacetylene and its derivatives. Semiconducting materials can be crystalline solids (e.g., silicon), amorphous (e.g., hydrogenated amorphous silicon and mixtures of arsenic, selenium and tellurium in a variety of proportions), or even liquid.

As used herein, the term "biological material" has the same meaning of "biomaterial" as understood by a person skilled in the art. Without limiting its meaning, biological materials or biomaterials can generally be produced either in nature or synthesized in the laboratory using a variety of chemical approaches utilizing organic compounds (e.g., small organic molecules or polymers) or inorganic compounds (e.g., metallic components or ceramics). They generally can be used or adapted for a medical application, and thus comprise whole or part of a living structure or biomedical device which performs, augments, or replaces a natural function. Such functions may be benign, like being used for a heart valve, or may be bioactive with a more interactive functionality such as hydroxyl-apatite coated hip implants. Biomaterials can also be used every day in dental applications, surgery, and drug delivery. For instance, a construct with impregnated pharmaceutical products can be placed into the body, which permits the prolonged release of a drug over an extended period of time. A biomaterial may also be an autograft, allograft, or xenograft which can be used as a transplant material. All these materials that have found applications in other medical or biomedical fields can also be used in the present invention.

As used herein, the term "microelectronic technology or process" generally encompasses the technologies or processes used for fabricating micro-electronic and optical-electronic components. Examples include lithography, etching (e.g., wet etching, dry etching, or vapor etching), oxidation, diffusion, implantation, annealing, film deposition, cleaning, direct-writing, polishing, planarization (e.g., by chemical mechanical polishing), epitaxial growth, metallization, process integration, simulation, or any combinations thereof. Additional descriptions on microelectronic technologies or processes can be found in, e.g., Jaeger, Introduction to Microelectronic Fabrication, $2^{nd}$ Ed., Prentice Hall, 2002; Ralph E. Williams, Modern GaAs Processing Methods, $2^{nd}$ Ed., Artech House, 1990; Robert F. Pierret, Advanced Semiconductor Fundamentals, $2^{nd}$ Ed., Prentice Hall, 2002; S. Campbell, The Science and Engineering of Microelectronic Fabrication, $2^{nd}$ Ed., Oxford University Press, 2001, the contents of all of which are incorporated herein by reference in their entireties.

As used herein, the term "selective" as included in, e.g., "patterning material B using a microelectronics process selective to material A", means that the microelectronics process is effective on material B but not on material A, or is substantially more effective on material B than on material B (e.g., resulting in a much higher removal rate on material B than on material A and thus removing much more material B than material A).

As used herein, the term "carbon nano-tube" generally refers to as allotropes of carbon with a cylindrical nano-structure. See, e.g., Carbon Nanotube Science, by P. J. F. Harris, Cambridge University Press, 2009, for more details about carbon nano-tubes.

Through the use of a single micro-device or a combination of micro-devices integrated into a disease detection apparatus, the disease detection capabilities can be significantly improved in terms of sensitivity, specificity, speed, cost, apparatus size, functionality, and ease of use, along with reduced invasiveness and side-effects. A large number of micro-device types capable of measuring a wide range of microscopic properties of biological sample for disease detection can be integrated and fabricated into a single detection apparatus using micro-fabrication technologies and novel process flows disclosed herein. While for the purposes of demonstration and illustration, a few novel, detailed examples have been shown herein on how microelectronics or nano-fabrication techniques and associated process flows can be utilized to fabricate highly sensitive, multi-functional, and miniaturized detection devices, the principle and general approaches of employing microelectronics and nano-fabrication technologies in the design and fabrication of high performance detection devices have been contemplated and taught, which can and should be expanded to various combination of fabrication processes including but not limited to thin film deposition, patterning (lithography and etch), planarization (including chemical mechanical polishing), ion implantation, diffusion, cleaning, various materials, and various process sequences and flows and combinations thereof.

BRIEF DESCRIPTIONS OF THE FIGURES

FIGS. 1 (*b*) and (*c*) are illustration of a detection apparatus of this invention where multiple sub-equipment units are integrated.

Figure 13:
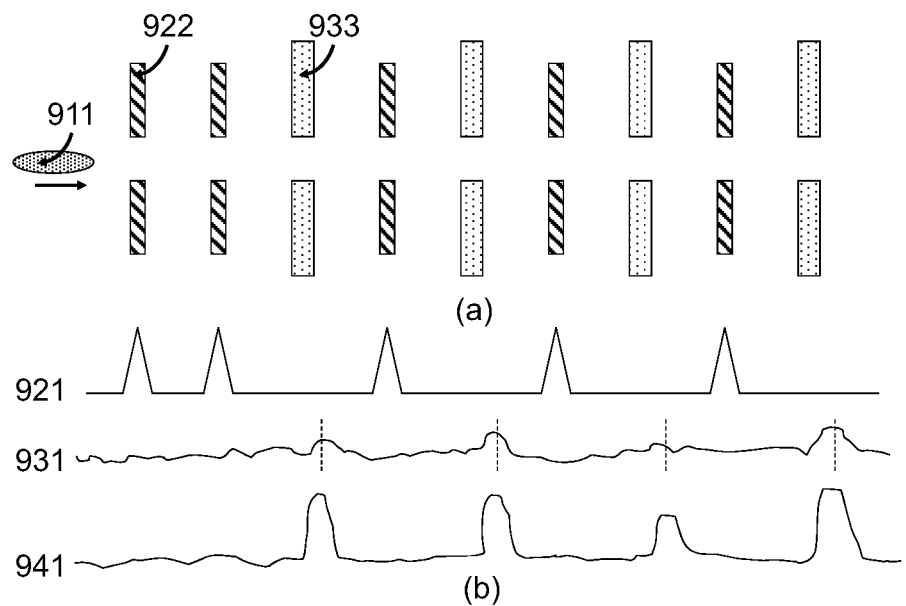

FIG. 13 illustrates a novel time of flight detection arrangement for detection applications, in which both clock signal generator and signal detection probes are used, along with schematically recorded clock signal, probe signal (signal detected by probing micro-device), and processed and enhanced signal after signal filtering using phase lock-in processing technique to enhance the detected signal.

Figure 14:
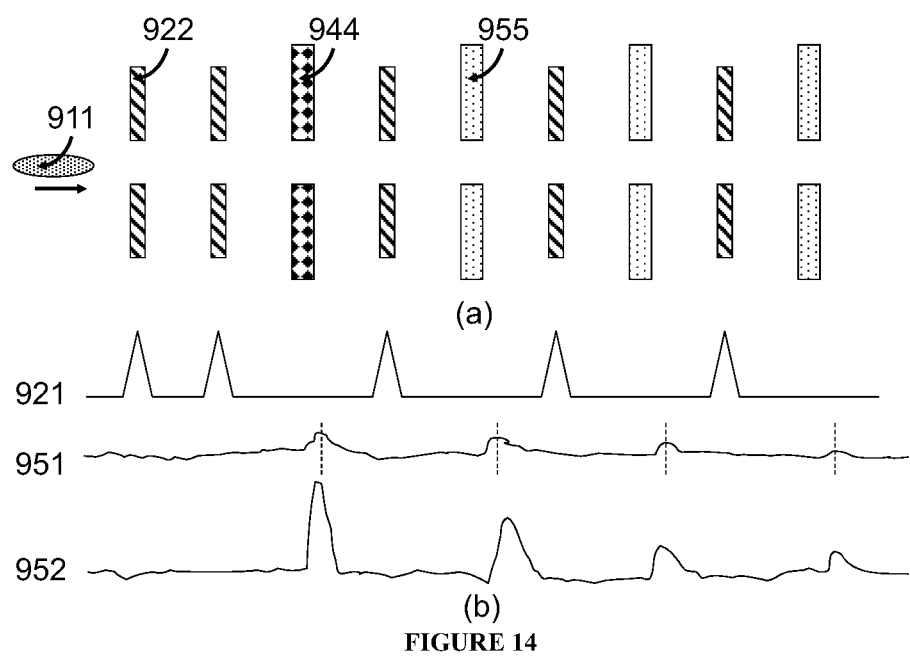

FIG. 14 illustrates yet another time of flight detection arrangement in which clock signal generators, a probe signal generator, and signal detection probes are used, along with schematically recorded clock signal, detected signal by probing micro-device in response to probe signal, and processed and enhanced signal after signal filtering using phase lock-in processing technique to enhance the detected signal showing detected response signal as a function of time (response signal delays over time in this case).

FIG. 15 illustrates another novel time of flight detection application, in which a set of novel micro-filters are utilized to detect biological entities via separation of biological entities by their various, specific properties such as size, weight, shape, electrical properties, or surface properties.

FIG. 16 illustrates a fluid delivery system, which is a pretreatment part for the detection apparatus, and it delivers a sample or auxiliary material at a desired pressure and speed into a device.

FIG. 17 illustrates how a micro-device in a disease detection apparatus of this invention can communicate, probe, detect, and optionally treat and modify biological subjects at a microscopic level.

Figure 18:
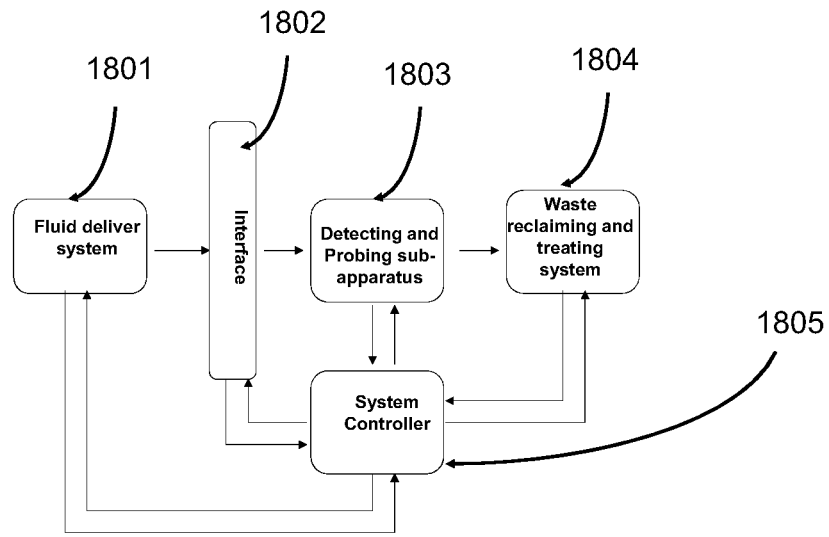

FIG. 18 illustrates a system block diagram of a detection apparatus, comprising various functional modules.

FIG. 19(a) illustrates how the signal is processed and responded in a single cell. FIGS. 19(b)-19(l) illustrate a novel device which can engage in cellular communications at the single cell level by simulating cellular signals and receiving the cell's responses which can be a signal of electro-magnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, electric, magnetic, physical, or mechanical property; and the unit is capable of communicating, trapping, sorting, analyzing, treating, or modifying a DNA and measuring the DNA's various properties.

Figure 20:
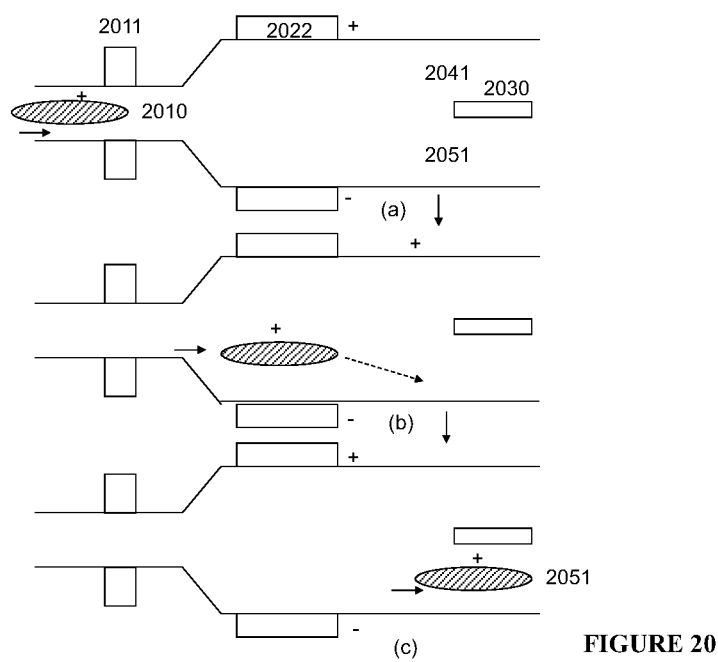

FIG. 20 illustrates a micro-device or sub-equipment that can detect the surface charge on biological subjects and separate them by a slit based on the charge.

Figure 21:
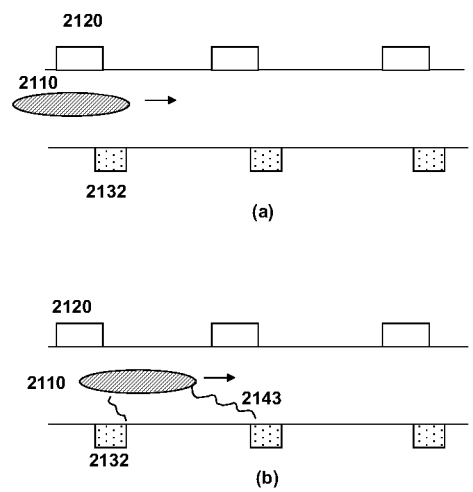

FIG. 21 illustrates another micro-device or sub-equipment that can detect the optical properties of the biological subject with a set of optical sensors.

Figure 22:
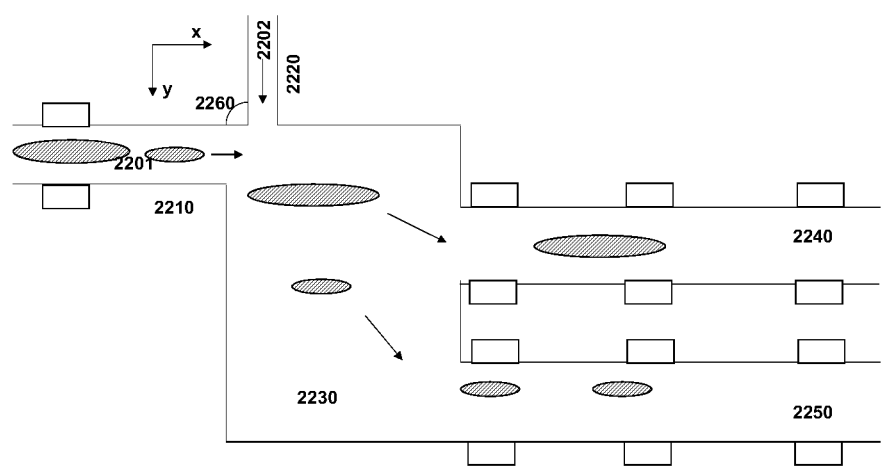

FIG. 22 illustrates another micro-device or sub-equipment that can separate biological subjects of different geometric size and detect their properties respectively.

Figure 23:
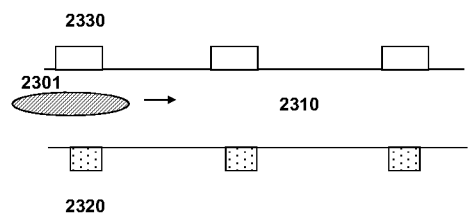

FIG. 23 illustrates a micro-device or sub-equipment that can measure the acoustic property of a biological subject.

Figure 24:

FIG. 24 illustrates a micro-device or sub-equipment that can measure the internal pressure of a biological subject.

Figure 25:
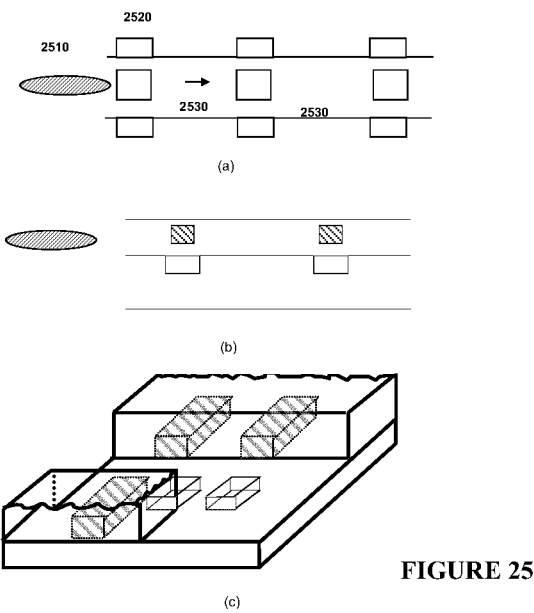

FIG. 25 illustrates a micro-device or sub-equipment that has concaves between the probe couples, in the bottom or ceiling of the channel.

Figure 26:
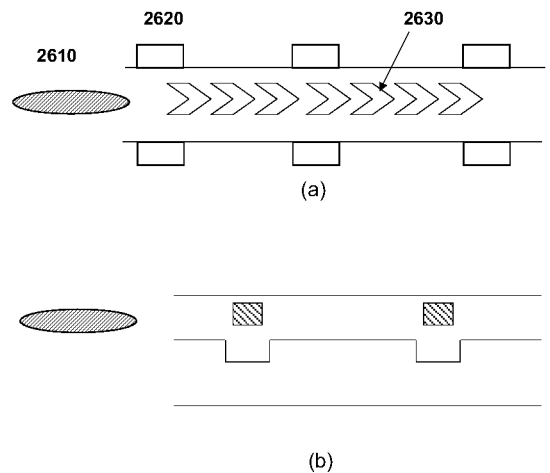

FIG. 26 illustrates another micro-device or sub-equipment that has concaves of a different shape from those illustrated in FIG. 25.

Figure 27:
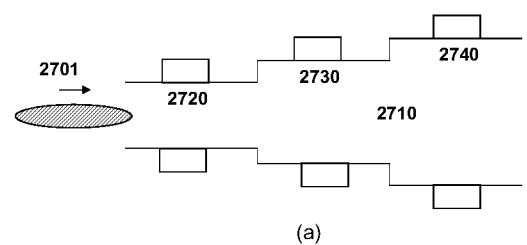

FIG. 27 illustrates a micro-device or sub-equipment that has a stepped channel.

Figure 28:
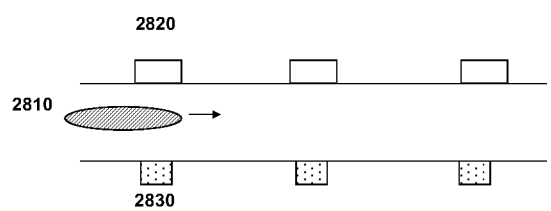

FIG. 28 illustrates a micro-device or sub-equipment that has a set of thermal meters.

Figure 29:
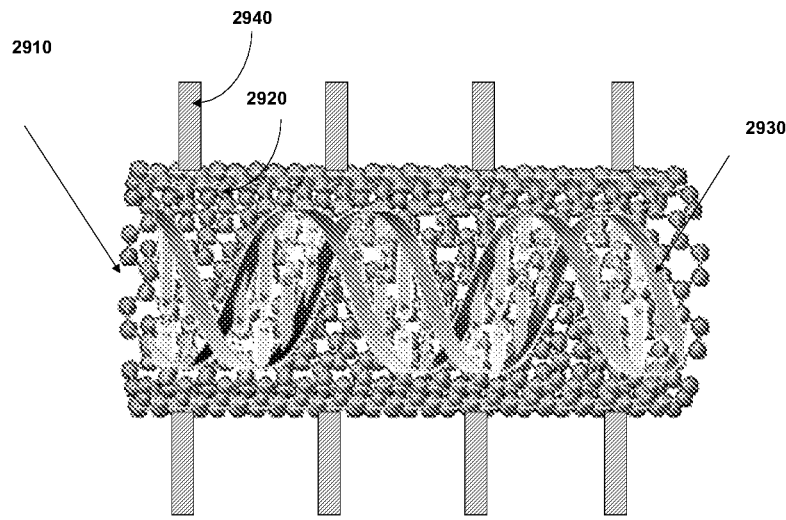

FIG. 29 illustrates a micro-device or sub-equipment that includes a carbon nano-tube as the channel with DNA contained therein.

Figure 30:
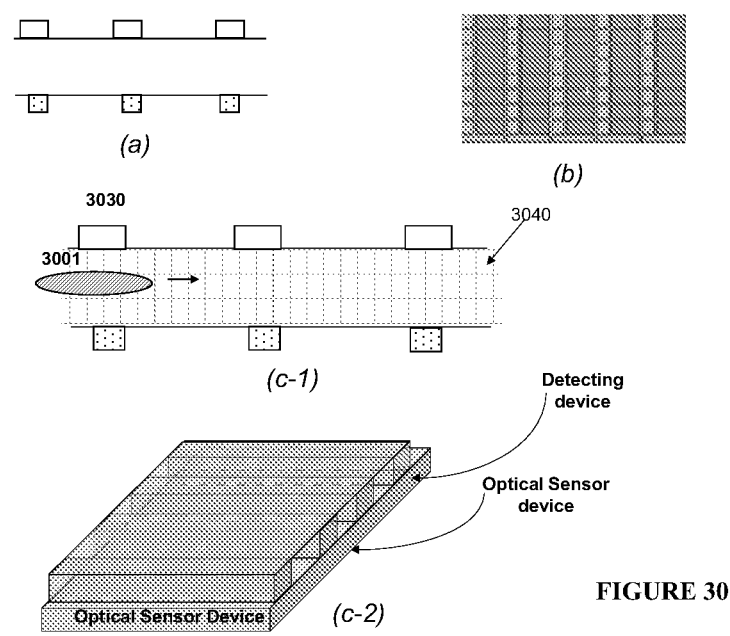
Figure 30:
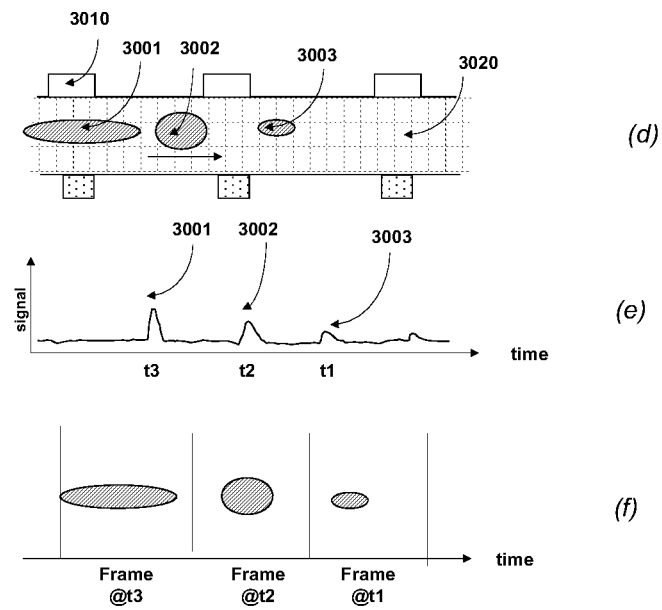

FIG. 30 illustrates a micro-device or sub-equipment that includes a detecting device and an optical sensor.

Figure 31:
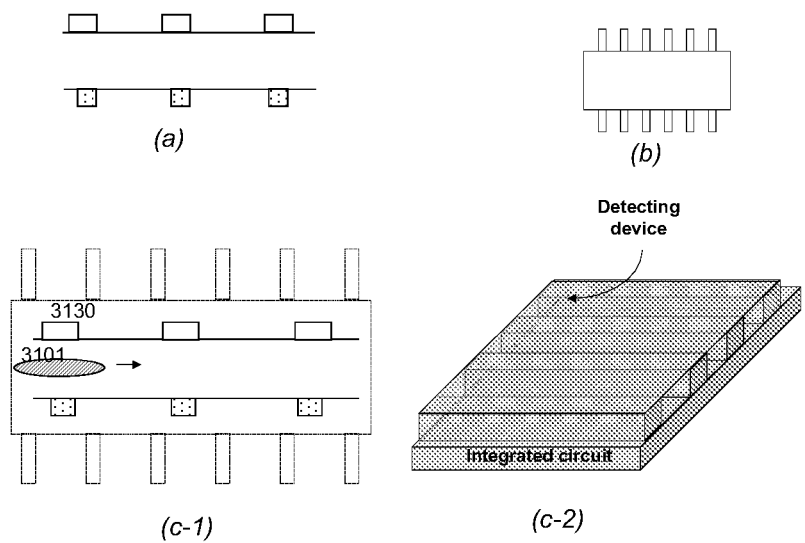

FIG. 31 illustrates an integrated apparatus of this invention that includes a detecting device and a logic circuitry.

Figure 32:
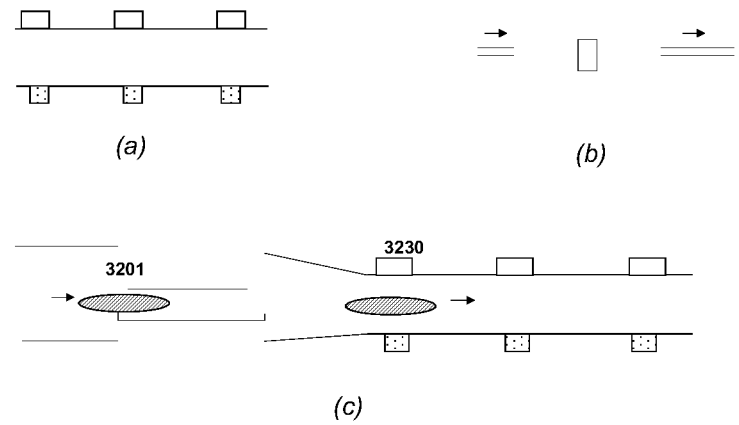
Figure 33:
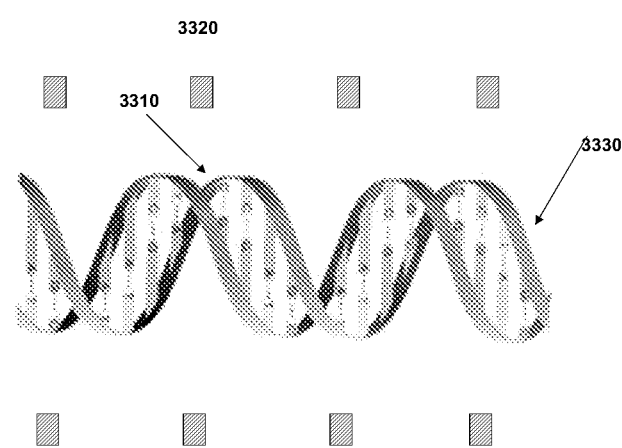

FIG. 32 illustrated a micro-device or sub-equipment that includes a detecting device and a filters FIG. 33 illustrates how apparatus of this invention can be used to measure a DNA' geometric factors.

Figure 34:
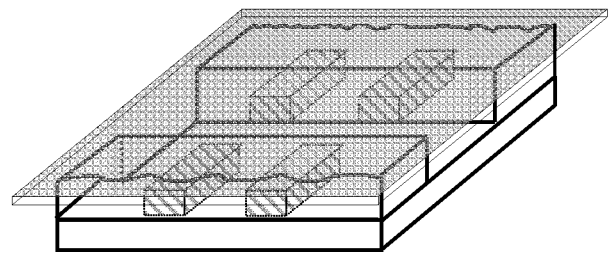

FIG. 34 illustrates an apparatus of this invention with a cover atop the trench to form a channel.

Figure 35:
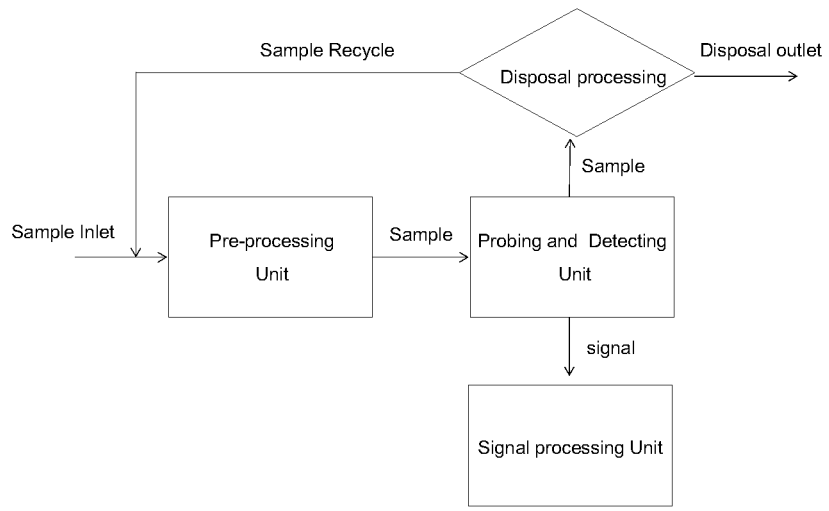

FIG. 35 is a diagram of sub-equipment unit for detecting a disease in a biological subject.

Figure 36:
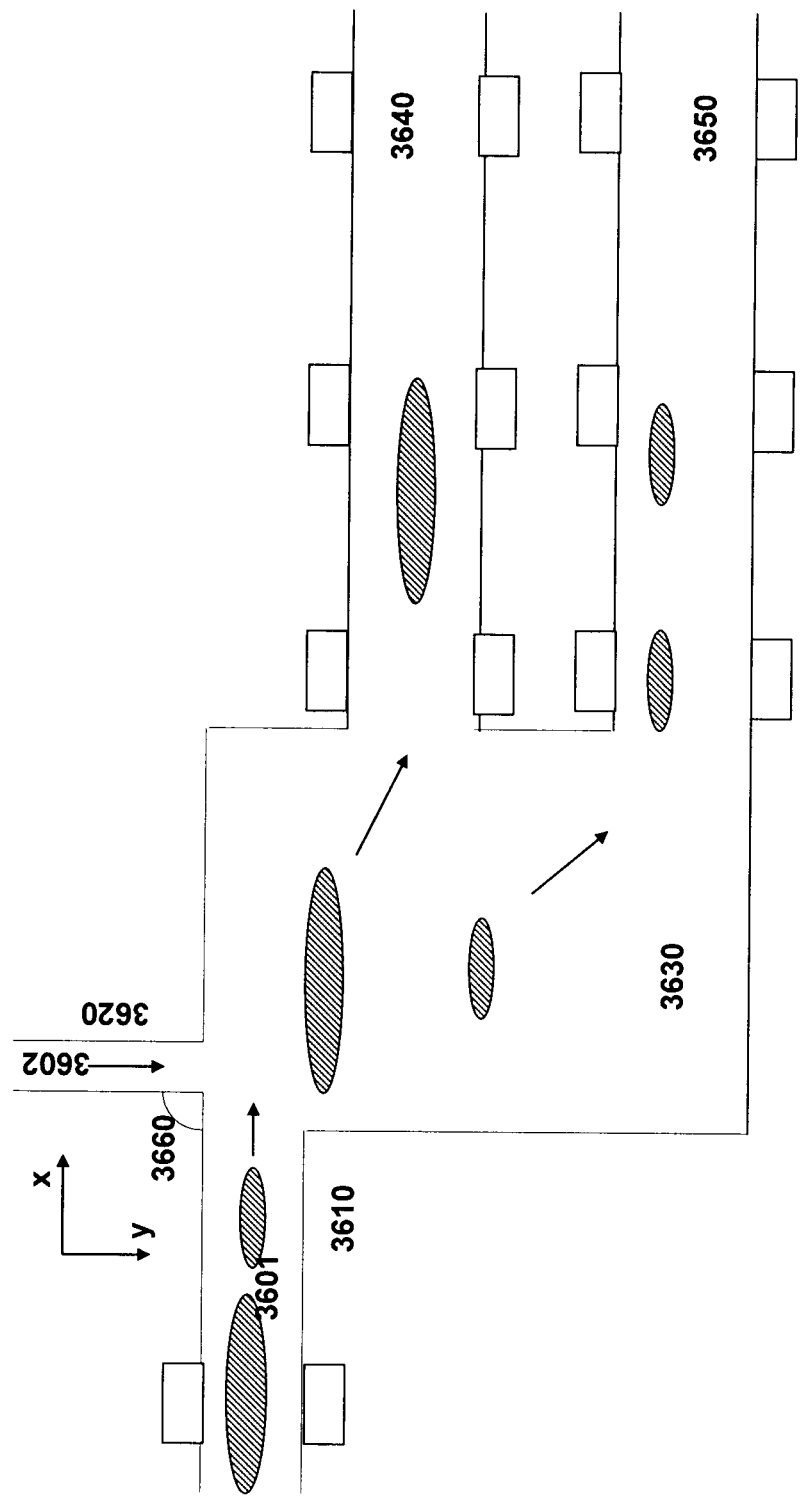

FIG. 36 shows an example of a sample filtration unit.

Figure 37:
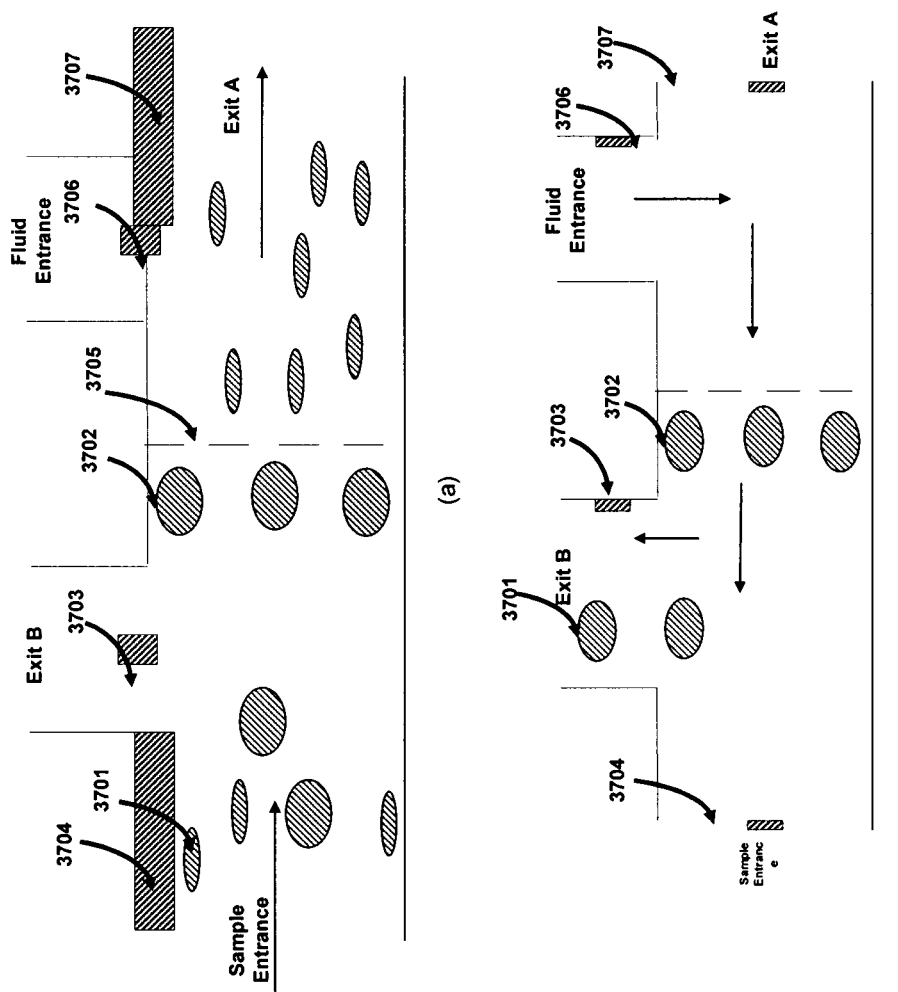

FIG. 37 shows another example of a sample filtration unit.

Figure 38:
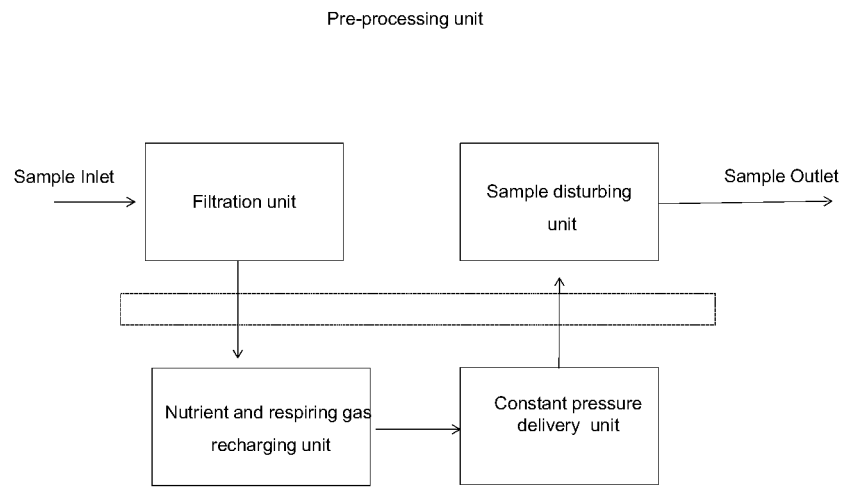

FIG. 38 is a diagram of a pre-processing unit of an apparatus of this invention.

Figure 39:
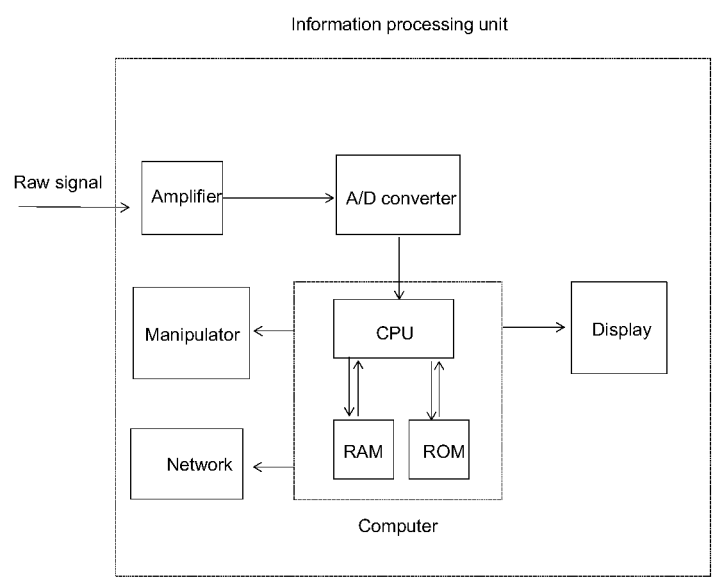

FIG. 39 is a diagram of an information processing unit of an apparatus of this invention.

Figure 40:
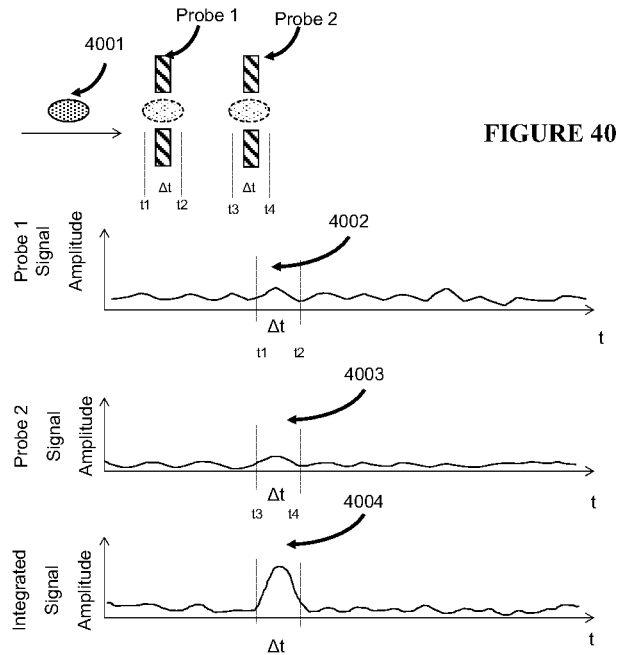

FIG. 40 shows the integration of multiple signals which results in cancellation of noise and enhancement of signal to noise ratio.

Figure 41:
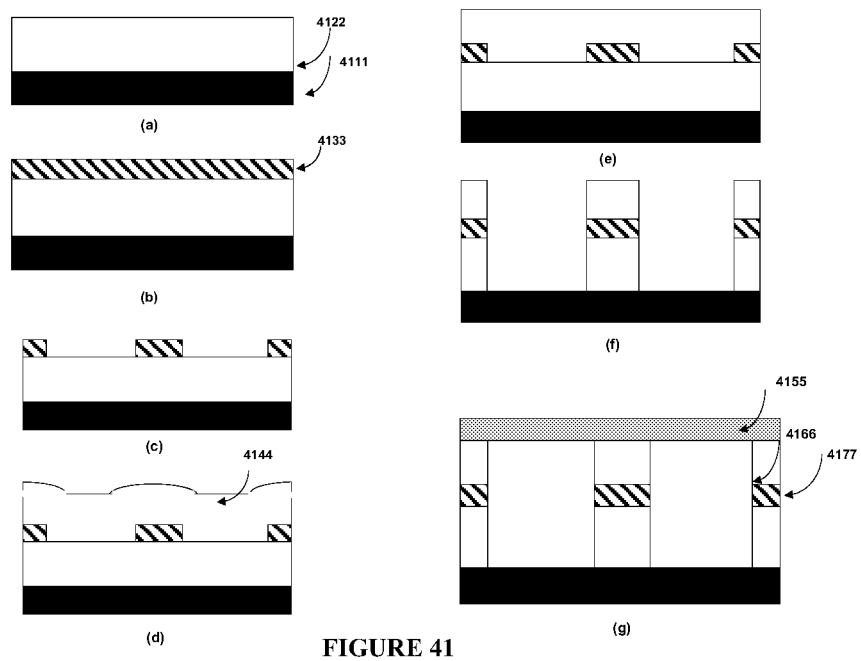

FIG. 41 shows one embodiment of the fabrication process of this invention for manufacturing a detection device with at least one detection chamber and at least one detector.

Figure 42:
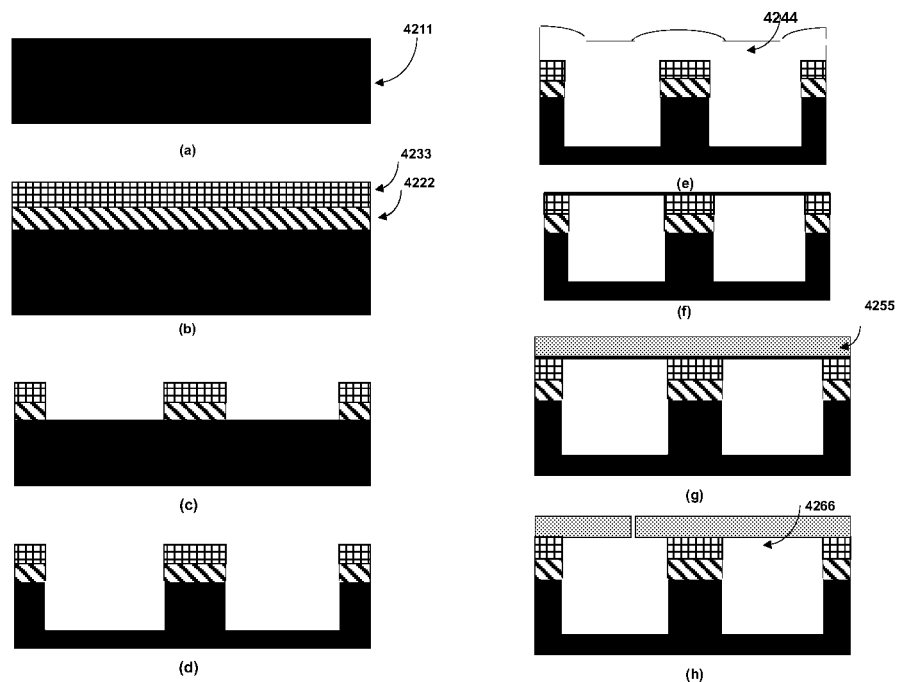
Figure 42:
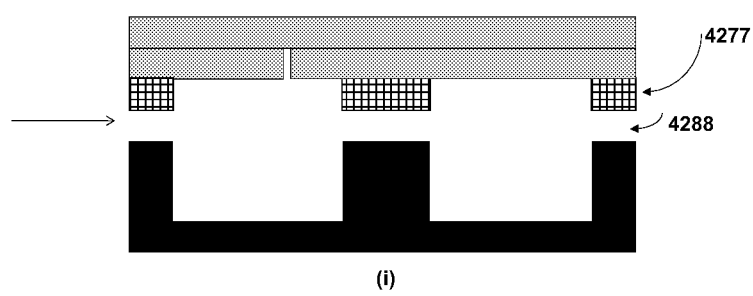

FIG. 42 shows another embodiment of a process of this invention for manufacturing a detection device with enclosed detection chambers, detectors, and channels for transporting biological samples such as fluidic samples.

Figure 43:
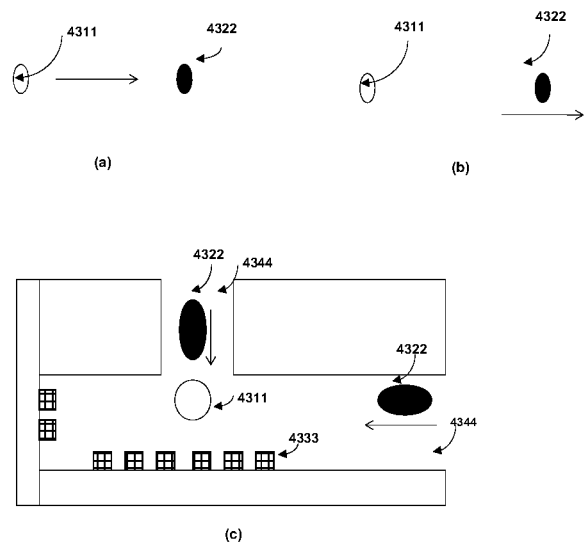

FIG. 43 shows a novel disease detection method in which at least one probe object is launched at a desired speed and direction toward a biological subject, resulting in a collision.

Figure 44:
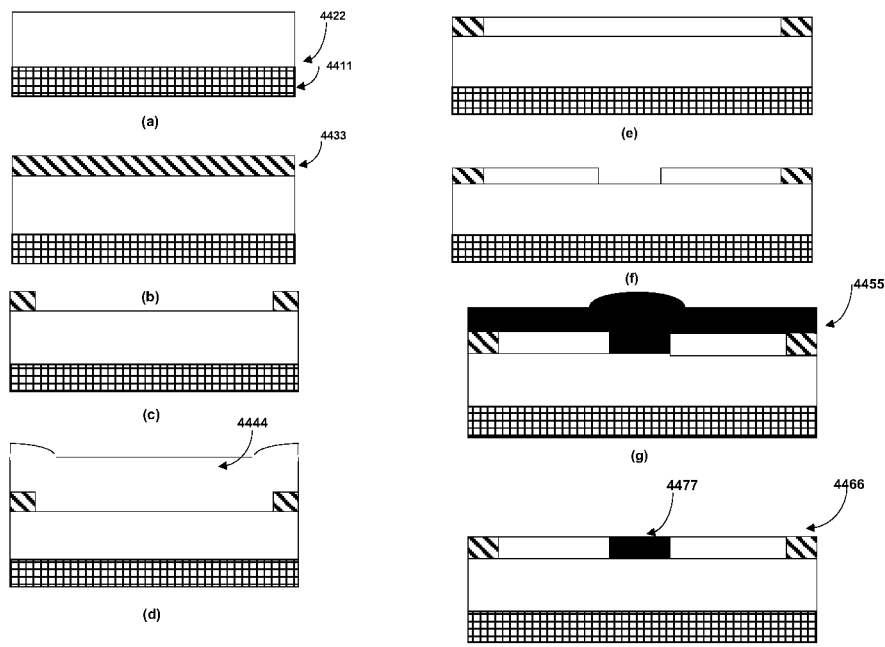

FIG. 44 illustrates a novel fabrication process of this invention for forming multiple components with different materials at the same device level.

Figure 45:
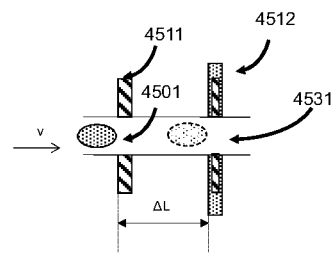

FIG. 45 shows a process of this invention for detecting a biological subject using disease detection apparatus.

Figure 46:
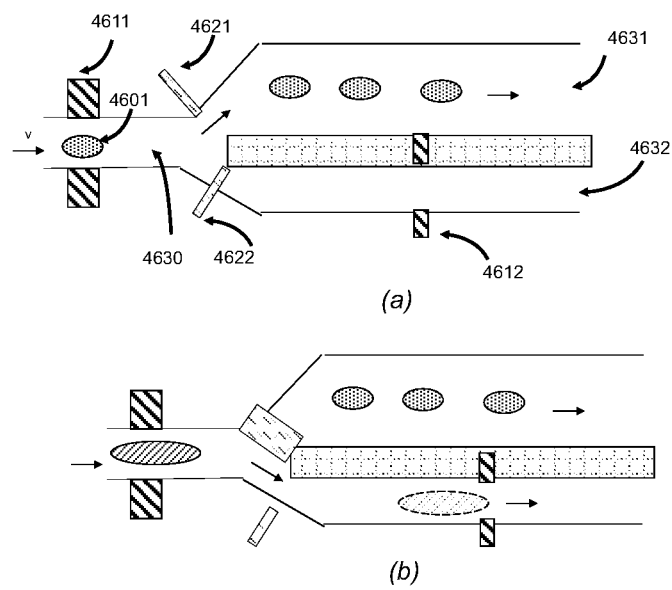

FIG. 46 shows another embodiment of disease detection process wherein diseased and healthy biological subjects are separated and the diseased biological subjects are delivered to further test.

Figure 47:
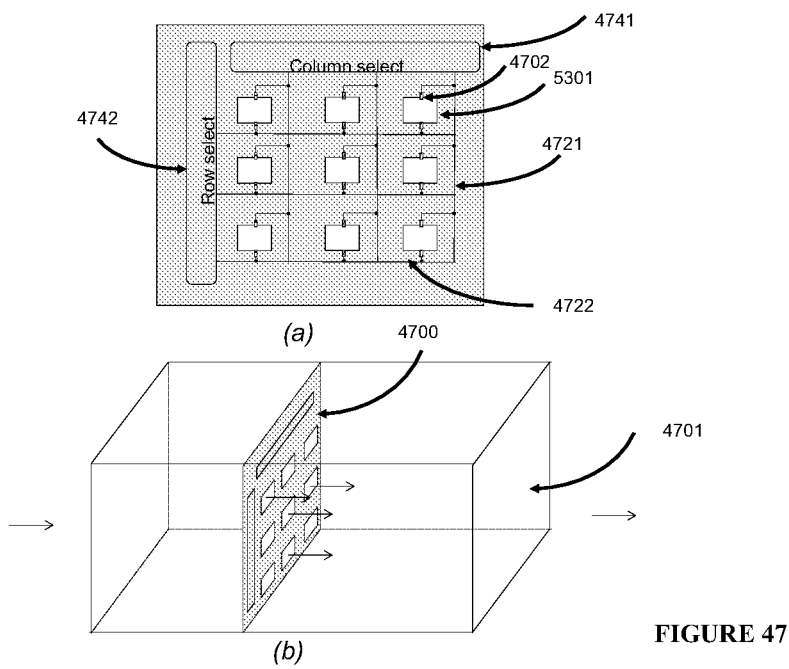

FIG. 47 shows an arrayed biological detecting device wherein a series of detecting devices fabricated into an apparatus.

Figure 48:
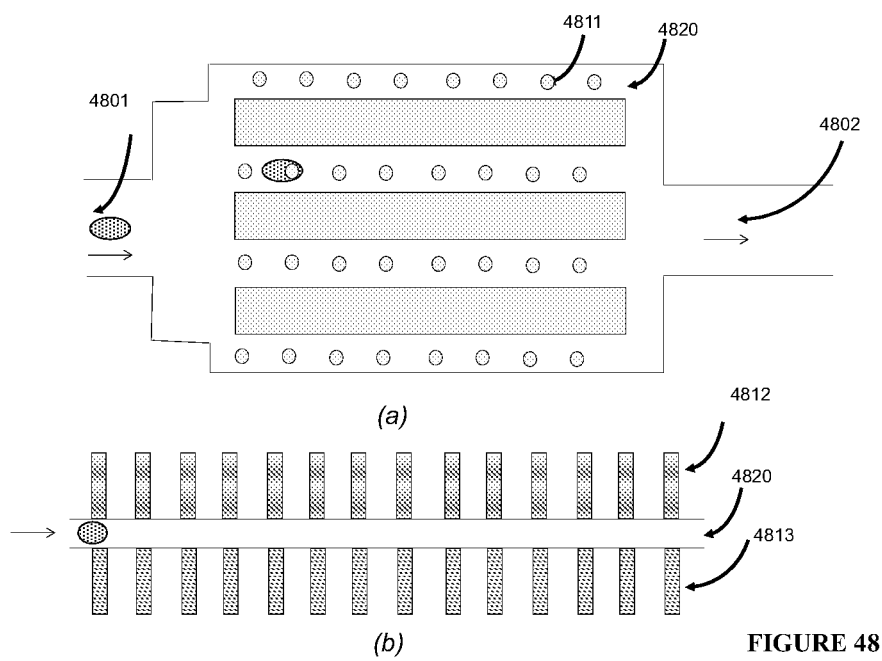

FIG. 48 shows another embodiment of a disease detection device of the current invention including inlet and outlet of the device, the channel where the biological subject passes through, and detection devices aligned along the walls of the channel.

FIG. 49 shows a schedule for fabricating a piezo-electrical micro-detector of this invention.

Figure 50:
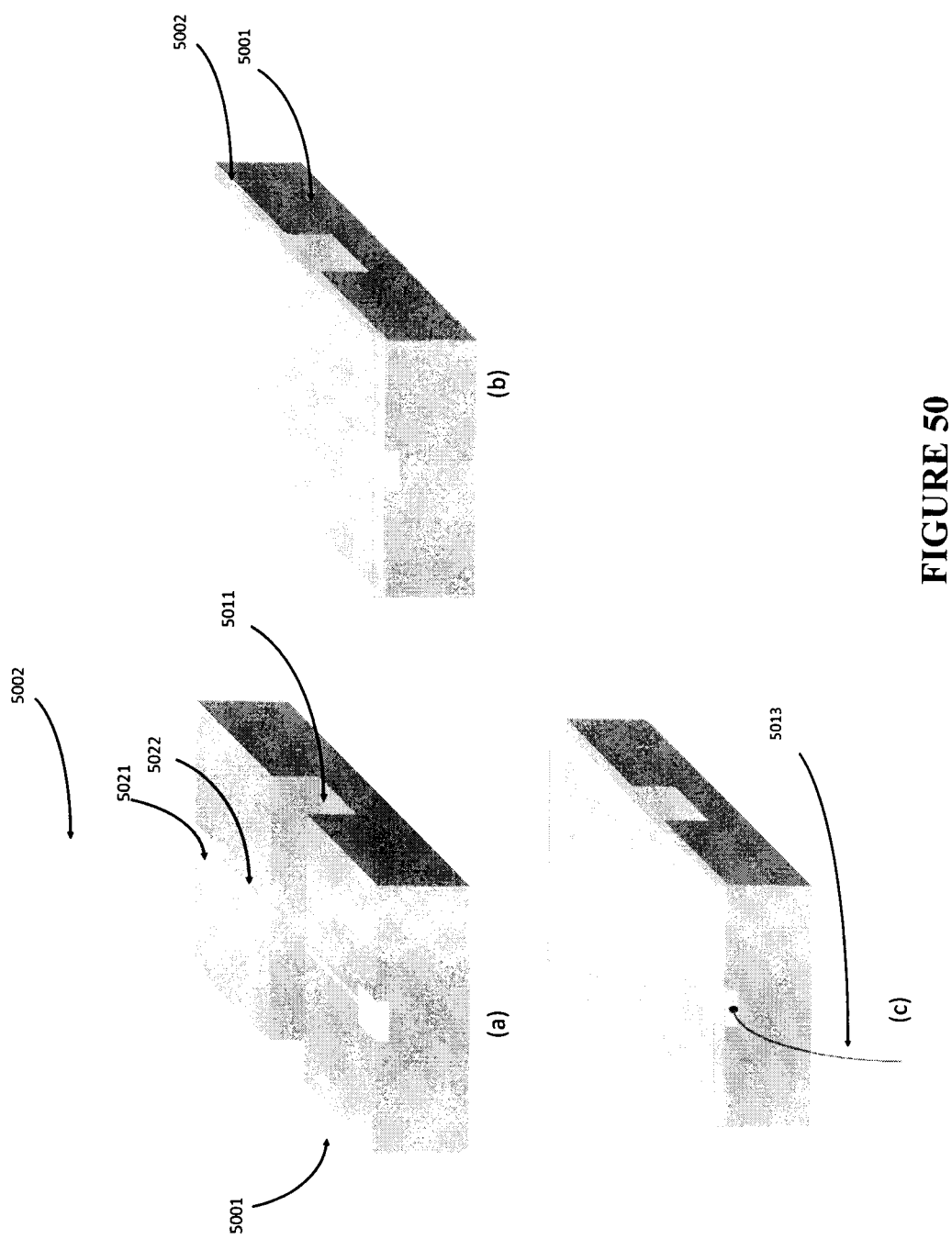
Figure 50:
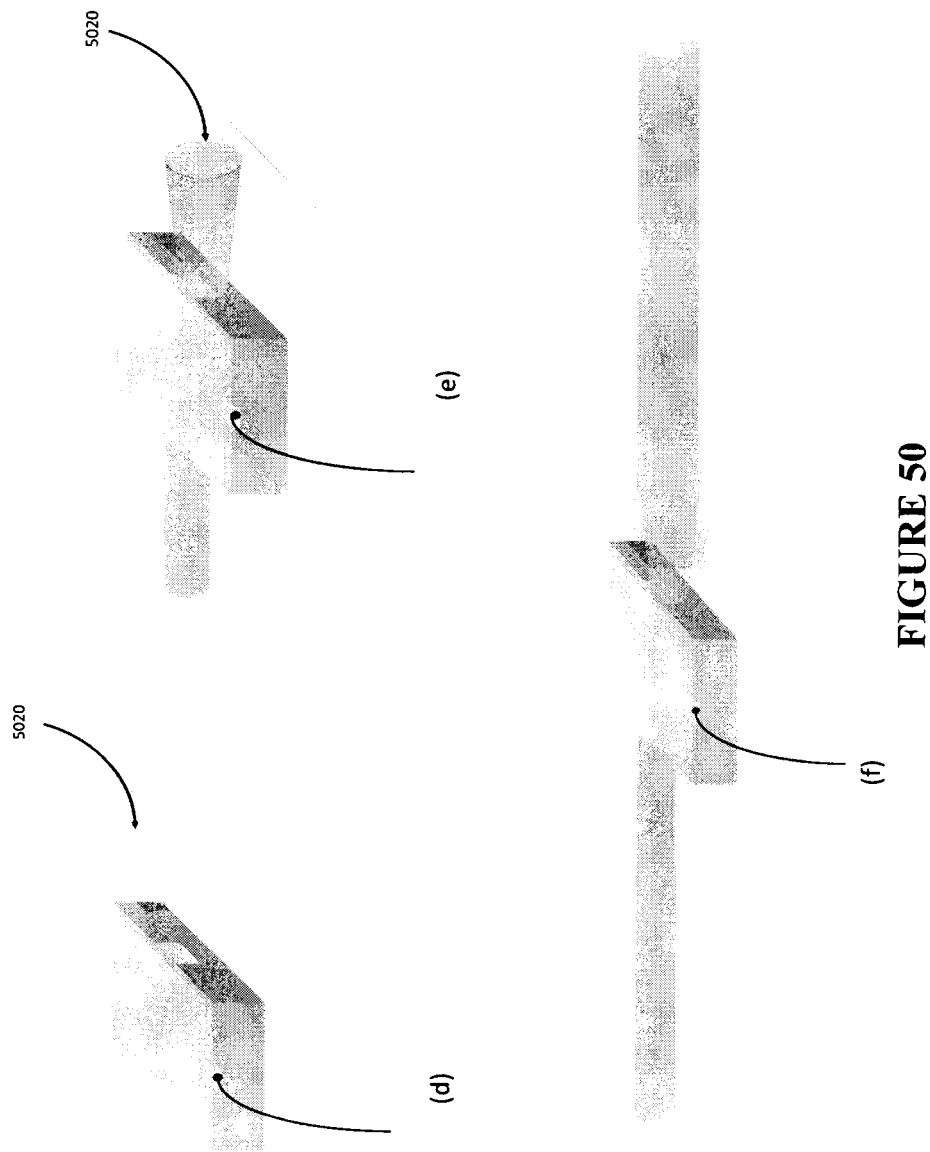

FIG. 50 shows an example of the apparatus of this invention packaged and ready for use.

Figure 51:
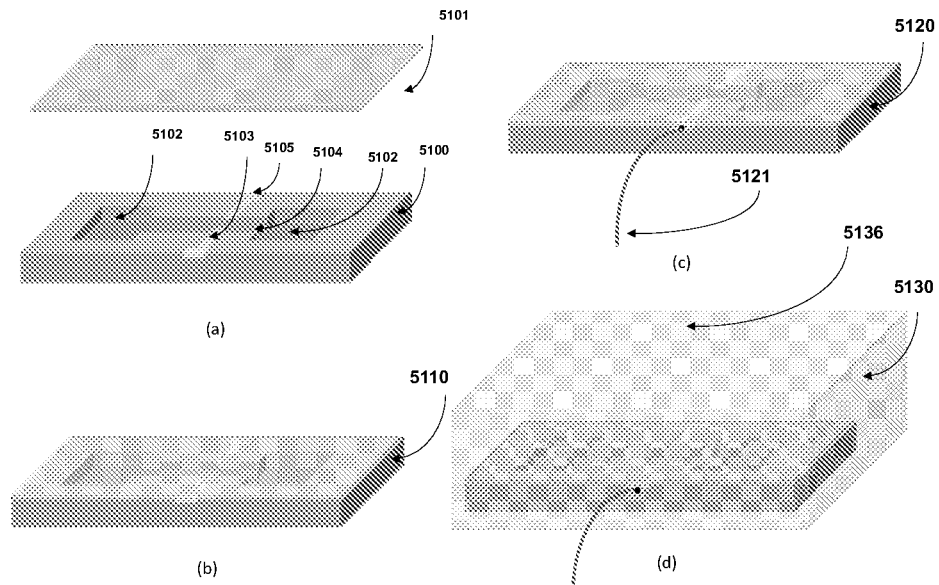
Figure 51:
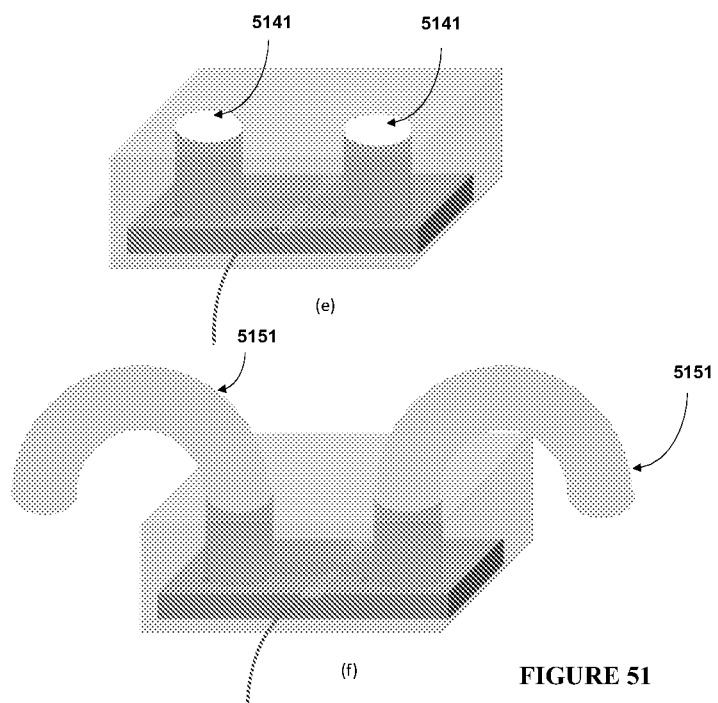

FIG. 51 shows another example of the apparatus of this invention that is packaged and ready for use.

Figure 52:
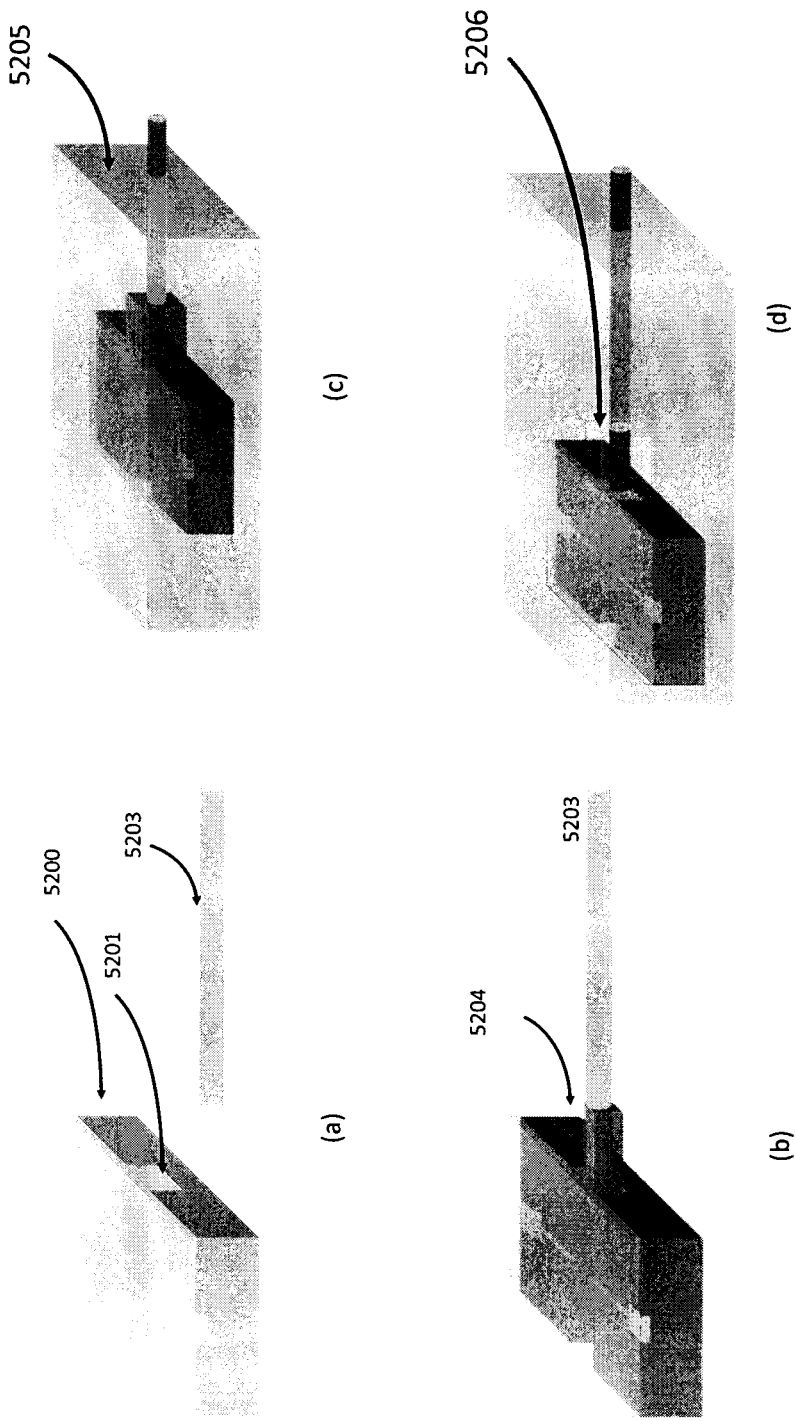

FIG. 52 shows yet another example of the apparatus of this invention that is packaged and ready for use.

Figure 53:
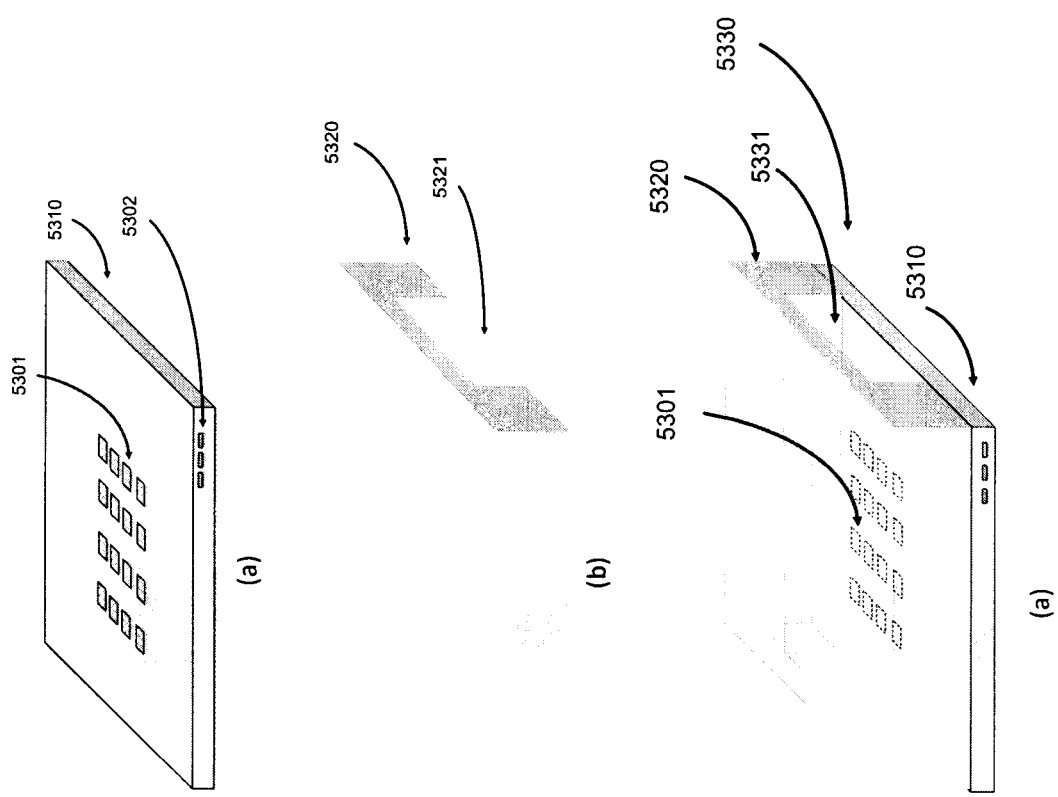

FIG. 53 shows an apparatus of this invention that has a channel (trench) and an array of micro sensors.

Figure 54:
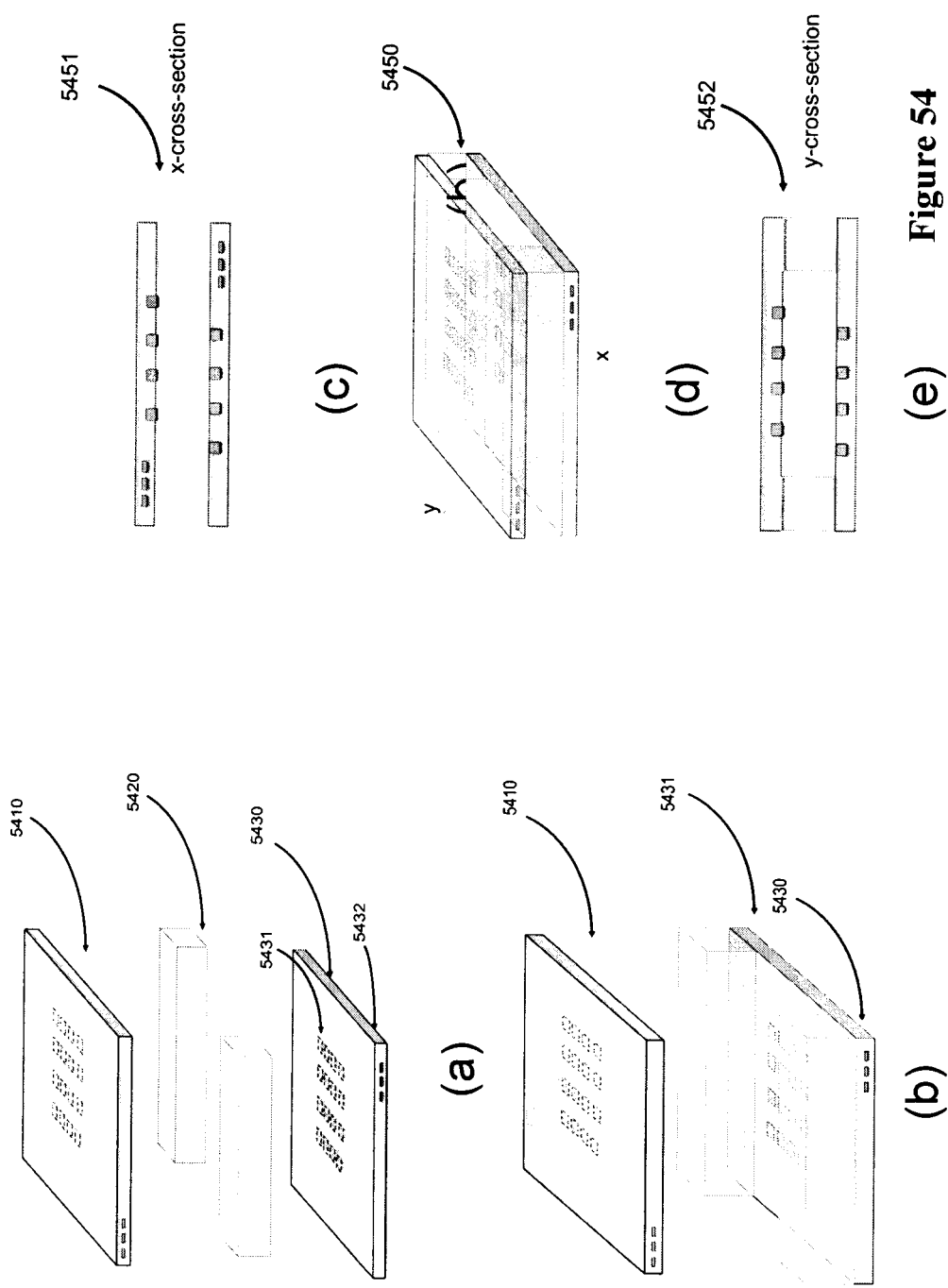

FIG. 54 shows another apparatus of this invention that comprises 2 panels one of which has an array of micro sensors and two micro cylinders.

Figure 55:
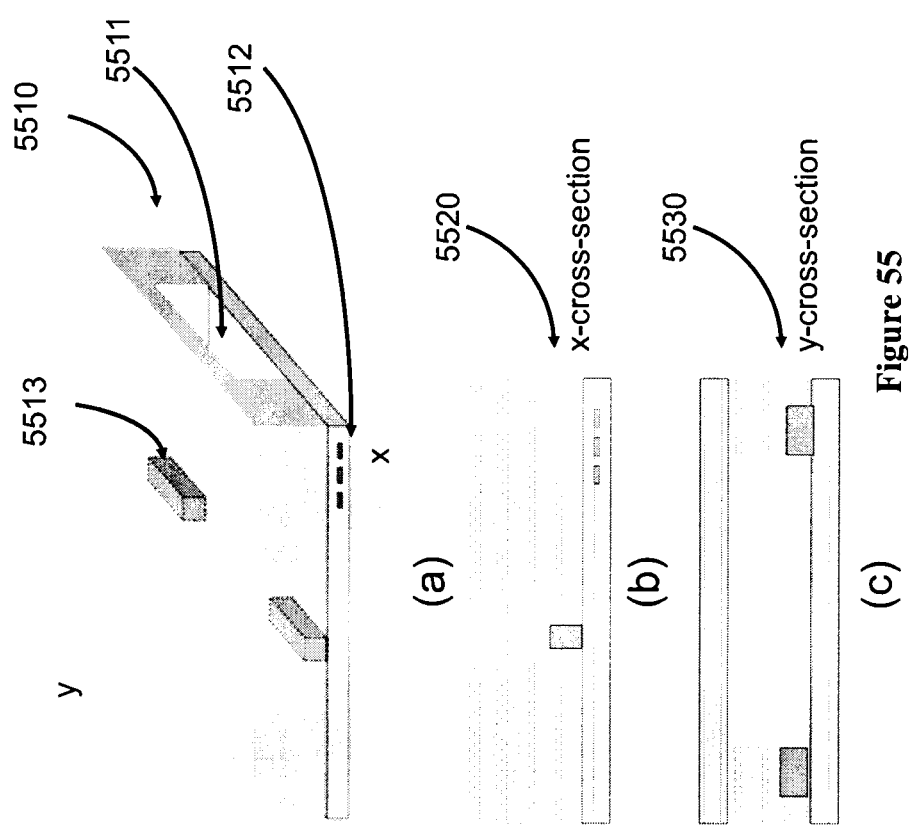

FIG. 55 shows an apparatus of this invention that comprises 2 panels one of which has an array of micro sensors and two micro cylinders both of which have a probing sensor.

Figure 56:
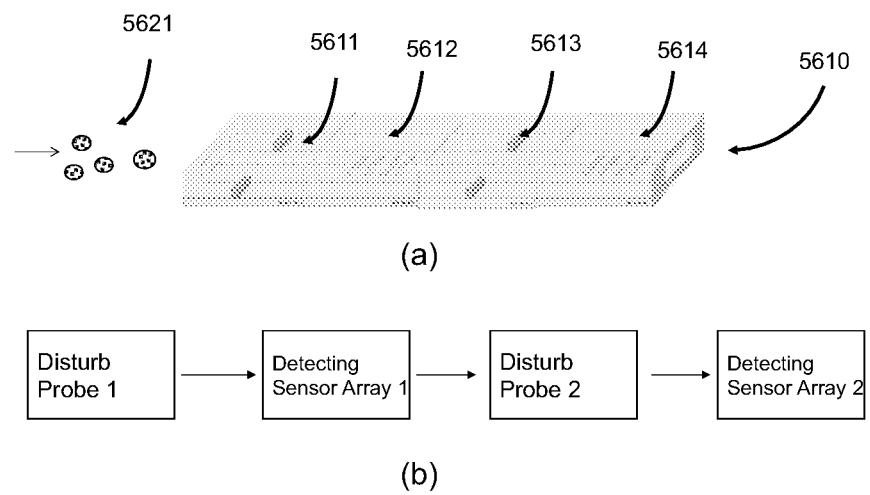

FIG. 56 shows another apparatus of this invention comprising several "sub-devices."

Figure 57:
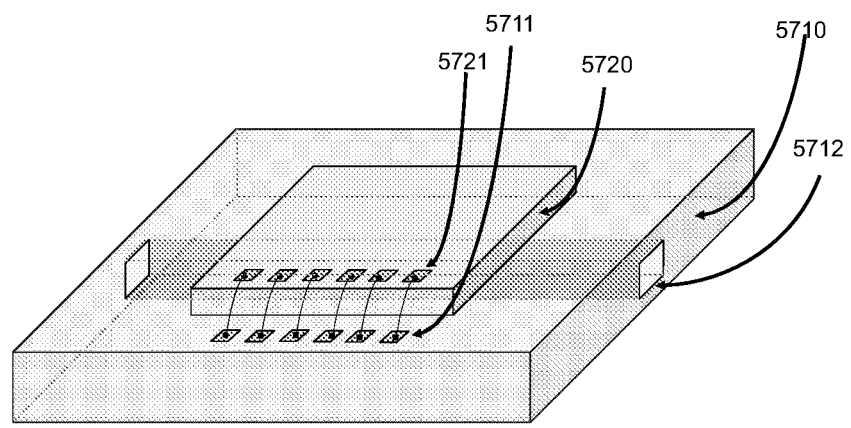

FIG. 57 shows an example of the apparatus of this invention which includes an application specific integrated circuit (ASIC) chip with I/O pads.

Figure 58:
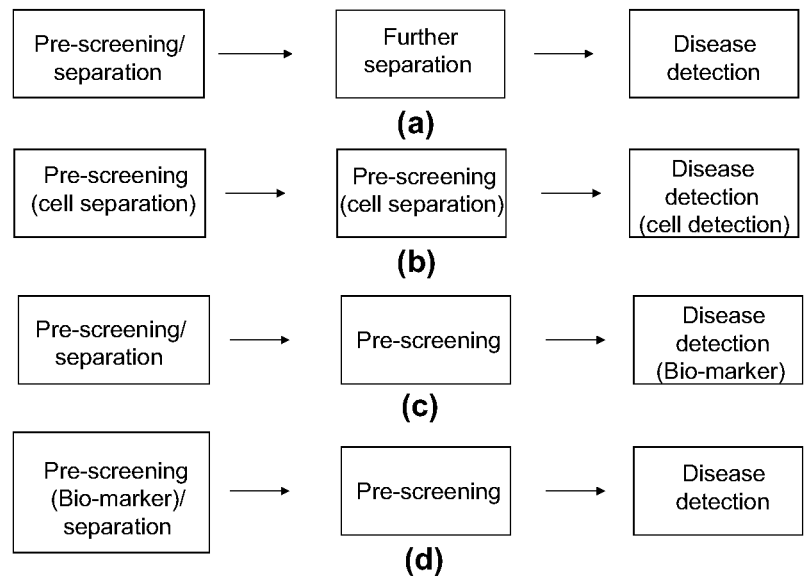
Figure 58:
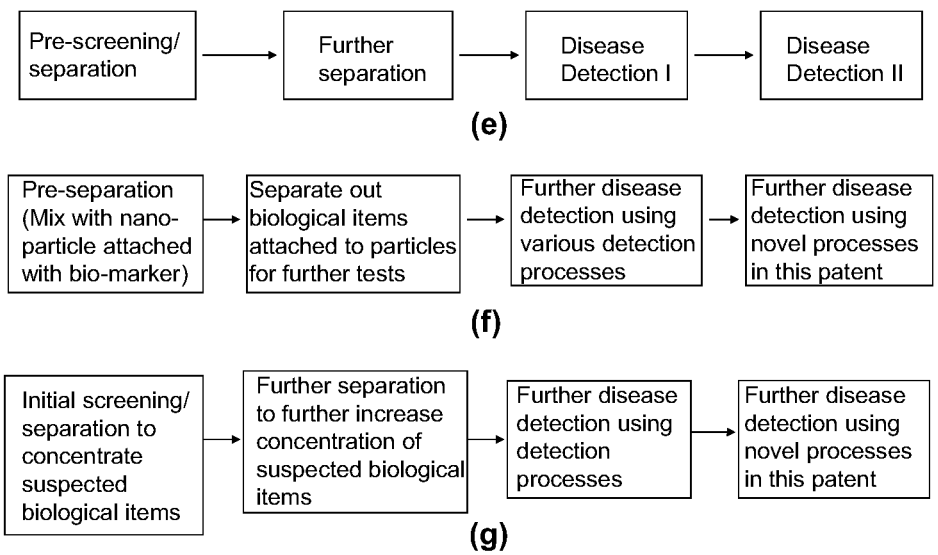

FIG. 58 is a diagram of the underlying principal of the apparatus of this invention which functions by combining various pre-screening and detection methods in unobvious ways.

Figure 59:
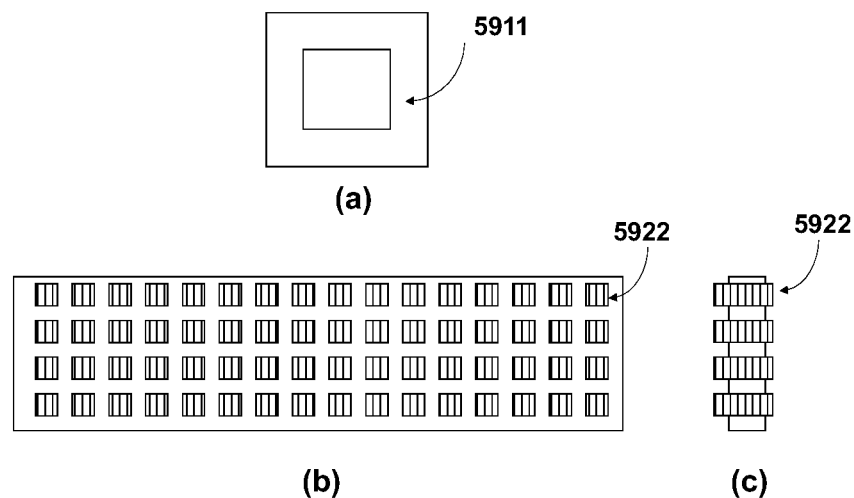

FIG. 59 shows cross-sectional and outside views of a channel into which a biological subject can flow.

Figure 60:
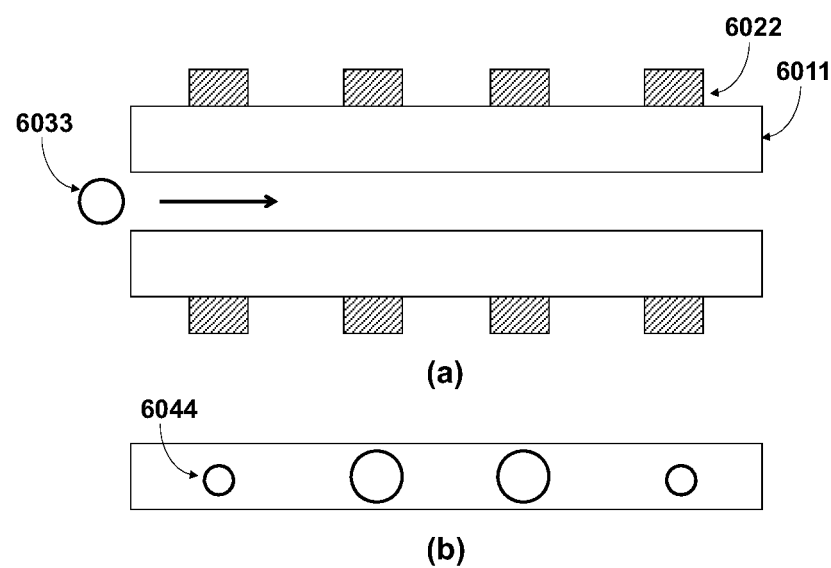
Figure 60:
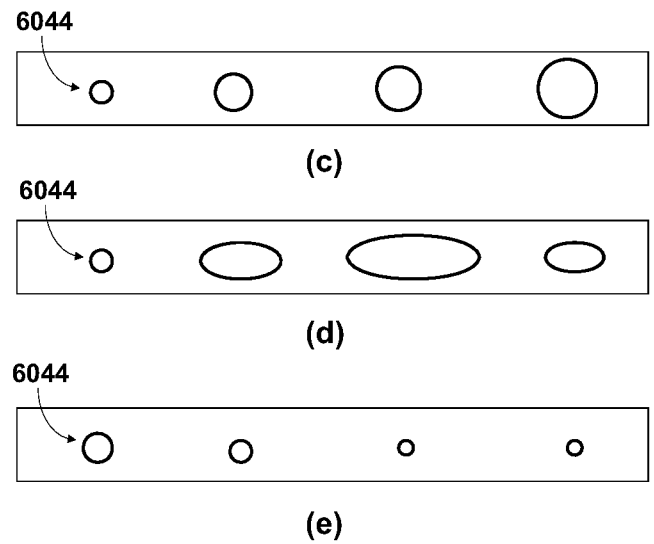

FIG. 60 shows a biological subject to be detected passing through a channel aligned with detectors along its passage in an apparatus of this invention.

Figure 61:
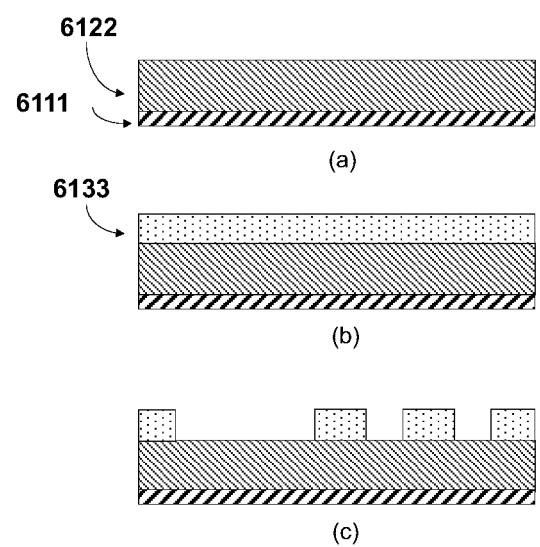
Figure 61:
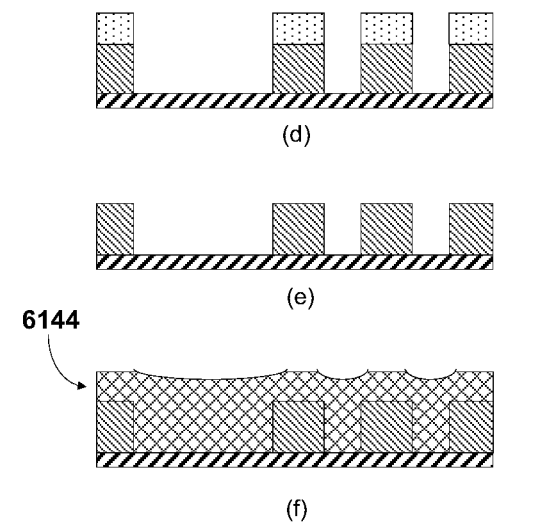
Figure 61:
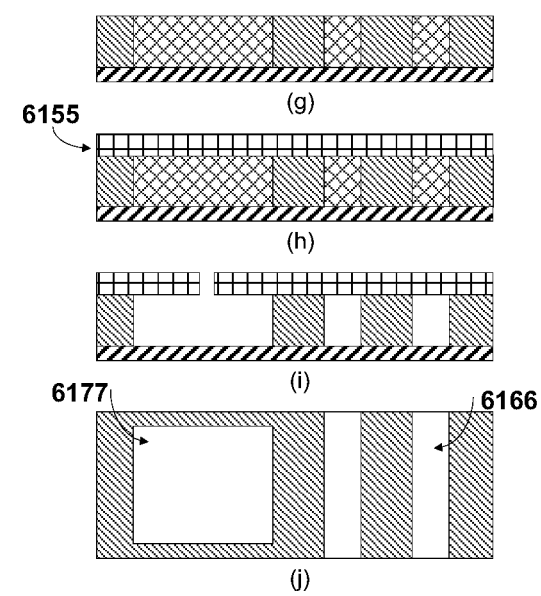
Figure 61:
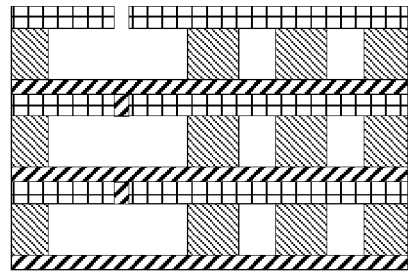
Figure 61:
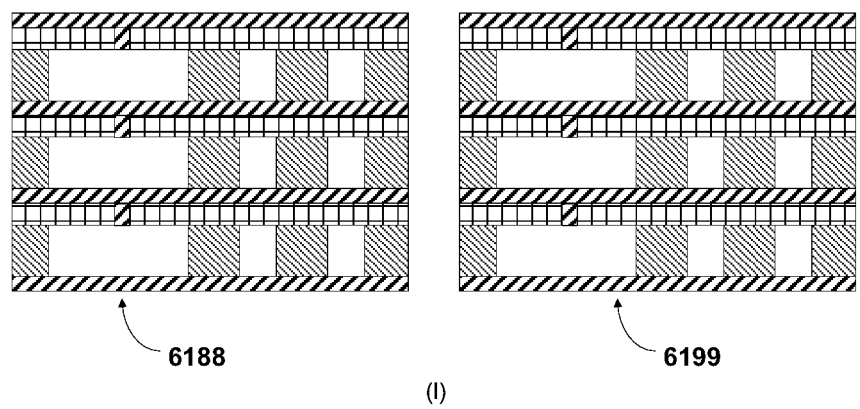

FIG. 61 illustrates a device fabrication process flow and associated device structures.

FIG. 62 is a view of the apparatus of this invention showing one or two sorting units therein.

Figure 63:
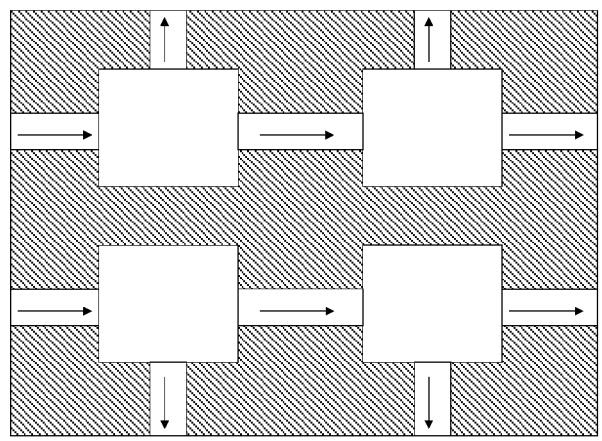

FIG. 63 shows an apparatus of this invention with a high number of desired structures fabricated simultaneously on the same chip.

Figure 64:
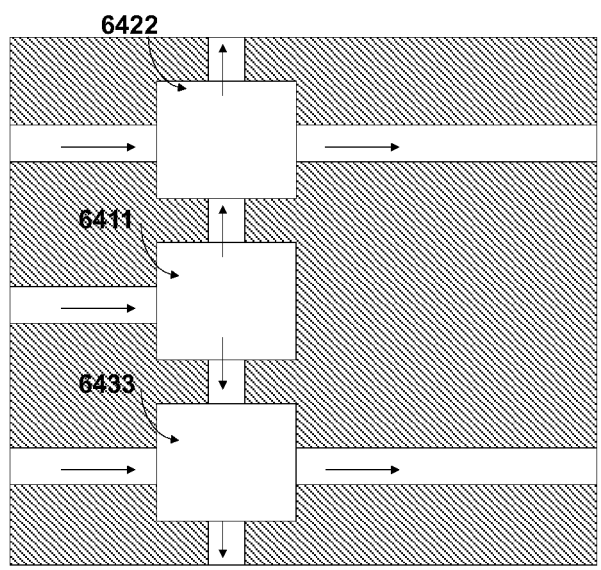

FIG. 64 shows another novel device layout for sorting, screening, separating, probing and detecting diseased biological entities, in which a desired component or multiple components through the middle channel into the middle chamber can play a wide range of roles.

Figure 65:
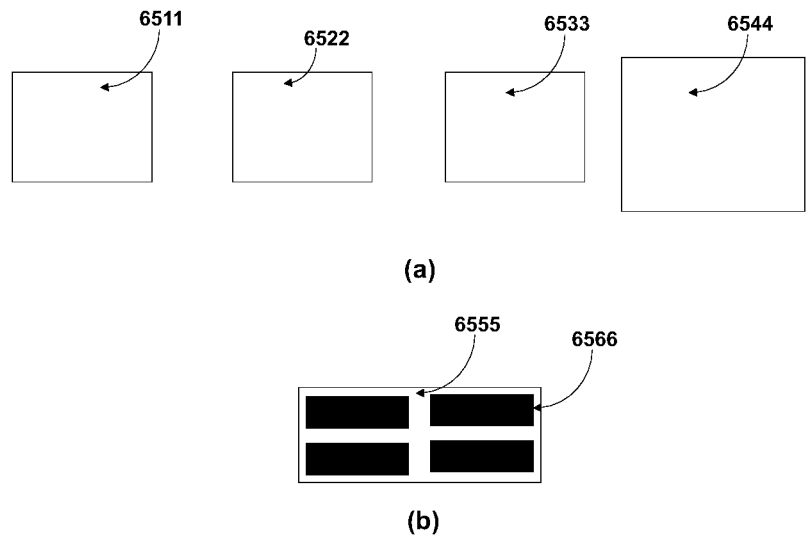

FIG. 65 shows that, compared with multiple stand-alone detection apparatuses, an apparatus of this invention with multiple sub-units of different functions and technologies assembled or integrated has a significantly reduced apparatus volume or size, therefore reduced costs since many common hardware (e.g., a sample handling unit, a sample measurement unit, a data analysis unit, a display, a printer, etc.) can be shared in an integrated apparatus.

Figure 66:
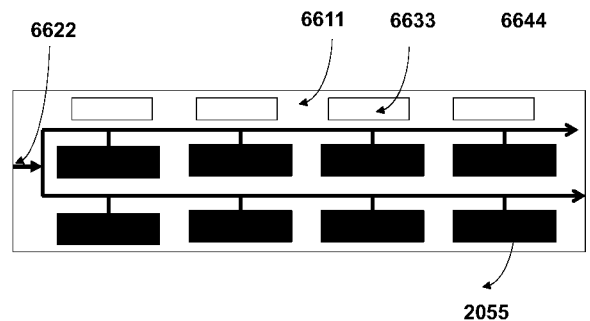

FIG. 66 shows that when multiple sub-units with different functions and technologies are assembled into one apparatus, a more diverse functionality, improved detection functionality, sensitivity, detection versatility, and reduced volume and cost can be achieved, where a number of common utilities including, e.g., input hardware, output hardware, sample handling unit, sample measurement unit, data analysis unit and data display unit can be shared.

DETAILED DESCRIPTION OF THE INVENTION

One aspect of the present invention relates to apparatus for detecting a disease in a biological subject in vivo or in vitro (e.g., human being, an organ, a tissue, or cells in a culture). Each apparatus comprises a delivery system, at least two sub-equipment units, and optionally a central control system. Each sub-equipment is capable of measuring at least a microscopic property of a biological sample. Accordingly, the apparatus of this invention can detect different parameters of the biological subject and provide accuracy, sensitivity, specificity, efficiency, non-invasiveness, practicality, conclusive, and speed in early-stage disease detection at reduced costs. In addition, the apparatus of this invention have some major advantages, such as reducing effective foot print (e.g., defined as function per unit space), reducing space for the medical devices, reducing overall cost, and providing conclusive and effective diagnosis by one device.

The delivery system can be a fluid delivery system. By the constant pressure fluid delivery system, microscopic biological subjects can be delivered onto or into one or more desired sub-equipment units of the apparatus.

As a key component of the apparatus, the micro-device should include means to perform at least the function of addressing, controlling, forcing, receiving, amplifying, or storing information from each probing address. As an example, the apparatus can further include a central control system for controlling the biological subject matter to be transported to one or more desired sub-equipment units and reading and analyzing a detected data from each sub-equipment unit. The central control system includes a controlling circuitry, an addressing unit, an amplifier circuitry, a logic processing circuitry, a memory unit, an application specific chip, a signal transmitter, a signal receiver, or a sensor.

In some embodiments, the fluid delivering system comprises a pressure generator, a pressure regulator, a throttle valve, a pressure gauge, and distributing kits. As examples of these embodiments, the pressure generator can include a motor piston system and a bin containing compressed gas; the pressure regulator (which can consist of multiple regulators) can down-regulate or up-regulate the pressure to a desired value; the pressure gauge feeds back the measured value to the throttle valve which then regulates the pressure to approach the target value.

The biological fluid to be delivered can be a sample of a biological entity to be detected for disease or something not necessarily to be detected for disease. In some embodiments, the fluid to be delivered is liquid (e.g., a blood sample or a lymph sample). The pressure regulator can be a single pressure regulator or multiple pressure regulators which are placed in succession to either down-regulate or up-regulate the pressure to a desired level, particularly when the initial pressure is either too high or too low for a single regulator to adjust to the desired level or a level that is acceptable for an end device or target.

Optionally, the apparatus includes additional features and structures to deliver a second liquid solution containing at least an enzyme, protein, oxidant, reducing agent, catalyst, radio-active component, optical emitting component, or ionic component. This second liquid solution can be added to the sample to be measured before or during sorting of the biological subject sample to be measured, or before or during the measurement (i.e., detection) of the biological subject sample, for the purposes of further enhancing the apparatus' measurement sensitivity.

In some other embodiments, the system controller includes a pre-amplifier, a lock-in amplifier, an electrical meter, a thermal meter, a switching matrix, a system bus, a nonvolatile storage device, a random access memory, a processor, or a user interface. The interface can include a sensor which can be a thermal sensor, a flow meter, an optical sensor, an acoustic detector, a current meter, an electrical sensor, a magnetic sensor, an electro-magnetic sensor, a pH meter, a hardness measurement sensor, an imaging device, a camera, a piezo-electrical sensor, a piezo-photronic sensor, a piezo-electro photronic sensor, an electro-optical sensor, an electro-thermal sensor, a bio-electrical sensor, a bio-marker sensor, a bio-chemical sensor, a chemical sensor, an ion emission sensor, a photo-detector, an x-ray sensor, a radiation material sensor, an electrical sensor, a voltage meter, a thermal sensor, a flow meter, or a piezometer.

In still some other embodiments, apparatus of this invention further include a biological interface, a system controller, a system for reclaiming or treatment medical waste. The reclaiming and treatment of medical waste can be performed by the same system or two different systems.

Another aspect of this invention provides apparatus for interacting with a cell, which include a device for sending a signal to the cell and optionally receiving a response to the signal from the cell.

In some embodiments, the interaction with the cell can be probing, detecting, sorting, communicating with, treating, or modifying with a coded signal that can be a thermal, optical, acoustical, biological, chemical, electro-mechanical, electro-chemical, electro-optical, bio-electro-optical, bio-thermal optical, electro-chemical optical, electro-chemical-mechanical, bio-chemical, bio-mechanical, bio-electro-mechanical, bio-electro-chemical, bio-electro-chemical-mechanical, electric, magnetic, electro-magnetic, physical, or mechanical signal, or a combination thereof.

In some other embodiments, the device or the sub-equipment unit contained in the apparatus can include multiple surfaces coated with one or more elements or combinations of elements, and a control system for releasing the elements. In some instances, the control system can cause release of the elements from the device surface via an energy including but not limited to thermal energy, optical energy, acoustic energy, electrical energy, electro-magnetic energy, magnetic energy, radiation energy, or mechanical energy in a controlled manner. The energy can be in the pulsed form at desired frequencies.

In some other embodiments, the device or the sub-equipment unit contained in the apparatus includes a first component for storing or releasing one element or a combination of elements onto the surface of the cell or into the cell; and a second component for controlling the release of the elements (e.g., a circuitry for controlling the release of the elements). The elements can be a biological component, a chemical compound, ions, catalysts, Ca, C, Cl, Co, Cu, H, I, Fe, Mg, Mn, N, O, P, F, K, Na, S, Zn, or a combination thereof. The signal, pulsed or constant, can be in the form of a released element or combination of elements, and it can be carried in a liquid solution, gas, or a combination thereof. In some instances, the signal can be at a frequency ranging from about $1\times10^{-4}$ Hz to about 100 MHz or ranging from about $1\times10^{-4}$ Hz to about 10 Hz, or at an oscillation concentration ranging from about 1.0 nmol/L to about 10.0 mmol/L. Also, the signal comprises the oscillation of a biological component, a chemical compound, Ca, C, Cl, Co, Cu, H, I, Fe, Mg, Mn, N, O, P, F, K, Na, S, Zn, or a combination thereof, e.g., at desired oscillating frequencies.

In some embodiments, the signal to be sent to the cell can be in the form of oscillating element, compound, or an oscillating density of a biological component, and a response to the signal from the cell is in the form of oscillating element, compound, or an oscillating density of a biological component.

In some embodiments, the device or the sub-equipment unit can be coated with a biological film, e.g., to enhance compatibility between the device and the cell.

In some other embodiments, the device or the sub-equipment unit can include components for generating a signal to be sent to the cell, receiving a response to the signal from the cell, analyzing the response, processing the response, and interfacing between the device and the cell.

Still another aspect of this invention provides devices or sub-equipment units each including a micro-filter, a shutter, a cell counter, a selector, a micro-surgical kit, a timer, and a data processing circuitry. The micro-filter can discriminate abnormal cells by a physical property (e.g., dimension, shape, or velocity), mechanical property, electric property, magnetic property, electro-magnetic, thermal property (e.g., temperature), optical property, acoustical property, biological property, chemical property, electro-chemical property, bio-chemical property, bio-electro-chemical property, bio-electro-mechanical property, or electro-mechanical property. The devices each can also include one or more micro-filters. Each of these micro-filters can be integrated with two cell counters, one of which is installed at the entrance of each filter well, while the other is installed at the exit of each filter well. The shape of the micro-filter's well is rectangle, ellipse, circle, or polygon; and the micro-filter's dimension ranges from about 0.1 µm to about 500 µm or from about 5 um to about 200 um. As used herein, the term "dimension" means the physical or feature size of the filter opening, e.g., diameter, length, width, or height. The filter can be coated with a biological or bio-compatible film, e.g., to enhance compatibility between the device and the cell.

In addition to separation of biological entity by its size and other physical features, the filter can also contain additional features and functions to perform biological entity separation via other properties, which comprise of mechanical property, electric property, magnetic property, electro-magnetic, thermal property (e.g., temperature), optical property, acoustical property, biological property, chemical property, electro-chemical property, bio-chemical property, bio-electro-chemical property, bio-electro-mechanical property, and electro-mechanical property.

In some embodiments of these devices, the shutter sandwiched by two filter membranes can be controlled by a timer (thus time shutter). The timer can be triggered by the cell counter. For instance, when a cell passes through the cell counter of the filter entrance, the clock is triggered to reset the shutter to default position, and moves at a preset speed towards the cell pathway, and the timer records the time as the cell passes through the cell counter at the exit.

Still a further aspect of this invention provides methods for fabricating a micro-device with micro-trench and probe embedded in the micro-trench's sidewalls. A micro-trench is an unclosed tunnel (see, e.g., FIG. 2(i), 2030), which can be coupled with another upended symmetric trench (see, e.g., FIG. 2(k), 2031) to form a closed channel (see, e.g., FIG. 2(l), 2020). The method may include chemical vapor deposition, physical vapor deposition, or atomic layer deposition to deposit various materials on a substrate; patterning the deposited layer(s) utilizing methods comprising of lithography, etch, and chemical mechanical polishing to form desired features (such as a trench); chemical mechanical planarization for surface planarization; chemical cleaning for particle removal; diffusion or ion implantation for doping elements into specific layers; or thermal anneal to reduce the crystal defects and activate diffused ions. An example of such method includes: depositing a first material onto a substrate; depositing a second material onto the first material and patterning the second material by a microelectronic process (e.g., lithography, etch) to form a detecting tip; depositing a third material on the second material and then planarize the third material by a polishing process; depositing a fourth material on the third material and patterning the fourth material first by a microelectronic process (e.g., lithography, etch) and then by a microelectronic process (e.g., another etch) to remove a portion of the third material and optionally a portion of the first material while this etch is typically selective to the second material (lower etch rate for the second material), in which the fourth material serves as a hardmask. A hardmask generally refers to a material (e.g., inorganic dielectric or metallic compound) used in semiconductor processing as an etch mask in lieu of polymer or other organic "soft" materials.

In some embodiments, the method further includes coupling two devices or sub-equipment units that are thus fabricated and symmetric (i.e., a flipped mirror) to form a detecting device with channels. The entrance of each channel can be optionally bell-mouthed, e.g., such that the size of channel's opening end (the entrance) is larger than the channel's body, thereby making it easier for a cell to enter the channel. The shape of each channel's cross-section can be rectangle, ellipse, circle, or polygon. The micro-trenches of the coupled two micro-devices can be aligned by the module of alignment marks designed on the layout of the micro-device. The dimension of the micro-trench can range from about 0.1 um to about 500 um.

Alternatively, the method can also include covering the micro-trench of the micro-device with a flat panel. Such a panel can comprise or be made with silicon, SiGe, $SiO_2$, $Al_2O_3$, quartz, low optical loss glasses, or other optical materials. Examples of other potentially suitable optical materials include acrylate polymer, AgInSbTe, synthetic alexandrite, arsenic triselenide, arsenic trisulfide, barium fluoride, CR-39, cadmium selenide, caesium cadmium chloride, calcite, calcium fluoride, chalcogenide glass, gallium phosphide, GeSbTe, germanium, germanium dioxide, glass code, hydrogen silsesquioxane, Iceland spar, liquid crystal, lithium fluoride, lumicera, METATOY, magnesium fluoride, agnesium oxide, negative index metamaterials, neutron supermirror, phosphor, picarin, poly(methyl methacrylate), polycarbonate, potassium bromide, sapphire, scotophor, spectralon, speculum metal, split-ring resonator, strontium fluoride, yttrium aluminum garnet, yttrium lithium fluoride, yttrium orthovanadate, ZBLAN, zinc selenide, and zinc sulfide.

In other embodiments, the method can further include integrating three or more sub-equipment units or devices thus fabricated to yield an enhanced device with an array of the channels.

Another aspect of this invention relates to a set of novel process flows for fabricating micro-devices (including micro-probes and micro-indentation probes) for their applications in disease detection by measuring microscopic properties of a biological sample. The micro-devices can be integrated into detection apparatus of this invention as sub-equipment units to measure one or more properties at microscopic levels. For example, a cancerous cell may have a different hardness (harder), density (denser), and elasticity than a normal cell.

Another aspect of this invention is to involve in cellular communications and regulate cellular decision or response (such as differentiation, dedifferentiation, cell division and cell death) with fabricated signals generated by the micro-devices disclosed herein. This could be further employed to detect and treat diseases.

To further enhance measurement capabilities, multiple micro-devices can be implemented into a piece of detection apparatus as sub-equipment units employing the time of flight technique, in which at least one probing micro-device and one sensing micro-device placed at a preset, known distance. The probing micro-device can apply a signal (e.g., a voltage, a charge, an electrical field, a laser beam, a thermal pulse, a train of ions, or an acoustic wave) to the biological sample to be measured, and the detection (sensing) micro-device can measure response from or of the biological sample after the sample has traveled a known distance and a desired period of time. For instance, a probing micro-device can apply an electrical charge to a cell first, and then a detection (sensing) micro-device subsequently measures the surface charge after a desired period of time (T) has lapsed and the cell has traveled a certain distance (L).

The micro-devices or the sub-equipment units contained in the apparatus of this invention can have a wide range of designs, structures, functionalities, flexibilities, and applications due to their diverse properties, high degree of flexibilities, and ability of integration, miniaturization, and manufacturing scalability. They include, e.g., a voltage comparator, a four point probe, a calculator, a logic circuitry, a memory unit, a micro cutter, a micro hammer, a micro shield, a micro dye, a micro pin, a micro knife, a micro needle, a micro thread holder, micro tweezers, a micro laser, a micro optical absorber, a micro mirror, a micro wheeler, a micro filter, a micro chopper, a micro shredder, micro pumps, a micro absorber, a micro signal detector, a micro driller, a micro sucker, a micro tester, a micro container, a signal transmitter, a signal generator, a friction sensor, an electrical charge sensor, a temperature sensor, a hardness detector, an acoustic wave generator, an optical wave generator, a heat generator, a micro refrigerator and a charge generator.

Further, it should be noted that advancements in manufacturing technologies have now made fabrications of a wide range of micro-devices and integration of various functions onto the same device highly feasible and cost effective. The typical human cell size is about 10 microns. Using state-of-the-art integrated circuit fabrication techniques, the minimum feature size defined on a micro-device can be as small as 0.1 micron or below. Thus, it is ideal to utilize the disclosed micro-devices for biological applications.

In terms of materials for the micro-devices in the apparatus of this invention, the general principle or consideration is the material's compatibility with a biological entity. Since the time in which a micro-device is in contact with a biological sample (e.g., a cell) may vary, depending on its intended application, a different material or a different combination of materials may be used to make the micro-device. In some special cases, the materials may dissolve in a given pH in a controlled manner and thus may be selected as an appropriate material. Other considerations include cost, simplicity, ease of use and practicality. With the significant advancements in micro fabrication technologies such as integrated circuit manufacturing technology, highly integrated devices with minimum feature size as small as 0.1 micron can now be made cost-effectively and commercially. One good example is the design and fabrication of micro electro mechanical devices (MEMS), which now are being used in a wide variety of applications in the electronics industry and beyond.

Experiments utilizing the apparatus of this invention have been carried out on multiple types of cancer. Good cancer detection results in terms of measurement sensitivity and specificity have been obtained on multiple types of cancer tested, demonstrating validity of the apparatus of this invention for improved ability to detect diseases (e.g., cancers), particularly in their early stages. The experimental results have also shown that multiple cancer types can be detected using the disclosed apparatus, which itself is an improvement over many existing detection apparatus.

Set forth below are several illustrations or examples of apparatus of this invention containing a class of innovative micro-devices that are integrated as sub-equipment units.

Figure 1:
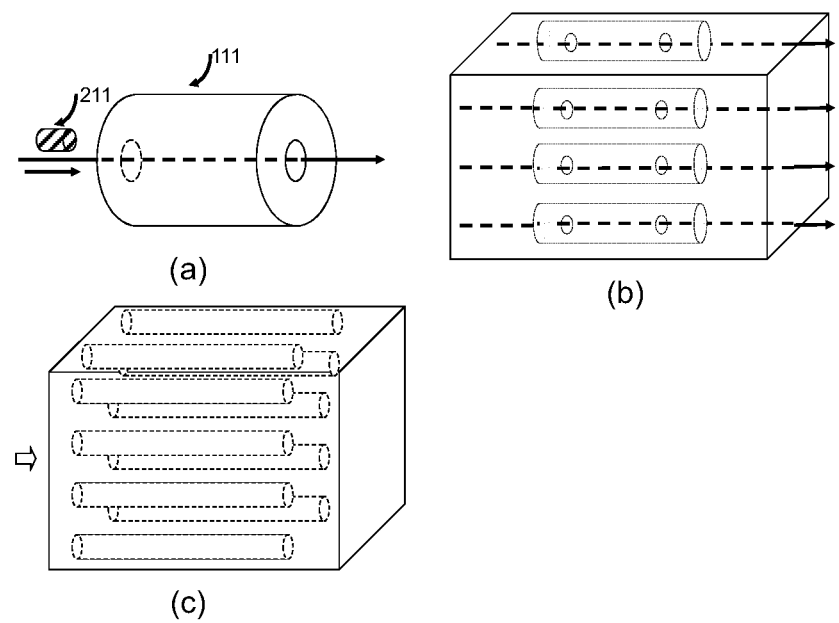
FIG. 1 (*a*) illustrates a set of traditional detection apparatus each of which detects and relies on a single detection technology.

FIG. 1 (a) illustrates a set of traditional detection apparatus each of which relies on a single detection technology. As shown in FIG. 1 (a), current diagnosis devices detect a disease on a narrow focus and typically by one single technology (e.g., x-ray machine or NMR machine).

FIGS. 1 (b) and (c) are an illustration of a detection apparatus of this invention where multiple sub-equipment units are integrated into one piece of apparatus. As a result, the novel apparatus has a smaller size comparing to traditional devices.

Figure 2:
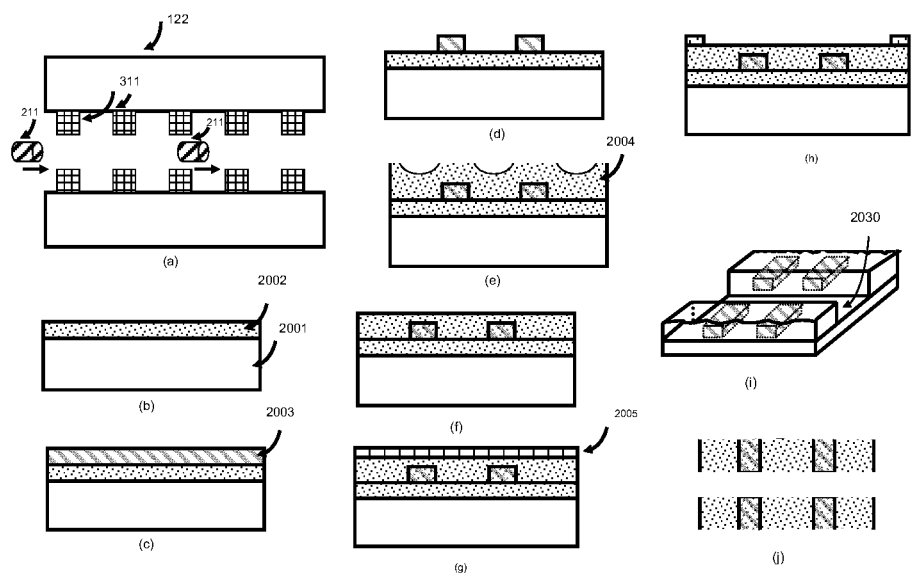
FIG. 2 is a schematic illustration of a detection apparatus of this invention which comprises multiple sub-equipment units, a delivery system, and a central control system.
Figure 2:
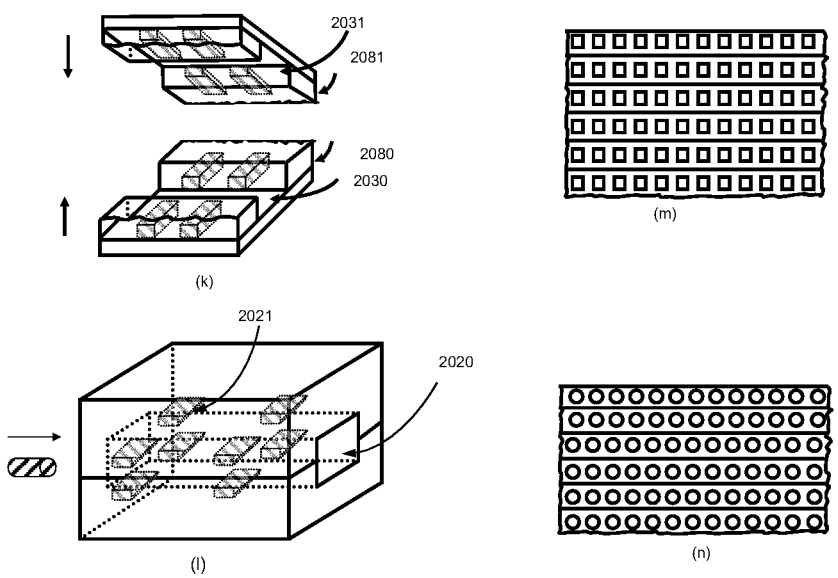

FIG. 2 is a schematic illustration of a detection apparatus of this invention which comprises multiple sub-equipment units, a delivery system, and a central control system. The central control system comprises multiple processing units each of which can be a computer, data analysis unit, or display unit. The central control system is interacted with and used by multiple sub-equipment units. This resource sharing process can effectively reduce cost and size of the apparatus. The biological subject (e.g. a fluid sample) can flows to each sub-equipment units via the delivery system. The delivery system can also transport the biological subject to one or more desired sub-equipments for specific diagnosis purposes.

To enhance detection speed and sensitivity, a large number of micro-devices can be integrated into a single apparatus of this invention. Each micro-device can be a independent sub-equipment unit in the apparatus. To achieve the above requirements, the detection apparatus should be optimized with its surface area maximized to contact the biological sample and with large number of micro-devices integrated on the maximized surface.

Figure 3:
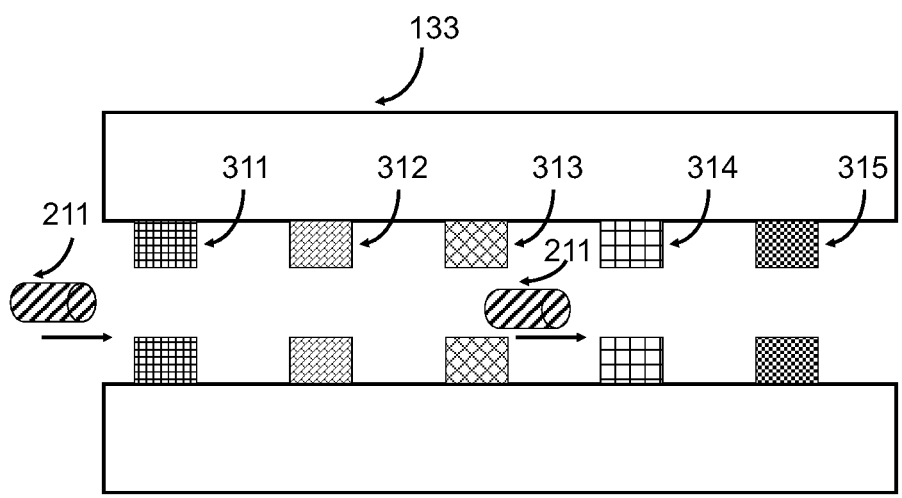
FIG. 3 is a perspective illustration of a detection apparatus of this invention in which a biological sample placed in it or moving through it can be tested.

Instead of measuring a single property of a biological subject for disease diagnosis, various micro-devices can be integrated into a detection apparatus to detect multiple properties. Various micro-devices can constitute different sub-equipment units. FIG. 3 is a perspective, cross-sectional illustration of a disease detection apparatus of this invention 133 with multiple micro-devices 311, 312, 313, 314, and 315, of different detection probes in which a sample 211 such as a blood sample placed in it or moving through it can be tested for multiple properties including but not limited to mechanical properties (e.g., density, hardness and adhesion), thermal properties (e.g., temperature), biological properties, chemical properties (e.g., pH), physical properties, acoustical properties, electrical properties (e.g., surface charge, surface potential, and impedance), magnetic properties, electromagnetic properties, and optical properties.

As illustrated herein, it is desirable to optimize the detection apparatus design to maximize measurement surface area, since the greater the surface area, the greater number of micro-devices that can be placed on the detection apparatus to simultaneously measure the sample, thereby increasing detection speed and also minimizing the amount of sample needed for the test.

Figure 4:
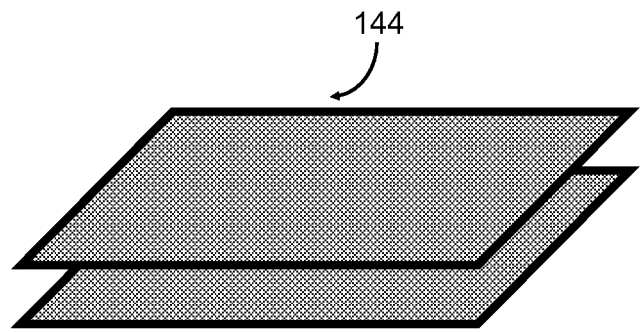
FIG. 4 illustrates an apparatus of the present invention which comprises two slabs each of which is fabricated with one or more detection or probing units.

FIG. 4 is a perspective illustration of an apparatus or a sub-equipment unit of this invention. It includes two slabs separated by a narrow spacing with a sample such as a blood sample to be measured placed between the slabs, with multiple micro-devices placed at the inner surfaces of the slabs to measure one or more properties of the sample at microscopic levels.

Figure 5:
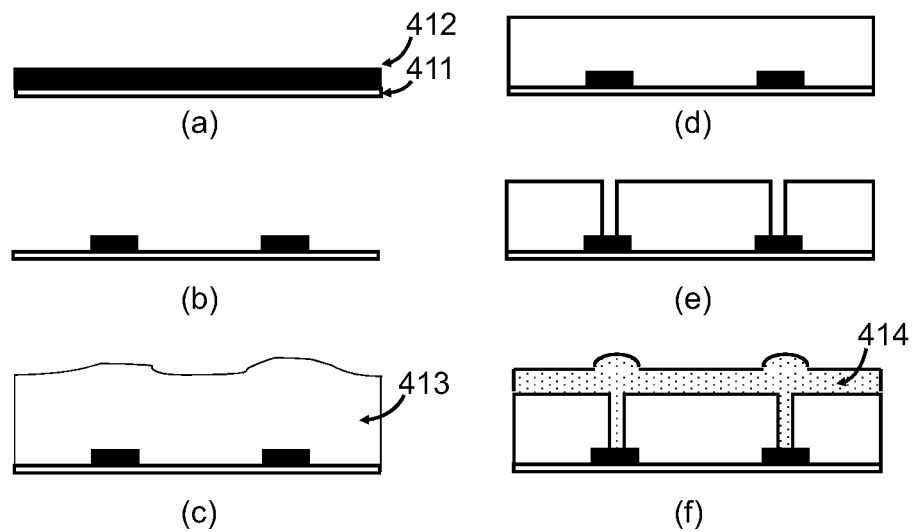
FIG. 5 illustrates a novel process flow for fabricating a detection apparatus of this invention utilizing microelectronics technologies.
Figure 5:
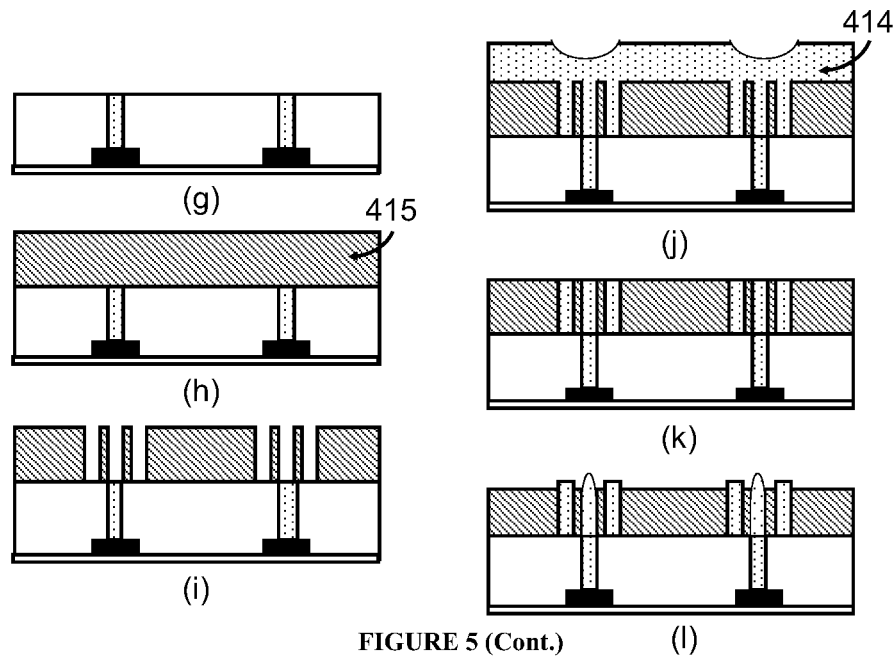

Yet another aspect of this invention relates to a set of novel fabrication process flows for making micro-devices or sub-equipment units for disease detection purposes. FIG. 5 illustrates a novel process flow for fabricating a disease detection apparatus utilizing microelectronics technologies and processes. First, a material 412 is deposited on a substrate 411 (FIG. 5(a)). It is then patterned by photolithography and etching processes (FIG. 5(b)). Following the deposition, material 413 is planarized using chemical mechanical polishing as shown in FIG. 5(d). Recessed areas, in the form of hole pattern, are next formed in material 413 using photolithography and etch processes, as shown in FIG. 7(e), followed by the deposition of material 414 (FIG. 5(f)). Material 414 above the surface of material 413 is removed by chemical mechanical polishing (FIG. 5(g), followed by deposition of material 415. Material 415 is next patterned using photolithography and etching processes (FIG. 5(i)). Material 414 is next deposited and its excess material above its substrate 415 is removed by chemical mechanical polishing (FIGS. 5(j) and (k)). Finally, a light etch or short chemical mechanical polishing to material 415 is carried out to recess material 415, selective to material 414 (FIG. 5(l)), resulting in slight protruding of material 414. Material 412 can be a piezo-electrical material. When a voltage is applied to it in the right direction, it will expand and push up, resulting in upward motion in middle tip in material 414. Thus, a micro-device with two probes capable of measuring a range of properties (including mechanical and electrical properties) of biological samples is fabricated, using the above novel fabrication process flow.

Figure 6:
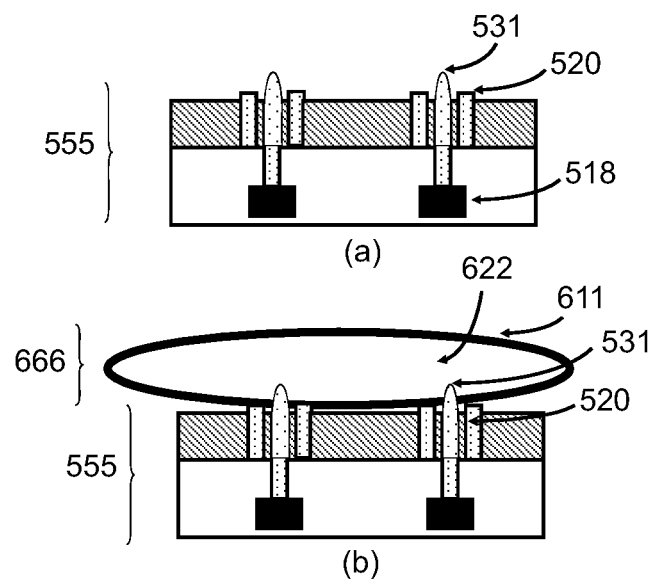
FIG. 6 is a perspective illustration of a detection apparatus fabricated by a method of this invention. The apparatus is capable of probing a single cell and measuring its microscopic properties.

Detection apparatus integrated with micro-devices disclosed in this application is fully capable of detecting pre-chosen properties on a single cell, a single DNA, a single RNA, or an individual, small sized biological matter level. FIG. 6 is a perspective illustration of a micro-device 555 fabricated by a novel process flow disclosed in this patent application (e.g., novel process flow illustrated in FIG. 5 above) and how such a device is capable of probing a single cell 666 and measuring the cell for collecting intended parameters. FIG. 6(a) illustrated a perspective, cross-section of a micro-device 555 with a pair of micro probes 531 and 520, where micro probe 531 is in the form of a tip and micro probe 520 is in the form of a ring. Both of micro probes 531 and 520 can be conductive and they can serve as a pair of probes to measure electrical properties of a biological sample. Micro probe 531 is in contact with a base 518 which can be a piezo-electrical material. When a voltage is applied to the base 518 made of a piezo-electrical material, the base 518 can expand and push micro probe tip 531 upward, which can be useful in measuring various properties of a biological sample such as a single cell. In FIG. 8(b), micro-device 555 is shown to measure a single cell 666, using probe tip 531 penetrating through cell membrane 611 and into the cell's inner space 622, while probe ring 520 making contact with cell membrane 611 at the outside surface of the membrane. This way, the micro-device 555 can make various measurements on the cell, including its electrical properties (e.g., electrical potential, current across the cell membrane, surface charge on the membrane, and impedance), mechanical properties (e.g., hardness when probe tip 531 is designed as a micro-indentation probe), thermal properties (e.g., temperature), physical properties, and chemical properties (e.g., pH).

In another further aspect, the invention provides the design, integration, and fabrication process flow of micro-devices capable of making highly sensitive and advanced measurements on very weak signals in biological systems for disease detection under complicated environment with very weak signal and relatively high noise background. Those novel capabilities using the class of micro-devices disclosed in this invention for disease detection include but not limited to making dynamic measurements, real time measurements (such as time of flight measurements, and combination of using probe signal and detecting response signal), phase lock-in technique to reduce background noise, and 4-point probe techniques to measure very weak signals, and unique and novel probes to measure various electronic, electromagnetic and magnetic properties of biological samples at the single cell (e.g., a telomere of DNA or chromosome), single molecule (e.g., DNA, RNA, or protein), single biological subject (e.g., virus) level.

For example, in a time of flight approach to obtain dynamic information on the biological sample (e.g., a cell, a substructure of a cell, a DNA, a RNA, or a virus), a first micro-device is first used to send a signal to perturb the biological subject to be diagnosed, and then a second micro-device is employed to accurately measure the response from the biological subject. In one embodiment, the first micro-device and the second micro-device are positioned with a desired or pre-determined distance L apart, with a biological subject to be measured flowing from the first micro-device towards the second micro-device. When the biological subject passes the first micro-device, the first micro-device sends a signal to the passing biological subject, and then the second micro-device detects the response or retention of the perturbation signal on the biological subject. From the distance between the two micro-devices, time interval, the nature of perturbation by the first micro-device, and measured changes on the biological subject during the time of flight, microscopic and dynamic properties of the biological subject can be obtained. In another embodiment, a first micro-device is used to probe the biological subject by applying a signal (e.g., an electronic charge) and the response from the biological subject is detected by a second micro-device as a function of time.

Figure 7:
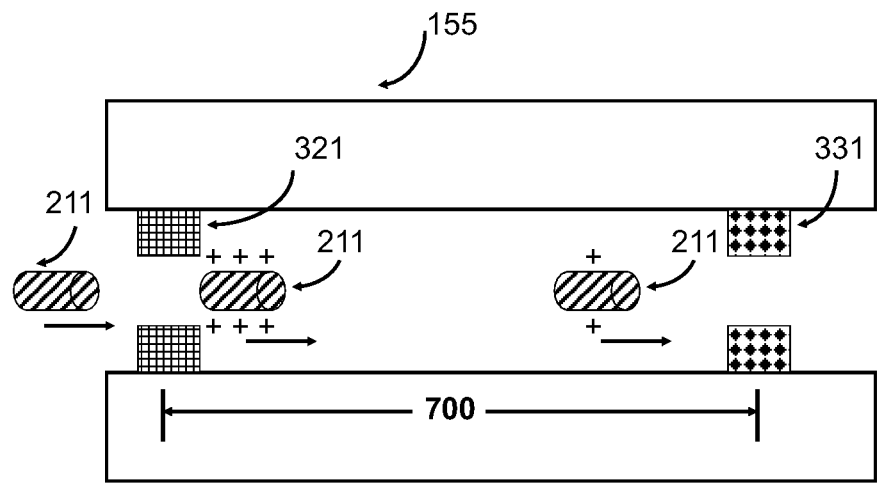
FIG. 7 is a perspective, cross-sectional illustration of a detection apparatus of this invention with multiple micro-devices placed at a desired distance for time of flight measurements with enhanced sensitivity, specificity, and speed, including time dependent or dynamic information.

To further increase detection sensitivity, a novel detection process for disease detection is used, in which time of flight technique is employed. FIG. 7 is a perspective, cross-sectional illustration of detection apparatus 155 with multiple micro-devices 321 and 331 placed at a desired distance 700 for time of flight measurements to attain dynamic information on biological sample 211 (e.g., a cell) with enhanced measurement sensitivity, specificity, and speed. In this time of flight measurement, one or more properties of the biological sample 211 are first measured when the sample 211 passes the first micro-device 321. The same properties are then measured again when the sample 211 passes the second micro-device 331 after it has traveled the distance 700. The change in properties of sample 211 from at micro-device 321 to at micro-device 331 indicates how it reacts with its surrounding environment (e.g., a particular biological environment) during that period. It may also reveal information and provide insight on how its properties evolve with time. Alternatively, in the arrangement shown in FIG. 7, micro-device 321 could be used first as a probe to apply a probe signal (e.g., an electrical charge) to sample 211 as the sample passes the micro-device 321. Subsequently, the response of the sample to the probe signal can be detected by micro-device 331 as the sample passes it (e.g., change in the electrical charge on the sample during the flight). Measurements on biological sample 211 can be done via contact or non-contact measurements. In one embodiment, an array of micro-devices can be deployed at a desired spacing to measure properties of the biological subject over time.

The utilization of micro-devices (e.g., made by using the fabrication process flows of this invention) as discussed above and illustrated in FIG. 7 can be helpful for detecting a set of new, microscopic properties of a biological sample (e.g., a cell, a cell substructure, or a biological molecule such as DNA or RNA or protein) that have not been considered in existing detection technologies. Such microscopic properties can be thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, electrical, magnetic, electromagnetic, physical, or mechanical properties, or a combination thereof, of a biological sample that is a single biological subject (such as a cell, a cell substructure, a biological molecule—e.g., DNA, RNA, or protein—or a sample of a tissue or organ). It is known that biological matters includes from basic bonding such as OH, CO, and CH bonding, to complex, three dimensional structures such as DNA and RNA. Some of them have a unique signature in terms of its electronic configuration. Some of them may have unique thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, electrical, magnetic, electromagnetic, physical, or mechanical properties and configurations, or a combination thereof. Normal biological subject and diseased biological subject may carry different signatures with respective to the above said properties. However, none of the above stated parameters or properties have been routinely used as a disease detection property. Using a disease detection apparatus including one or more apparatus of this invention, those properties can be detected, measured, and utilized as useful signals for disease detection, particularly for early stage detection of serious diseases such as cancer.

Figure 8:
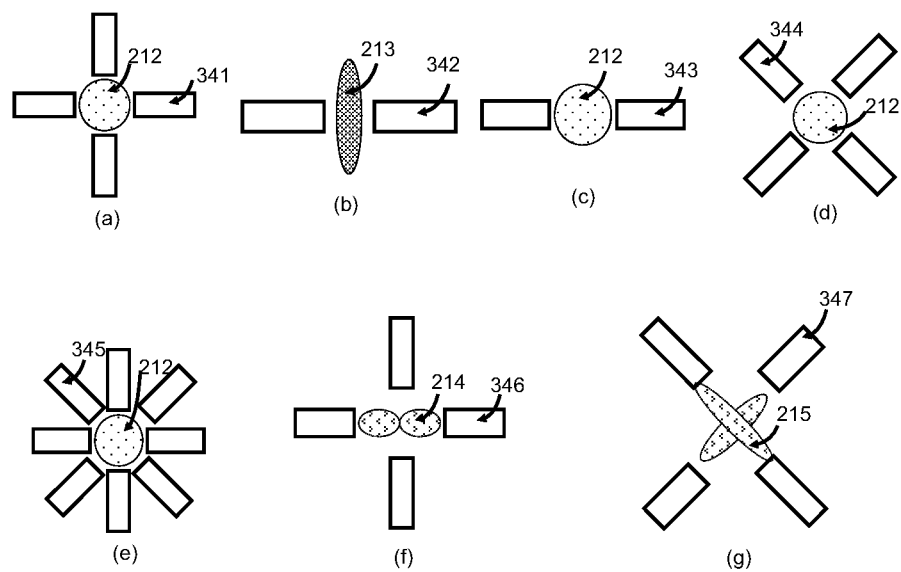
FIG. 8 is a perspective illustration of a novel set of microscopic probes, included in a detection apparatus of this invention, for detecting various electronic or magnetic states, configurations, or other properties of a biological sample (e.g., a cell).

FIG. 8 is a perspective illustration of a novel set of microscopic probes 341, 342, 343, 344, 345, 346, and 347 designed and configured to detect various electronic, magnetic, or electromagnetic states, configurations, or other properties at microscopic level on biological samples 212, 213, 214, and 215, which can be a single cell, DNA, RNA, and tissue or sample. As an example, in terms of measuring electronic properties, the shapes of biological samples 212, 213, 214, and 215 in FIG. 10 may represent electronic monopole (sample 212), dipole (samples 213 and 214), and quadruple (sample 215). The micro-devices 341, 342, 343, 344, 345, 346, and 347 are optimized to maximize measurement sensitivity of those said parameters including but not limited to electronic states, electronic charge, electronic cloud distribution, electrical field, and magnetic and electromagnetic properties, and the micro-devices can be designed and arranged in three dimensional configurations. For some diseases such as cancer, it is likely that electronic states and corresponding electronic properties differ between normal and cancerous cells, DNA, RNA, and tissue. Therefore, by measuring electronic, magnetic and electromagnetic properties at microscopic levels including at cell, DNA, and RNA levels, disease detection sensitivity and specificity can be improved.

In addition to the above examples in measuring electrical properties (e.g., charge, electronic states, electronic charge, electronic cloud distribution, electrical field, current, and electrical potential, and impedance), mechanical properties (e.g., hardness, density, shear strength, and fracture strength) and chemical properties (e.g., pH) in a single cell, and in FIG. 8 for measuring electrical, magnetic or electromagnetic states or configurations of biological samples at cell and biological molecular (e.g., DNA, RNA, and protein) levels, other micro-devices are disclosed in this application for sensitive electrical measurements.

Figure 9:
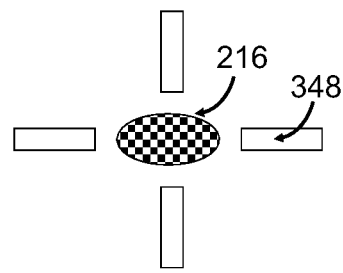
FIG. 9 is a perspective illustration of a novel four-point probe, included in a detection apparatus of this invention, for detecting weak electronic signal in a biological sample (e.g., a cell).

FIG. 9 is a perspective illustration of a four-point probe for detecting weak electronic signal in a biological sample such as a cell, where a four point probe 348 is designed to measure electrical properties (impedance and weak electrical current) of a biological sample 216.

One of the key aspects of this invention is the design and fabrication process flows of micro-devices and methods of use the micro-devices for catching and/or measuring biological subjects (e.g., cells, cell substructures, DNA, and RNA) at microscopic levels and in three dimensional space, in which the micro-devices have micro-probes arranged in three dimensional manner with feature sizes as small as a cell, DNA, or RNA, and capable of trapping, sorting, probing, measuring, and modifying biological subjects. Such micro-devices can be fabricated using state-of-the-art microelectronics processing techniques such as those used in fabricating integrated circuits. Using thin film deposition technologies such as molecular epitaxy beam (MEB) and atomic layer deposition (ALD), film thickness as thin as a few monolayers can be achieved (e.g., 4 A to 10 A). Further, using electron beam or x-ray lithography, device feature size on the order of nanometers can be obtained, making micro-device capable of trapping, probing, measuring, and modifying a biological subject (e.g., a single cell, a single DNA or RNA molecule) possible.

Figure 10:
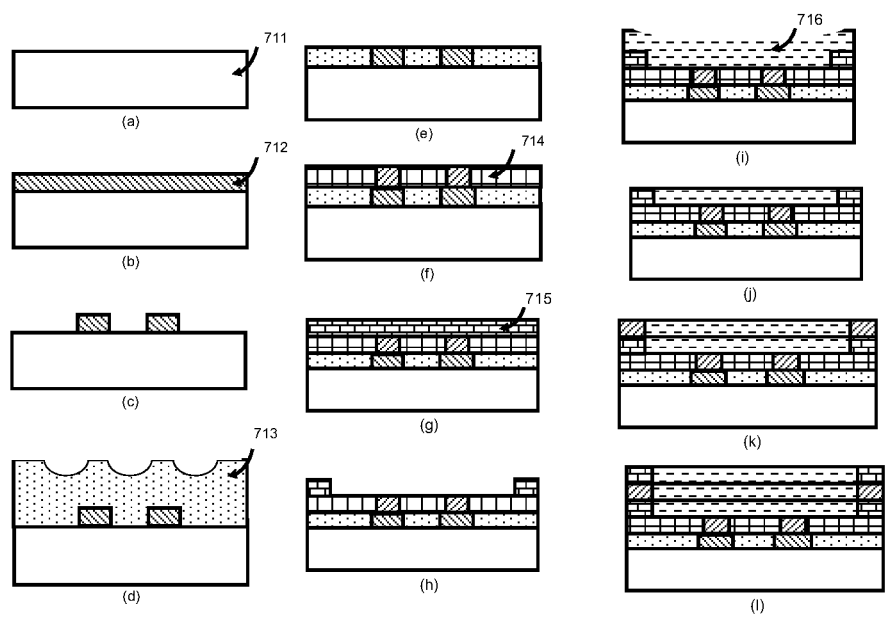
FIG. 10 illustrates a process flow for fabricating some apparatus of this invention.
Figure 10:
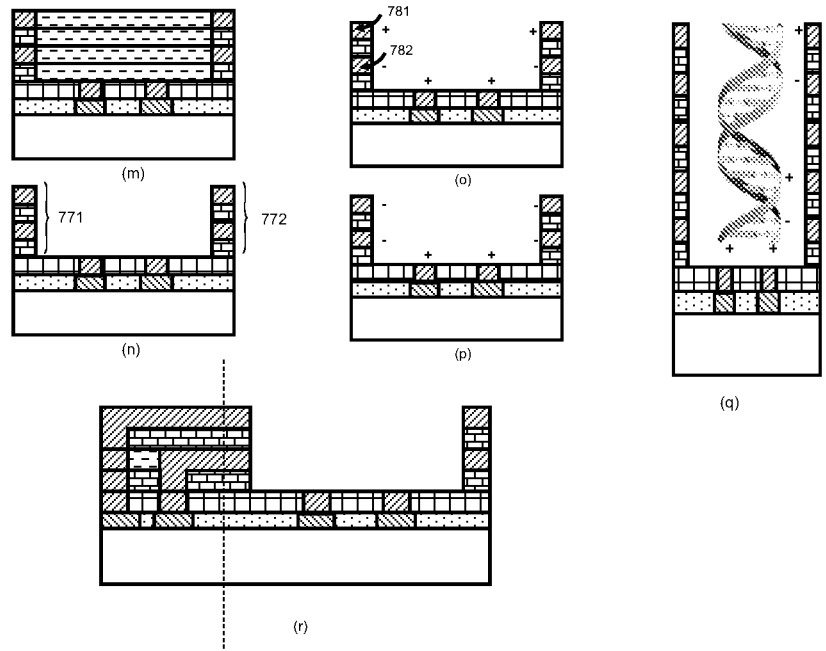

FIG. 10 illustrates a process flow of this invention for fabricating micro-devices for trapping, sorting, probing, measuring, and modifying biological subjects (e.g., a single cell, a DNA or RNA molecule). In this process flow, microelectronics processes are utilized to fabricate micro-devices designed to achieve the above stated unique functions. Specifically, a first material 712 (typically a conducting material) is first deposited on a substrate 711 (FIG. 10(*a*) and FIG. 10(*b*)). The first material 712 is subsequently patterned by using lithography and etch processes (FIG. 10(*c*)). A second material 713 is then deposited and planarized using chemical mechanical polishing process to remove overburden of the second material 713 above the first material 712 (as shown in FIG. 10(*e*)). Another layer of material 714 is deposited and patterned, followed by deposition and planarization by chemical mechanical polishing of another layer of 712 (FIG. 10(*f*)). Next, a third material 715 is deposited and patterned, using lithography and etch processes (FIG. 10(*g*) and FIG. 10(*h*)), followed by deposition and planarization of a fourth material 716, typically a sacrificial material (FIG. 10(*i*) and FIG. 10(*j*)). Repeating the process flow of deposition of patterning material 712 or material 715 alternatively, and deposition of material 716 and planarization by chemical mechanical polishing (FIG. 10(*k*)-(*m*)), a film stack featuring multiple layers with alternating material 712 (e.g., a conducting material) and material 715 (e.g., an insulating material) in at least portions of the device is formed. Finally, material 716 between film stacks 771 and 772 is removed by wet etch, dry etch (which may require lithography process), or vapor etch, selective to all other materials (FIG. 10(*n*)). As illustrated in FIG. 10(*o*), in the case of 712 being a conductive material connected to an electrical circuit or an electrical source (e.g., a charge source), each probe tip formed by 712 on the stack (e.g., 781 and 782) can have a charge or an electrical field at the surface (e.g., 781 and 782), which (each probe tip) can be selected to have a positive charge or a negative charge, or a positive electrical field or negative electrical field. Conversely, such probe tip can also sense various properties of biological subject being measured (e.g., electronic cloud, field, charge, or temperature when the probe tip is a thermal detector, or light emission when the probe tip is an optical sensor). Using electrical circuit or electrical source, various combinations of electrical charge distribution or electrical field can be placed on the micro-device, as shown in FIG. 10(*o*) and FIG. 10(*p*), which can be used to sort and trap various biological subjects such as a cell and a DNA molecule. For instance, a biological subject with a charge distribution inverse of that in FIG. 10(*p*) can be trapped by the micro-device shown in FIG. 10(*p*). An array of micro-devices with various charge distributions or electrical field distributions can trap their respective biological subjects in a high speed, which can serve as a sorting device. FIG. 10(*q*) illustrates the use of a micro-device capable of trapping a DNA or measuring various properties (e.g., electrical, thermal, or optical properties) of a DNA, with each probe tip matched up spatially with either a major groove or minor groove of a double helix DNA. FIG. 10(*r*) illustrates how the probe tips are connected to electrical circuit, where only electrical wiring is shown. It should be noted that the micro-device shown in this example can be integrated onto a single chip with one billion or more such micro-devices to trap and/or sort cells, DNAs, RNAs, proteins, and other biological subject in a high speed.

Another aspect of this invention relates to micro-indentation probes and micro-probes for measuring a range of physical properties (such as mechanical properties) of biological subjects. Examples of the mechanical properties include hardness, shear strength, elongation strength, fracture stress, and other properties related to cell membrane which is believed to be a critical component in disease diagnosis.

Figure 11:
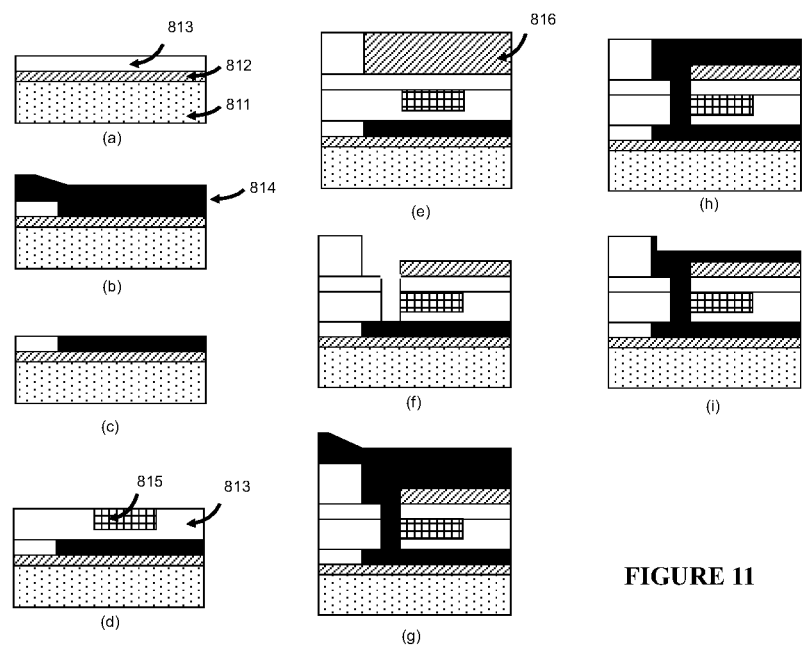
FIG. 11 illustrates a novel process flow for fabricating a class of micro-devices capable of measuring physical properties of a biological entity (e.g., a cell) such as mechanical properties (e.g., hardness, shear strength, elongation strength, fracture stress) and other properties related to cell membrane.
Figure 11:
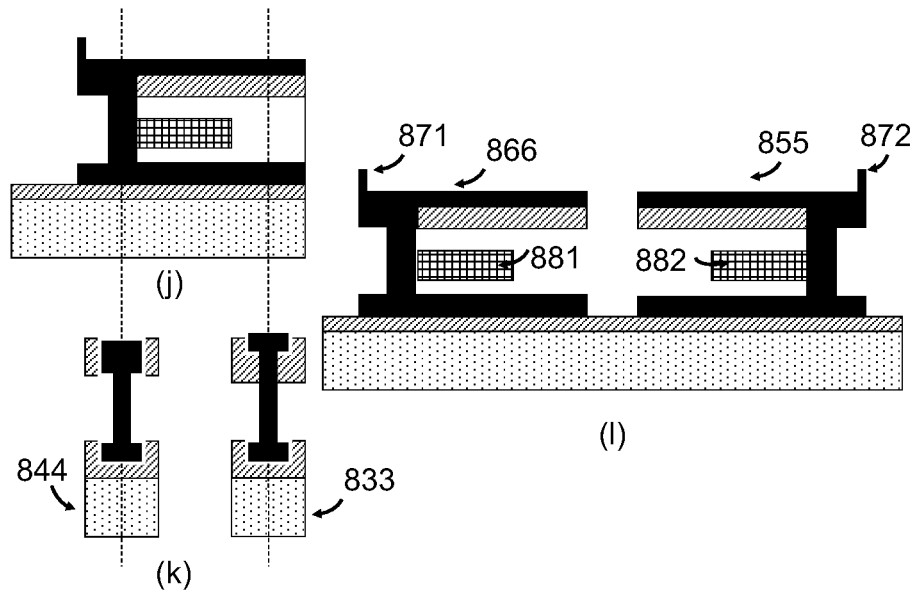

FIG. 11 illustrates a novel fabrication process flow for micro-devices capable of probing a range of properties of biological subjects, such as mechanical properties of cell membrane (e.g., mechanical strength of a cell membrane). In this process flow, a material 812 is first deposited onto a substrate 811, followed by the deposition of another material 813 (FIG. 11(*a*)). Following patterning of material 813 using lithography and etch processes, a material 814 is deposited (FIG. 11(*b*)) and planarized (FIG. 11(*c*)). Another layer of material 813 is next deposited and patterned using lithography and etch processes to remove portions of the material 813, followed by the deposition and planarization of a material 815 (which can be a piezo-electrical material and can serve as a driver) (FIG. 11(*d*)). A layer of material 813 is next deposited, followed by deposition and patterning of yet another layer of 813, and deposition and planarization of material 816 (FIG. 11(*e*)). Next, material 816 is etched back to a reduced thickness, and patterned, followed by patterning of triple-layer of material 813 (FIG. 11(*f*)). Another layer of 814 is deposited (FIG. 11(*g*)) and planarized by chemical mechanical polishing (FIG. 11(*h*)), and patterned (FIG. 11(*i*)). Finally, multiple layers of 813 are removed by wet etch, plasma etch, or vapor etch (FIG. 11(*j*)). FIG. 11(*k*) is a perspective, cross-sectional illustration of the micro-device in a plane perpendicular to that in FIG. 11(*j*) (90-degree rotation from FIG. 11(*j*)). FIG. 11(*l*) illustrates a micro-device with two micro-tips 871 and 872 which can move in opposite directions when a voltage is applied to piezo-electrical drivers 881 and 882, which can be used to probe biological subjects such as cells.

Figure 12:
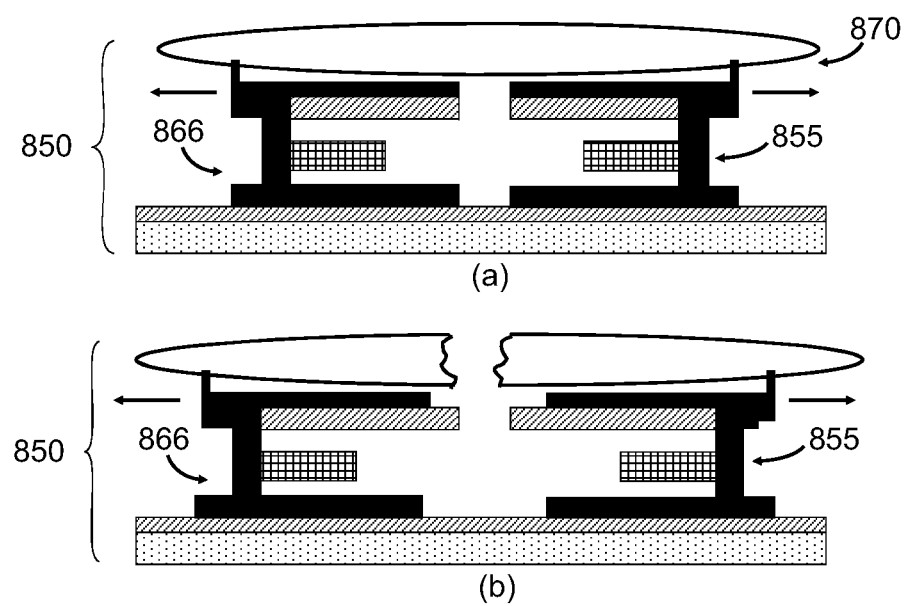
FIG. 12 illustrates how a micro-device with two micro-probes capable of moving in opposite directions when a force is applied can be utilized to probe properties of a biological entity (e.g., mechanical properties of a cell membrane).

FIG. 12 is an illustration of how micro-devices fabricated using the novel manufacturing process shown in FIG. 11 work. In FIG. 12, a micro-device 850 with two micro-probes 866 and 855 can move in opposite directions upon a force being applied (FIG. 12(*a*)). When the tips of the two probes are penetrated into a cell 870, as the distance between the two micro-probes is increased with the increasing applied force, the cell is stretched. Finally, as the applied force is reached a critical value, the cell is broken into two pieces (FIG. 12(*b*)). The dynamic response of the cell to the applied force provides information on the cell, particularly on the mechanical properties (e.g., elasticity) of cell membrane. The force at the point in which the cell is torn apart reflects the strength of the cell and it may be called a breaking point: the greater the mechanical strength of the cell membrane is, the greater the force is at the breaking point.

Another novel approach provided by this invention is the use of phase lock-in measurement for disease detection, which reduces background noise and effectively enhances signal to noise ratio. Generally, in this measurement approach, a periodic signal is used to probe the biological sample and response coherent to the frequency of this periodic probe signal is detected and amplified, while other signals not coherent to the frequency of the probe signal is filtered out, which thereby effectively reduces background noise. In one of the embodiments in this invention, a probing micro-device can send a periodic probe signal (e.g., a pulsed laser team, a pulsed thermal wave, or an alternating electrical field) to a biological subject, response to the probe signal by the biological subject can be detected by a detecting micro-device. The phase lock-in technique can be used to filter out unwanted noise and enhance the response signal which is synchronized to the frequency of the probe signal. The following two examples illustrate the novel features of time of flight detection arrangement in combination with phase lock-in detection technique to enhance weak signal and therefore detection sensitivity in disease detection measurements.

FIG. 13 is an illustration of a novel time of flight detection arrangement for disease detection applications. Specifically, FIG. 13(*a*) shows a set-up for measuring biological subject 911 using detection probe 933 and clock generator 922, and FIG. 13(*b*) contains recorded signal 921 due to structure 922, signal 931 recorded by signal probe 933, and processed signal 941 using a phase lock-in technique to filter out noise in recorded signal 931, where only response synchronized to clock signal 921 is retained. In the setup shown in FIG. 13(*a*), when a biological subject such as a cell 911 passes a structure 922, it triggers a clear signal (e.g., a light scattering signal if 922 is a light source, or a sharp increase in voltage if 922 is an orifice structure in a resistor). Therefore, 922 can be used to register the arrival of the biological subject, and as a clock when multiple structures of 922 are placed at a periodic distance as shown in recorded signal trace 921 in FIG. 13(*b*). In addition, when 922 is placed at a known distance in front of a probe 933, it marks the arrival of a biological subject coming towards 933 and signal response recorded at 933 is delayed by a time t from the signal triggered by 922 where t equals distance between 922 and 933 divided by traveling speed of the biological subject. As illustrated in FIG. 13(*b*), signal 921 due to structure 922 is clear and periodic with periodicity proportional to distance between structure 922s, while signal measured by probe 933 has a high noise level and relatively weak signal related to the biological subject. With the utilization of phase lock-in technique to filter out noise in recorded signal 931 by the detection probe 933 un-synchronized to clock signal 921, signal to noise ratio can be greatly enhanced as shown in processed signal 941 in FIG. 13(*b*).

FIG. 14 illustrates yet another time of flight disease detection arrangement in which a clock signal generator 922, a probe signal generator 944, and a signal detection probe 955 are used, along with schematically recorded clock signal 921, total recorded response signal 951 (except clock signal), and processed signal 952 using phase lock-in technique. In this arrangement, a probe signal generator 944 is used to perturb the biological subject 911 (e.g., heating 911 up using an optical beam, or adding an electrical charge to 911), and response to the probe signal is subsequently measured as a function of time using an array of detection probes 955. The filtered signal in 952 shows dynamic response to probe signal by 944 as it decays over time. Since normal cell and abnormal cell may respond differently to the probe signal, this arrangement with proper micro-probes can be utilized to detect diseases such as cancer. In another embodiment utilizing this set-up (shown in FIG. 14), the probe signal generator 944 can send a periodic signal to the biological subject 911, detected response signal from the biological subject by the detection probe 955 can be processed using the phase lock-in technique, with noise un-synchronized to the frequency of the probe signal filtered out and signal synchronized to the probe signal frequency amplified.

FIG. 15 is a perspective illustration of the novel multi-property micro-filter. A timed shutter 1502 is sandwiched between 2 pieces of filter membrane 1501 with wells. When a biological subject 1511 moves through the pathway of the well, it is first detected by the counter 1512, which triggers the clock of the barrier panel 1502. Then the larger cells will be filtered out, or blocked, by the filter's holes 1001, while only the specific subjects with enough speed are able to get through the pathway 1503 before the timed shutter 1502 closes the filter pathway (see FIG. 15(*b*)). Otherwise it will be held back as the timed shutter 1502 moves to block the pathway as shown in FIG. 15(*c*).

FIG. 16 illustrates a fluid delivery system that includes a pressure generator, a pressure regulator, a flow meter, a flow regulator, a throttle valve, a pressure gauge, and distributing kits. The pressure generator 1605 sustains fluid with desired pressure, and the pressure is further regulated by the regulator 1601 and then accurately manipulated by the throttle valve 1602. Meanwhile, the pressure is monitored at real time and fed back to the throttle valve 1602 by the pressure gauge 1603. The regulated fluid is then in parallel conducted into the multiple devices where a constant pressure is needed to drive the fluid sample.

FIG. 17 illustrates how a micro-device in a disease detection apparatus of this invention can communicate, probe, detect, and optionally treat and modify biological subjects at a microscopic level. FIG. 17(*a*) illustrates the sequence of cellular events from signal recognition to cell fates determination. First, as the signals 1701 are detected by receptors 1702 on the cell surface, the cell will integrate and encode the signals into a biologically comprehensible message, such as calcium oscillation 1703. Consequently, corresponding proteins 1704 in the cell will interact with the message, then be modified and transform into ion-interacted proteins 1705 accordingly. Through the translocation, these modified proteins 1705 will pass the carried message to the nuclear proteins, and the controlled modification on nuclear proteins will modulate the expression of gene 1707 which includes transcription, translation, epigenetic processes, and chromatin modifications. Through messenger RNA 1709, the message is in turn passed to specific proteins 1710, thereby changing their concentration—which then determines or regulates a cell's decision or activities, such as differentiation, division, or even death.

FIG. 17(*b*) illustrates a micro-device or sub-equipment of this invention which is capable of detecting, communicating with, treating, modifying, or probing a single cell, by a contact or non-contact means. The apparatus is equipped with micro-probes and micro-injectors which are addressed and modulated by the controlling circuitry 1720. Each individual micro-injector is supplied with a separate microcartridge, which carries designed chemicals or compounds.

To illustrate how a micro-device can be used to simulate an intracellular signal, calcium oscillation is taken as an example mechanism. First, a $Ca^{2+}$-release-activated channel (CRAC) has to be opened to its maximal extent, which could be achieved by various approaches. In an example of the applicable approaches, a biochemical material (e.g., thapsigargin) stored in the cartridge 1724 is released by an injector 1725 to the cell, and the CRAC will open at the stimulus of the biological subject. In another example of the applicable approaches, the injector 1724 forces a specific voltage on cell membrane, which causes the CRAC to open as well.

The $Ca^{2+}$ concentration of a solution in the injector 1728 can be regulated as it is a desirable combination of a $Ca^{2+}$-containing solution 1726, and a $Ca^{2+}$ free solution 1727. While the injector 1730 contains a $Ca^{2+}$ free solution, then injectors 1728 and 1730 are alternately switched on and off at a desired frequency. As such, the $Ca^{2+}$ oscillation is achieved and the content inside the cell membrane are then exposed to a $Ca^{2+}$ oscillation. Consequently, the cell's activities or fate is being manipulated by the regulated signal generated by the apparatus.

Meanwhile, the cell's response (e.g., in the form of a thermal, optical, acoustical, mechanical, electrical, magnetic, electromagnetic property, or a combination thereof) can be monitored and recorded by the probes integrated in this apparatus.

FIG. 17(*c*) illustrates another design of a micro-device or sub-equipment which is able to setup communication with a single cell. The apparatus is equipped with micro-probes which are coated with biologically compatible compounds or elements, e.g., Ca, C, Cl, Co, Cu, H, I, Fe, Mg, Mn, N, O, P, F, K, Na, S, or Zn. These probes can generate oscillating chemical signals with such an element or compound to interact with the cell, and results into a response that affects the cell's activities or eventual fate as describe above. Likewise, this apparatus can probe and record the cell's response (e.g., in the form of an electrical, magnetic, electromagnetic, thermal, optical, acoustical, biological, chemical, electro-mechanical, electro-chemical, electrochemical-mechanical, bio-chemical, bio-mechanical, bioelectro-mechanical, bio-electro-chemical, bio-electrochemical-mechanical, physical, mechanical property, or a combination thereof) as well.

FIG. 18 illustrates the system block diagram of a microdevice or sub-equipment of this invention. This example includes a fluid delivering system 1801, biological interface 1802, a probing and detecting device 1803, a system controller 1805, a medical waste reclaiming and treating system 1804. A biological sample or material is transported to the interface 1802 by the fluid delivery system 1801, meanwhile the fluid parameters (or properties) are reported to the system controller 1805 which comprises a logic processing unit, a memory unit, an application specific chip, a sensor, a signal transmitter, and a signal receiver; and then the system controller 1805 can give further command to the system. The interface 1802 is an assembly which bridges a fluid sample and the detecting device, and further monitors the parameters or properties of the biological sample (e.g., pressure, temperature, stickiness, or flow rate) and then reports the date to the system controller 1805 while distributing the biological sample to the probing and detecting device 1803 with a specified speed or pressure (which can be commanded by the system controller 1805).

The system controller 1805 is the central commander and monitor of the entire system (or apparatus), where all the parameters and information from various modules is processed and exchanged and the instructions are given out, and where the command is dispatched. The system controller 1805 can include, e.g., a pre-amplifier, an electrical meter, a thermal meter, a switching matrix, a system bus, a nonvolatile storage device, a random access memory, a processor, and a user interface through which the user of the apparatus can manipulate, configure the apparatus, and read the operating parameters and final result. The pre-amplifier can process the raw signal to a recognizable signal for the meters. The meters can force and measure corresponding signals which can be, e.g., electrical, magnetic, electromagnetic, thermal, optical, acoustical, biological, chemical, electro-mechanical, electro-chemical, electro-chemical-mechanical, bio-chemical, bio-mechanical, bio-electromechanical, bio-electro-chemical, bio-electro-chemical-mechanical, physical, or mechanical signals, or combinations thereof. The switching matrix can switch the testing terminals of different arrays of the probe sub-apparatus. The user interface includes input and output assemblies and is an assembly which seals the fluid delivery system and the probing and detecting device together.

The probing and detecting device 1803 is the core functional module of the disease detection apparatus of this invention as it is the unit that probes the biological sample and collects related cellular signals (or responses). The waste reclaiming and treating system 1804 reclaims the waste biological sample to protect the privacy of its biological host, and keeps it away from polluting the environment.

Figure 19:
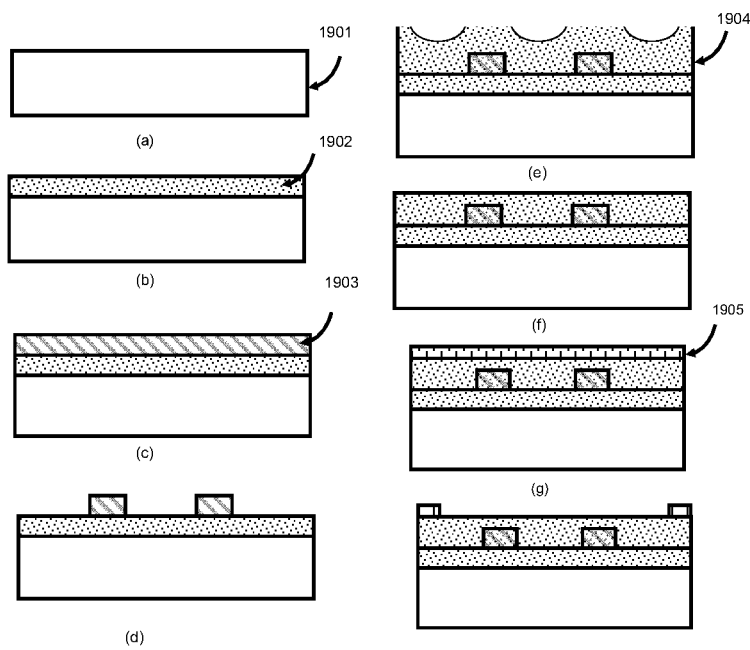
Figure 19:
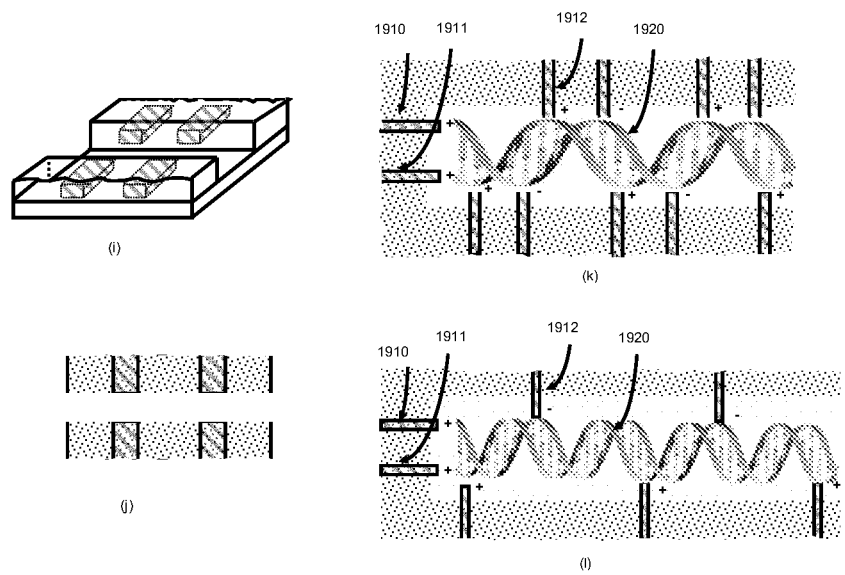

FIGS. 19(*b*)-(*n*) illustrate a process flow for fabricating a micro-device for trapping, sorting, probing, measuring, treating, or modifying a biological subject (e.g., a single cell, a DNA or RNA molecule). A first material 1902 (e.g., a piezo-electrical conducting material) and a second material 1903 (e.g., a conducting material) are sequentially deposited on a substrate 1901 (see FIGS. 19(*b*) and 19(*c*)). The second material 1903 is subsequently patterned by lithography and etch processes (see FIG. 19(*d*)). A third material 1904 is next deposited (as shown in FIG. 19(*e*)) and planarized (see FIG. 19(*f*)). A layer of a fourth material 1905 is subsequently deposited (see FIG. 19(*g*)) and patterned as a hard mask (see FIG. 19(*h*)), followed by etch to remove the third and first materials from desired areas, which stops on the substrate 1901. FIG. 19(*i*) is a perspective illustration of the device, while FIG. 19(*j*) is a vertical illustration of the same device.

FIG. 19 (*k*) illustrates the use of a micro-device capable of trapping a DNA 1920 and measuring various properties (e.g., electrical, magnetic, physical, thermal, chemical, biological, bio-chemical, or optical properties) of a DNA. Each probe tip 1912 matches up spatially with either a major groove or minor groove of a double helix DNA. Meanwhile, two probes (1911 and 1910) configured at the end of the trench can force or measure signals to each strand end of the DNA's double helix. The probes can be made of a conducting material with optionally a piezo-electrical support structure, which can stretch forward and backward at a desired distance. All the probes are numbered, addressed, and controlled by a controlling circuitry.

FIG. 19(*l*) shows a simplified form of the device illustrated in FIG. 19(*k*). In this device, probe tips match spatially with interlaced grooves of a double helix DNA. The number of groove intervals between the adjacent probes is variable. If required, either DNA can be moved (for example, by pulling by probes 1910 and 1911) or the probes can move along the trench direction, mapping out properties in a full or partial DNA.

FIG. 20 illustrates a micro-device or sub-equipment of this invention that is capable of detecting or measuring the surface charge of a biological subject 2010. It includes a channel, a pair of plates 2022, and a slit 2030 which separates the channel into a top channel 2041 and a bottom channel 2051. When a biological subject 2010 carrying a surface charge (positive charge shown in FIG. 20(*a*)) passes through the channel, under the influence of the voltage applied on the plates 2022 (with positive voltage at the top plate and negative at the bottom plate), it will move towards the bottom plate as shown in FIG. 20(*b*). Thus, the biological subject 2010 will pass through the bottom channel 2051 when it reaches slit 2030. (If the biological subject 2010 carries a negative charge, it would pass through the top channel 2041.) This way, a biological subject with unknown charge type (negative or positive) can be determined by using this apparatus.

This device comprises at least 2 parts of channel, one of which is channel 2060 where the biological subject is charged or modified, and the other comprises at least one plate or slit to separate the biological subjects (e.g., where the biological subjects are separated).

As surface charge will affect the shape of a biological subject, by using novel and multiple plates, information on the shape and charge distribution of biological subjects can be obtained. The general principle and design of the micro-device can be extended to a broader scope, thereby making it possible to obtain other information on the biological subject via separation by applying other parameters such as ion gradient, thermal gradient, optical beam, or another form of energy.

FIG. 21 illustrates another micro-device or sub-equipment of this invention for detecting or measuring microscopic properties of a biological subject 2110 by utilizing a micro-device that includes a channel, a set of probes 2120, and a set of optical sensors 2132 (see, FIG. 21(*a*)). The detected signals by probes 2120 can be correlated to information including images collected by the optical sensors 2132 to enhance detection sensitivity and specificity. The optical sensors can be, e.g., a CCD camera, a florescence light detector, a CMOS imaging sensor, or any combination.

Alternatively, a probe 2120 can be designed to trigger optical emission such as florescence light emission 2143 in the targeted biological subject such as diseased cells, which can then be detected by an optical probe 2132 as illustrated in FIG. 21(*c*). Specifically, biological subjects can be first treated with a tag solution which can selectively react to diseased cells. Subsequently, upon reacting (contact or non-contact) with probe 2120, optical emissions from diseased cells occur and can be detected by optical sensors 2132. This novel process using the apparatus of this invention is more sensitive than such conventional methods as traditional florescence spectroscopy as the emission trigger point is directly next to the optical probe and the triggered signal 2143 can be recorded in real time and on-site, with minimum loss of signal.

FIG. 22 illustrates another embodiment of the apparatus of this invention, which can be used to separate biological subjects of different geometric size and detect their properties respectively. It includes at least an entrance channel 2210, a disturbing fluid channel 2220, an accelerating chamber 2230, and two selecting channels 2240 and 2250. The angle between 2220 and 2210 is between 0° and 180°. The biological subject 2201 flows in the x-direction from 2210 to 2230. The biocompatible distribution fluid 2202 flows from 2220 to 2230. Then the fluid 2202 will accelerate 2201 in y-direction. However, the acceleration correlates with the radius of the biological subjects and the larger ones are less accelerated than the small ones. Thus, the larger and smaller subjects are separated into different channels. Meanwhile, probes can be optionally assembled aside the sidewall of 2210, 2220, 2230, 2240, and 2250. They could detect electrical, magnetic, electromagnetic, thermal, optical, acoustical, biological, chemical, physical, mechanical properties, or combinations thereof at the microscopic level. In the mean time, if desired, a cleaning fluid can also be injected into the system for dissolving and/or cleaning biological residues and deposits (e.g., dried blood and protein) in the narrow and small spaces in the apparatus, and ensuring smooth passage of a biological subject to be tested through the apparatus.

The channel included in the apparatus of this invention can have a width of, e.g., from 1 nm to 1 mm. The apparatus should have at least one inlet channel and at least two outlet channels.

FIG. 23 shows another micro-device or sub-equipment of this invention with an acoustic detector 2320 for measuring the acoustic property of a biological subject 2301. This device includes a channel 2310, and at least an ultrasonic emitter and an ultrasonic receiver installed along the sidewall of the channel. When the biological subject 2301 passes through the channel 2310, the ultrasonic signal emitted from 2320 will be received after carrying information on 2301 by the receiver 2330. The frequency of the ultrasonic signal can be, e.g., from 2 MHz to 10 GHz, and the trench width of the channel can be, e.g., from 1 nm to 1 mm. The acoustic transducer (i.e., the ultrasonic emitter) can be fabricated using a piezo-electrical material (e.g., quartz, berlinite, gallium, orthophosphate, $GaPO_4$, tourmalines, ceramics, barium, titanate, $BatiO_3$, lead zirconate, titanate PZT, zinc oxide, aluminum nitride, and polyvinylidene fluorides).

FIG. 24 shows another apparatus of this invention that includes a pressure detector for biological subject 2401. It includes at least one channel 2410 and whereon at least one piezo-electrical detector 2420. When the biologic subject 2401 passes through the channel, the piezo-electrical detector 2420 will detect the pressure of 2401, transform the information into an electrical signal, and send it out to a signal reader. Likewise, the trench width in the apparatus can be, e.g., from 1 nm to 1 mm, and the piezo-electrical material can be, e.g., quartz, berlinite, gallium, orthophosphate, $GaPO_4$, tourmalines, ceramics, barium, titanate, $BatiO_3$, lead zirconate, titanate PZT, zinc oxide, aluminum nitride, or polyvinylidene fluorides.

FIG. 25 shows another apparatus of this invention that include a concave groove 2530 between a probe couple, in the bottom or ceiling of the channel. When a biological subject 2510 passes through, the concave 2530 can selectively trap the biological subject with particular geometric characteristics and makes the probing more efficiently. The shape of concave's projection can be rectangle, polygon, ellipse, or circle. The probe could detect electrical, magnetic, electromagnetic, thermal, optical, acoustical, biological, chemical, physical, mechanical properties, or combinations thereof. Similarly, the trench width can be, e.g., from 1 nm to 1 mm. FIG. 25(*a*) is an up-down view of this apparatus, FIG. 25(*b*) is a side view, whereas FIG. 25(*c*) is a perspective view.

FIG. 26 is another apparatus of this invention that also includes concave grooves 2630 (of a different shape from those shown in FIG. 25) on the bottom or ceiling of the channel. When a biological subject 2610 passes through, the concave grooves 2630 will generate a turbulent fluidic flow, which can selectively trap the micro-biological subjects with particular geometric characteristics. The probe could detect, e.g., electrical, magnetic, electromagnetic, thermal, optical, acoustical, biological, chemical, physical, mechanical properties, or a combination thereof. The depth of the concave groove can be, e.g., from 10 nm to 1 mm, and the channel width can be, e.g., from 1 nm to 1 mm.

FIG. 27 illustrated a micro-device with a stepped channel 2710. When a biological subject 2701 passes through the channel 2710, probe couples of different distances can be used to measure different microscopic properties, or even the same microscopic at different sensitivity at various steps (2720, 2730, 2740) with probe aside each step. This mechanism can be used in the phase lock-in application so that signal for the same microscopic property can be accumulated. The probes can detect or measure microscopic electrical, magnetic, electromagnetic, thermal, optical, acoustical, biological, chemical, physical, mechanical properties, or combinations thereof.

FIG. 28 illustrates another apparatus of this invention with thermal meters 2830. It includes a channel, a set of probes 2820, and a set of thermal meters 2830. The thermal meters 2830 can be an infrared sensor, a transistor sub-threshold leakage current tester, or thermister.

FIG. 29 illustrates a specific apparatus of this invention which includes carbon a nano-tube 2920 with a channel 2910 inside, probes 2940 which can detect at the microscopic level an electrical, magnetic, electromagnetic, thermal, optical, acoustical, biological, chemical, physical, or mechanical property, or a combination thereof. The carbon nano-tube 2920 as shown contains a double-helix DNA molecule 2930. The carbon nano-tube can force and sense electrical signals by the probes 2940 aside. The diameter of the carbon nano tube diameter can be, e.g., from 0.5 nm to 50 nm, and its length can range from, e.g., 5 nm to 10 mm.

FIG. 30 shows an integrated apparatus of this invention that includes a detecting device (shown in FIG. 30(*a*)) and an optical sensor (shown in FIG. 30(*b*)) which can be, e.g., a CMOS image sensor (CIS), a Charge-Coupled Device (CCD), a florescence light detector, or another image sensor. The detecting device comprises at least a probe and a channel, and the image device comprises at least 1 pixel. FIG. 30(*c*-1) and FIG. 30(*c*-2) illustrate the device with the detecting device and optical sensor integrated. As illustrated in FIG. 30(*d*), when biological subjects 3001, 3002, 3003 pass through, the probe 3010 in the channel 3020, its electrical, magnetic, electromagnetic, thermal, optical, acoustical, biological, chemical, physical, mechanical property or a combination thereof could be detected by the probe 3010 (see FIG. 30(*e*)), meanwhile its image could be synchronously recorded by the optical sensor (FIG. 30(*f*)). Both the probed signal and image are combined together to provide a diagnosis and enhanced detection sensitivity and specificity. Such a detecting device and an optical sensing device can be designed in a system-on-chip or be packaged into one chip.

FIG. 31 shows a micro-device or sub-equipment with a detecting micro-device (FIG. 31(*a*)) and a logic circuitry (FIG. 31(*b*)). The detecting device comprises at least a probe and a channel, and the logic circuitry comprises an addressor, an amplifier, and a RAM. When a biological subject 3101 passes through the channel, its property could be detected by the probe 3130, and the signal can be addressed, analyzed, stored, processed, and plotted in real time. FIG. 31(*c*-1) and FIG. 31(*c*-2) illustrate the device with detecting device and Circuitry integrated. Similarly, the detecting device and the integrated circuit can be designed in a System-on-Chip or be packaged into one chip.

FIG. 32 shows a micro-device or sub-equipment of this invention that comprises a detecting device (FIG. 32(*a*)) and a filter (FIG. 32(*b*)). When a biological subject 3201 passes through the device, a filtration is performed in the filter, and irrelevant objects can be removed. The remaining subjects' property can then be detected by the probe device (FIG. 31(*a*)). The filtration before probing will enhance the precision of the device. The width of the channel can also range, e.g., from 1 nm to 1 mm.

FIG. 33 shows the geometric factors of DNA 3330 such as spacing in DNA's minor groove (3310) have an impact on spatial distribution of electrostatic properties in the region, which in turn may impact local biochemical or chemical reactions in the segment of this DNA. By probing, measuring, and modifying spatial properties of DNA (such as the spacing of minor groove) using the disclosed detector and probe 3320, one may detect properties such as defect of DNA, predict reaction/process at the segment of the DNA, and repair or manipulate geometric properties and therefore spatial distribution of electrostatic field/charge, impacting biochemical or chemical reaction at the segment of the DNA. For example, tip 3320 can be used to physically increase spacing of minor groove 3310.

FIG. 34 shows the fabrication process for an apparatus of this invention that has a flat cover atop of trench to form a channel. This will eliminate the need for coupling two trenches to form a channel, which can be tedious for requiring perfect alignment. The cover can be transparent and allow observation with a microscope. It can comprise or be made of silicon, SiGe, $SiO_2$, various types of glass, or $Al_2O_3$.

FIG. 35 is a diagram of an apparatus of this invention for detecting a disease in a biological subject. This apparatus includes a pre-processing unit, a probing and detecting unit, a signal processing, and a disposal processing unit.

FIG. 36 shows an example of a sample filtration sub-unit in the pre-processing unit, which can separate the cells with different dimensions or sizes. This device comprises at least one entrance channel 3610, one disturbing fluid channel 3620, one accelerating chamber 3630, and two selecting channels (3640 and 3650). The angle 3660 between 3620 and 3610 ranges from 0° to 180°.

The biological subject 3601 flows in the x direction from the entrance channel 3610 to the accelerating chamber 3630. A bio-compatible fluid 3602 flows from disturbing fluid channel 3620 to the accelerating chamber 3630, it then accelerates the biological subject 3601 in the y-direction. The acceleration correlates with the radius of the biological subject and the larger ones are less accelerated than the smaller ones. Then, the larger and smaller subjects are separated into different selecting channels. Meanwhile, probes can be optionally assembled on the sidewalls of the channels 3610, 3620, 3630, 3640, and 3650. The probes could detect, at the microscopic level, electrical, magnetic, electromagnetic, thermal, optical, acoustical, biological, chemical, biochemical, electro-mechanical, electro-chemical, electro-chemical-mechanical, physical, mechanical properties, or combinations thereof.

FIG. 37 is a diagram of another example of a sample filtration unit in the apparatus of this invention. 3701 represents small cells, while 3702 represents large cells. When a valve 3704 is open and another valve 3703 is closed, biological subjects (3701 and 3702) flow towards exit A. Large cells that have larger size than the filtration hole are blocked against exit A, while small cells are flushed out through exit A. The entrance valve 3704 and exit A valve 3707 are then closed, and a bio-compatible fluid is injected through the fluid entrance valve 3706. The fluid carries big cells are flushed out from exit B. The larger cells are then analyzed and detected in the detection part of the invention.

FIG. 38 is a diagram of a pre-processing unit of an apparatus of this invention. This unit includes a sample filtration unit, a recharging unit or system for recharging nutrient or gas into the biological subject, a constant pressure delivery unit, and a sample pre-probing disturbing unit.

FIG. 39 is a diagram of an information or signal processing unit of an apparatus of this invention. This unit includes an amplifier (such as a lock-in amplifier) for amplifying the signal, an A/D converter, and a micro-computer (e.g., a device containing a computer chip or information processing sub-device), a manipulator, a display, and network connections.

FIG. 40 shows the integration of multiple signals which results in cancellation of noise and enhancement of signal/noise ratio. In this figure, a biological 4001 is tested by Probe 1 during Δ t between t1 and t2, and by Probe 2 during Δ t between t3 and t4. 4002 is 4001's tested signal from Probe 1, and 4003 is from Probe 2. Signal 4004 is the integration result from signal 4002 and 4003. The noise cancels out each other in certain extent and results in an improved signal strength or signal/noise ratio. The same principle can be applied to data collected from more than more than 2 micro-devices or probing units.

FIG. 41 shows one embodiment of the fabrication processes flow of this invention for manufacturing a detection device with at least one detection chamber and at least one detector. In this example, following an optional process flow of fabricating data storage, data processing and analyzing components (including transistors, memory devices, logic circuits, and RF devices), a material 4122 is first deposited onto a substrate 4111, followed by the deposition of another material 4133 (material for future detectors). Material 4133 can be selected from electrically conductive materials, piezo-electrical materials, semiconductor materials, thermal sensitive materials, ion emission sensitive materials, pressure sensitive materials, mechanical stress sensitive materials, or optical materials. Optionally, it can also consist of composite materials or a desired material stack. If required, an integrated detector with a set of sub-components can be placed at this level. Material 4133 is next patterned using lithography and etch processes, forming a set of desired features shown in FIG. 41(c). Another material 4144 is subsequently deposited, which can be the same as or different from material 4122. Material 4122 can be an electrically insulating material such as oxide ($SiO_2$), doped oxide, silicon nitride, or polymer material. Next, the material 4144 is optionally planarized using polishing (e.g., using chemical mechanical polishing) or etch back process. The material stack is then patterned using lithography and etch processes, stopping on substrate 4111. Finally, as shown in FIG. 41(g), a capping layer or the surface of another component 4155 is placed on top of the material stack (thereby sealing or capping it), forming an enclosed detection chamber 4166 with detector 4177 for biological sample detection.

FIG. 42 illustrates another embodiment of the fabricating method of this invention for manufacturing a detection device with enclosed detection chambers, detectors, and channels for transporting biological samples such as fluidic samples. In this embodiment, following an optional process flow of fabricating data storage, data processing and analyzing components (including transistors, memory devices, logic circuits, and RF devices), a material 4222 is first deposited onto a substrate 4211, followed by the deposition of another material 4233 (material for future detectors). Material 4233 can be selected from electrical conductive materials, piezo-electrical materials, semiconductor materials, thermal sensitive materials, ion emission sensitive materials, pressure sensitive materials, mechanical stress sensitive materials, or optical materials. Optionally, it can also include composite materials or a desired material stack. If required, an integrated detector with a set of sub-components can be placed at this level.

Materials 4222 and 4233 are subsequently patterned using lithography and etch processes (FIG. 42(c)). These two layers (4222 and 4233) can be patterned in separate patterning processes sequentially, or can be patterned in the same process, pending on device design, types of materials and etch chemistries. Substrate 4211 is next etched as shown in FIG. 42(d), forming a recessed area (cavity) in 4211, in which stacks 4222 and 4233 can be used as a hard mask during the etch process.

A material 4244 is deposited into the recessed area, and the portion of the material 4244 above the material 4233 is removed using a polishing (chemical or mechanical) or etch back process. Material 4244 can be selected from oxide, doped oxide, silicon nitride, and polymer materials. A layer 4255 is then deposited onto material 4244 and patterned to form small holes at selected locations. A wet or vapor etch is utilized next to remove material 4244, forming an enclosed detection chamber 4266.

Optionally, as shown in FIG. 42(i), the material 4222 is also removed using wet or vapor etch process, forming channels 4288 connecting various detection chambers, thus forming detection chambers with a detector 4277 lined with the walls of the detection chamber and with gaseous or fluidic biological samples flowing through the chambers. Finally, the top surface of the detection chamber is sealed with another layer of material (e.g., 4255).

FIG. 43 shows a novel disease detection method of this invention in which at least one probe object is launched at a desired speed and direction toward a biological subject, resulting in a collision. The response(s) by the biological subject during and/or after the collision is detected and recorded, which can provide detailed and microscopic information on the biological subject such as weight, density, elasticity, rigidity, structure, bonding (between different components in the biological subject), electrical properties such as electrical charge, magnetic properties, structural information, and surface properties. For example, for a same type of cell, it is expected that a cancerous cell will experience a smaller traveling distance after the collision than that of a normal cell due to its denser, greater weight, and possibly larger volume. As shown in FIG. 43(a), a probe object 4311 is launched towards a biological subject 4322. After the collision with the probe object 4311, the biological subject 4322 may be pushed (scattered) out a distance depending on its properties as shown FIG. 43(b).

FIG. 43(c) shows a schematic of a novel disease detection device with a probe object launch chamber 4344, an array of detectors 4333, a probe object 4322 and a biological subject to be tested 4311. In general, a test object can be an inorganic particle, an organic particle, a composite particle, or a biological subject itself. The launch chamber comprises a piston to launch the object, a control system interfaced to an electronic circuit or a computer for instructions, and a channel to direct the object.

FIG. 44 illustrates a novel fabrication process for forming multiple components with different materials at the same device level. First, a first material 4422 is deposited onto a substrate 4411 (see FIG. 44(a)), followed by the deposition of a second material 4433. The second material 4433 is next patterned to form at least a portion of recessed area in the layer 4433, using lithography and etch processes (see FIG. 44(c)). A third material 4444 is subsequently deposited. The third material can be the same as or different from the second material 4422.

The third material directly above the second material is removed via etch back and/or polishing (such as chemical mechanical polishing) processes (see FIG. 44(e)). Optionally, the third material is next patterned to form at least a portion of recessed area in layer 4444 (FIG. 44(f)). A fourth material 4455 is then deposited. Optionally, the portion of the fourth material 4455 directly above the third material 4444 or above both the second and third materials is removed via etch back and/or polishing (such as chemical mechanical polishing). The above process can keep repeating to form multiple features with the same or different materials at the same device level. Hence, this process flow forms at least two components 4466 and 4477 with different materials or the same materials at the same device level. For example, in one embodiment, one component can be used as a prober and the other can be used as a detector.

FIG. 45 illustrates a method for detecting a disease in a biological subject. A biological subject 4501 passes through the channel 4531 at a speed v, and probe 4511 is a probe which can grossly detect the properties of the biological subject at high speed.

Probe 4512 is a fine probing device which is coated by a piezo-electrical material. There is a distance ΔL between probe 4511 and probe 4512.

When the biological subjects are tested when getting through 4511, if the entity is identified to be a suspected abnormal one, the system would trigger the piezo-electrical probe 4512 to stretch into the channel and probe particular properties after a time delay of Δt. And probe 4512 retracts after the suspected entity passed through.

The probing device is capable of measuring at the microscopic level an electrical, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical or mechanical property, or a combination thereof, of the biological subject.

The width of the micro-channel can range from about 1 nm to about 1 mm.

FIG. 46 shows a process of detecting a disease in a biological subject. A biological subject 4601 passes through the channel 4631 at a speed y. Probe 4611 is a probe which can grossly detect the properties of the biological subject at high speed. 4621 and 4622 are piezo-electrical valves to control the micro-channel 4631 and 4632. 4612 is a fine probing device which can probe biological properties more particularly. 4631 is flush channel to rush out normal biological subjects. 4632 is detection channel where the suspected entities are fine detected in this channel.

When a biological subject is tested while getting through 4611, if it is normal, the valve 4621 of the flush channel is open, while the detection channel valve 4622 is closed, the biological subject is flushed out without a time-consuming fine detection.

When the biological subject is tested while getting through 4611, if it is suspected to be abnormal or diseased, the valve 4621 of the flush channel is closed, while the detection channel valve 4622 is open, the biological subject is conducted to the detection channel for a more particular probing.

The width of the micro-channel can range from about 1 nm to about 1 mm.

The probing device is capable of measuring at the microscopic level an electrical, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical or mechanical property, or a combination thereof, of the biological subject.

FIG. 47 illustrates an arrayed biological detecting device. As shown in FIG. 47(a), 4701 are arrayed micro-channels which can get through the fluidics and biological subjects. 4702 are probing devices embedded aside the channels. The sensors are wired by bit-lines 4721 and word-lines 4722. The signals are applied and collected by the decoder R\row-select 4742 and decoder column select 4741. As illustrated in FIG. 47(b), the micro-channel arrayed biological detecting device 4700 can be embedded in a macro-channel 4701. The micro-channel's dimension ranges from about 1 um to about 1 mm. The shape of the micro-channel can be rectangle, ellipse, circle, or polygon.

The probing device is capable of measuring at the microscopic level an electrical, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical or mechanical property, or a combination thereof, of the biological subject.

FIG. 48 illustrates a device of the current invention for disease detection. 4801 is inlet of the detecting device, and 4802 is the outlet of the device. 4820 is the channel where the biological subjects pass through. 4811 is the optical component of the detecting device.

As illustrated in FIG. 48(b), the optical component 4811 consists of an optical emitter 4812 and an optical receiver 4813. The optical emitter emits an optical pulse (e.g. laser beam pulse), when the biological subject 4801 passing through the optical component, and the optical sensor detects the diffraction of the optical pulse, then identify the morphology of the entity.

FIG. 49 shows a schedule for fabricating a piezo-electrical micro-detector of this invention. Particularly, in FIG. 49(*a*), a substrate 4901 is deposited sequentially with a wet etching stop layer 4902 of material A, and with a sacrificial layer 4903 of material B. The sacrificial layer 4903 is then patterned by the lithography and etching processes. Shown in FIG. 49(*b*), a layer 4904 of piezo-electrical material C is then deposited onto the surface of the sacrificial layer 4903, and then planarized. As shown in FIG. 49(*c*), the layer 4904 is then patterned by lithography and etching processes. A second sacrificial layer 4905 (which can be the same as or different from material B) and a second wet etching stop layer 4906 (which can be the same as or different from material A) are subsequently deposited, as shown in FIG. 49(*d*) and FIG. 49(*e*). A patterning process using lithography and etching is performed through layers 4906 and 4905, and etching is stopped on the piezo-electrical layer 4904. It is followed by depositing a conductive layer 4907 of material D is deposited, and then patterning the conductive layer. See FIG. 49(*g*). A patterning process is then followed and the etching stopped on the substrate, thereby forming a trench. See FIG. 49(*h*). An isotropic wet etch selective to material B is then followed, giving rise to a piezo-electrical probe (a cantilever) 4908. See FIG. 49(*i*).

FIG. 50 shows an example of the apparatus of this invention packaged and ready for integration with a sample delivery system and data recording device. As illustrated in FIG. 50(*a*), the device 5001 is fabricated by micro-electronics processes described herein and has at least a micro-trench 5011, a probe 5022, and a bonding pad 5021. The surface of the device's top layer can include SixOyNz, Si, SixOy, SixNy, or a compound containing the elements of Si, O, and N. Component 5002 is a flat glass panel. In FIG. 50(*b*), the flat panel 5002 is shown to be bonded with micro-device 5001 on the side of micro-trench. The bonding can be achieved by a chemical, thermal, physical, optical, acoustical, or electrical means, or any combination thereof. FIG. 50(*c*) shows a conductive wire being bonded with the bonding pad from the side of the pads. As illustrated in FIG. 50(*d*), the device 5001 is then packaged in a plastic cube with only conducting wires exposed. In FIG. 50(*e*), a conical channel 5020 is carved through packaging material and connecting the internal channel of the device. As illustrated in FIG. 50(*f*), the larger opening mouth of the conical channel makes it operational and convenient to mount a sample delivery injector with the device, thereby better enabling the delivery of sample from an injector with relatively large size of injector needle into device with relatively small channels.

FIG. 51 shows another example of the apparatus of this invention packaged and ready for integration with a sample delivery system and data recording device. As shown in FIG. 51(*a*), a micro-device 5100 is fabricated by one or more micro-electronics processes as described in International Application No. PCT/US2011/042637, entitled "Apparatus for Disease Detection." The micro-device 5100 has at least a micro-trench 5104, a probe 5103, a connecting port 5102, and a bonding pad 5105. On the top of the micro-device 5100, the surface layer comprises SixOyNz, Si, SixOy, SixNy, or a compound consisting of Si, O, and N. The surface layer can be covered, and thus the micro-device 5100 is mounted, with a flat glass panel 5101. See FIG. 51(*b*). The mounting can be by a chemical, thermal, physical, optical, acoustical, or electrical means. As shown in FIG. 51(*c*), the conductive wire is bonded with bonding pad from the side of the pads. FIG. 51(*d*) illustrates that the micro-device 5100 can then be packaged in a cube with only conducting wires exposed. The packaging cube can comprise a packaging material such as plastic, ceramic, metal, glass, or quartz. As shown in FIG. 51(*e*), a tunnel 5141 is then drilled into the cube until the tunnel reaches the connecting port 5102. Further, as shown in FIG. 51(*f*), the tunnel 5141 is then being connected to other pipes which can delivery a sample to be tested into the micro-device 5100, and flush out the sample after the sample is tested.

FIG. 52 shows yet another example of the apparatus of this invention packaged and ready for integration with a sample delivery system and data recording device. As illustrated in FIG. 52(*a*), device 5200 is a micro-fluidic device which has at least one micro-channel 5201. 5203 is a pipe that conducts a fluidic sample. The micro-channel 5201 and the conducting pipe 5203 are aligned and submerged in a liquid, for example, water. FIG. 52(*b*) illustrates that, when the temperature of the liquid in which the micro-device and conducting pipe are submerged, is decreased to its freezing point or lower, the liquid solidifies into a solid 5204. As illustrated in FIG. 52(*c*), while the temperature of the liquid is maintained below the freezing point, the combination (including the solid 5204, the conducting pipe 5203, and the device 5200) is enclosed into a packaging material 5205 whose melting temperature is higher than that of the solid 5204, with only the conducting pipe exposed. FIG. 52(*d*) shows that, after the temperature is increased above the melting point of the solid 5204, the solid material 5204 melts and becomes a liquid and is then exhausted from the conducting pipe 5203. The space 5206 wherein the solid material 5204 once filled is now available or empty, and the channel 5201 and the conducting pipe 5203 are now connected through and sealed in the space 5206.

FIG. 53 shows an apparatus of this invention that has a channel (trench) and an array of micro sensors. In FIG. 53(*a*), 5310 is a device fabricated by microelectronics techniques; 5310 comprises micro-sensor array 5301 and addressing and read-out circuitry 5302. The micro-sensor array can include thermal sensors, piezo-electrical sensors, piezo-photronic sensors, piezo-optical electronic sensors, image sensors, optical sensors, radiation sensors, mechanical sensors, magnetic sensors, bio-sensors, chemical sensors, bio-chemical sensors, acoustic sensors, or a combination of them. Examples of thermal sensors include resistive temperature micro-sensors, micro-thermocouples, thermo-diodes and thermo-transistors, and SAW (surface acoustic wave) temperature sensor. Examples of image sensors include CCD (Charge Coupled Device) and CIS (CMOS image sensor). Examples of radiation sensors include photoconductive devices, photovoltaic devices, pyro-electrical devices, and micro-antennas. Examples of mechanical sensors include pressure micro-sensors, micro-accelerometers, micro-gyrometers, and micro flow-sensors. Examples of magnetic sensors include magneto-galvanic micro-sensors, magneto-resistive sensors, magneto diodes and magneto-transistors. Examples of biochemical sensors comprise conductimetric devices and potentiometric devices. FIG. 53(*b*) shows a micro-device 5320 that includes a micro-trench 5321. As illustrated in FIG. 53(*c*), 5310 and 5320 are bonded together to form the new micro-device 5330 which include a trench or channel 5331. The micro-sensor array 5301 is exposed in the channel 5331.

FIG. 54 shows another apparatus of this invention that comprises two panels one of which has an array of micro sensors and two micro cylinders. Particularly, FIG. 54(a) shows a micro-device 5430 fabricated by micro-electronic techniques, which comprises a micro-sensor array 5431 and a read-out circuitry 5432, 5410 is another micro-sensor array chip, and 5420 is a micro-cylinder. As illustrated in FIG. 54(b), a micro-sensor array chip 5430 and two micro-cylinders 5420 are bonded to form a micro-trench with micro-sensor array exposed. In the micro-device illustrated in FIG. 54(c), 5410 is flipped bonded onto the micro-trench device 5431 and forms the device 5450. Device 5450 has a channel with micro-sensor array embedded on top and bottom sides. FIG. 54(d) illustrates the X-cross-section of the micro-device while FIG. 54(e) illustrates the y-cross-section of the micro-.

FIG. 55 shows an apparatus of this invention that comprises two panels one of which has an array of micro sensors and two micro cylinders both of which have a probing sensor. Particularly, in FIG. 55(a), device 5510 is fabricated by microelectronics techniques, which comprises a channel 5511, probe 5513 aside the channel, and a read-out circuitry 5512. FIG. 55(b) illustrates the X-cross-section of the device, while FIG. 55(c) illustrates the y-cross-section of the device. Probe 5513 can apply a disturbing signal to the entities passing through the channel 5511.

FIG. 56 shows another apparatus of this invention comprising several "sub-devices." Particularly, as illustrated in FIG. 56(a), the device 5610 composes "sub-devices" 5611, 5612, 5613, and 5614, among which 5611 and 5613 are devices which can apply disturbing signals, and 5612 and 5614 are micro-sensor arrays. FIG. 56(b) illustrates the functioning diagram of the device 5610, when biological samples 5621 under the test are passing through the channel 5610, they are disturbed by signal A applied by 5611, then being tested and recorded by detecting sensor array 1 of 5612. These biological samples are then disturbed by disturb probe 5613 of array 2, and being tested by detecting sensor 5614 of array 2. Disturbing probe 5611 of array 1 and disturbing probe 5613 of array 2 can apply the same or different signals. Likewise, detecting sensor 5612 of array 1 and detecting sensor 5614 of array 2 can sense or detect the same or different properties.

FIG. 57 shows an example of the apparatus of this invention which includes an application specific integrated circuit (ASIC) chip with I/O pads. Specifically, as illustrated in FIG. 57, 5710 is a micro-device with a micro-fluidic channel 5712 and I/O pads 5711. 5720 is an Application Specific Integrated Circuit (ASIC) chip with I/O pads 5721. 5720 and 5710 can be wired together through the bonding of I/O pads. As such, with an ASIC circuitry 5720, the micro-fluidic detecting device 5710 can perform more complicated computing and analytical functions.

FIG. 58 is a diagram of the underlying principal of the apparatus of this invention which functions by combining various pre-screening and detection methods in unobvious ways. In FIG. 58(a), a biological subject is first pre-screened for diseased biological entities, and then the diseased biological entities are separated from the normal (healthy or non-diseased) biological entities. The biological subject containing the diseased biological entities separated from the normal biological entities is detected using a desired disease detection method. In FIG. 58(b), a biological sample has gone through multiple, successive cell separation steps to concentrate diseased cells (or biological entities). In FIG. 58(c), after pre-screening to concentrate diseased biological entities, bio-marker is used to detect diseased biological entities. In FIG. 58(d), bio-marker is first used to separate out diseased biological entities and then the sorted out, diseased biological entities are further detected by various detection methods. In short, this process includes initial screening, initial separation, further screening, further separation, probing with one or more disturbing signals or disturbing parameters (e.g., physical, mechanical, chemical, biological, bio-chemical, bio-physical, optical, thermal, acoustical, electrical, electro-mechanical, piezo-electrical, micro-electro-mechanical, or a combination thereof), and finally detection. This sequence can repeat one or more times. The effect of this process is concentrating the diseased entities for improved detection sensitivity and specificity, particularly for a biological subject with a very low concentration of diseased entities, such as circulating tumor cell (CTC).

In FIG. 58(e) through FIG. 58(g), a set of novel processes include (a) pre-screening, pre-separation and initial separation for diseased biological entities, (b) further separation of diseased biological entities, (c) optionally carry out initial detection, and (d) detection using various processes and detection methods. In the pre-separation process, one of the embodiments utilizes nano-particles or nano-magnetic particles attached with bio-markers to sort out diseased biological entities. During pre-separation process, the diseased biological entities are concentrated for higher concentration, which will make further separation and/or following detection easier. The biological sample following pre-separation process can go through further separation process to further enhance the concentration of diseased biological entities. Finally, the biological sample gone through the pre-separation and follow-up separation steps will go through detection step(s), in which various detection techniques and processes can be used to determine diseased biological entities and their types. In some embodiments, multiple detection steps can be utilized to detect diseased biological entities.

FIG. 59(a) shows a cross-sectional view of a channel (5911) into which a biological subject can flow. FIG. 59(b) shows an outside view of the channel, along which an array of detectors (5922) are installed along the path of the flow of the biological subject. Alternatively, both probes and detectors can be installed to both disturb the biological subject to be detected and detect response signals from such disturb signals. FIG. 59(c) shows a cross-section of the wall of the channel, where detectors (5922) are mounted through to contact the biological subject to be detected and also are making contact with the outside world (e.g., to connect to a detection circuitry).

FIG. 60(a) shows a biological subject (6033) to be detected passing through a channel (6011) aligned with detectors (6022) along its passage. The detectors can be the same type of detectors, or a combination of various detectors. Further, probes capable of sending out probing or disturbing signals to the biological subject to be detected can also be implemented along the channels, along with detectors which can detect response from the biological subject which has been probed or disturbed by the probe. The detected signals can be acoustical, electrical, optical (e.g., imaging), biological, bio-chemical, bio-physical, mechanical, bio-mechanical, electro-magnetic, electro-mechanical, electro-chemical-mechanical, electro-chemical-physical, thermal, and thermal-mechanical property related signals, or a combination of them. FIG. 60(b) shows an example of a set of detected signals (e.g., images, pressures, or electrical voltages) (6044) along the path of the biological subject, which recorded its behavior and properties as it passes through the channel. For example, for an optical detector, the size of the circle shown in the FIG. 60(b) could mean the optical emission from the biological subject (such as an optical emission from a florescence component attached to the biological subject), the strength of a strain (pressure) acting on the side wall of the channel detected by a piezo-electric detector or a piezo-photronic detector, or thermal emission from the biological subject detected by a thermal detector or an IR sensor. Such detected signals can be solely from the biological subject as it passes through the channel, or responses from the biological subject to a disturbing or probing signal by the probe.

Like FIG. 60(b), FIG. 60(c) through FIG. 60(e) show additional examples of various detected signal patterns (6044) as the biological subject passes through the channel and is detected by the novel detectors and processes disclosed in the application.

FIG. 61 illustrates a device fabrication process flow and associated device structures. In this process, a first material (6122) is deposited onto a substrate 6111 (see FIG. 61(a)), followed by the formation of an etch mask 6133 which could be a photoresist, a hard mask, or another type of mask (see FIG. 61(c)). The first material is next patterned, with un-masked area of the first material removed (see FIG. 61(d)). Examples of suitable methods for removing the first material include dry etch and wet etch. Following the removal of the mask material (see FIG. 61(e)), a second material (6144) is deposited (see FIG. 61(f)). A portion of the second material is next removed, with the second material above the first material substantially removed and the second material in the recessed area of the first material remaining (see FIG. 61(g)). Examples of suitable methods for removing the second material include etch-back using dry etch and wet etch, and chemical mechanical polishing. A third material 6155 is subsequently deposited (see FIG. 61(h)), and a small opening is patterned (FIG. 61(i)), optionally utilizing lithography and etch processes, or optical ablation processes. Following creating the opening in the third material, the second material is substantially removed (FIG. 61(i)), utilizing methods including but not limited to wet etching, vapor etching, optical processing, and high temperature heating (to evaporate the second material). With these processes, various structures can be formed in the devices, which include but are not limited to channels, probes, detectors, chambers, cavities, and other types of novel and traditional structures and features. FIGS. 61(i) and 61(j) show a cross-sectional view and a top view of a device with micro-channels 6166 and a chamber 6177, respectively.

To enhance the biological subject processing (such as treating, pre-separation, separation, sorting, probing and detecting) capability and throughput, more features and higher number of channels, chambers, probes, detectors, and channels can be fabricated on the same device through building multiple layers of the above disclosed device structures, thereby increasing number of biological entities to be processed and detected. Specifically, the process flow described above can be repeated to build multiple layers. FIG. 61(k) shows a three-layer device with three layers of channels for carrying a biological subject and chambers for various applications such as for pre-separating, separating, probing, and detection biological entities.

Instead of building a large number of layers on the same substrate (for example, over 20 layers), it is sometimes advantageous to build a moderate number of layers and then stack multiple chips each with multiple layers on it into a device with many layers on it (using technologies such as flip chip and other packaging processes). FIG. 61(l) shows two chips (6188 and 6199) with three layers in each chip. In some cases, backside of the chip needs to be thinned before stacking them together. After stacking multiple chips (such as the two chips 6188 and 6199 in FIG. 61(l)) where each chip has multiple layers fabricated using the novel design and processes disclosed in this application, an integrated device with a large number of layers comprising various structures and features (such as chambers or channels for pre-sorting, pre-screening, pre-separation, sorting, screening, separation, probing, and detection), as shown in FIGS. 61(m) and 61(n).

To effectively sorting, separating, screening, probing, or detecting of diseased biological entities, a chamber (or chambers) integrated with various channels can be deployed as shown FIG. 62(a), where incoming sample flowing into a chamber (6211) first. In the chamber, various techniques such as bio-markers and nano-technology (magnetic beads or nano-particles with bio-markers attached to them) based processes can be used to sort out, screen, and separate out the diseased biological entities. For example, a biological sample flowing from the left into the chamber can have its diseased entities separated out in the chamber, and passed downward through the bottom channel, while its normal entities can continue to flow from the chamber in the right hand direction, through the channel in the right side of the chamber. Depending upon the design, the diseased entities, having entered into the chamber on the left, can also be separated out in the chamber, and continue on towards right and flow into the channel on the right side of the chamber, while normal entities will continue to flow down toward and through the channel at the bottom of the chamber. FIG. 62(b) shows multiple chambers integrated with channels in which biological entities can be sorted, screened, separated, probed or detected. In the application of screening and separation, the multiple chambers can carry out multiple screening and separation steps. As shown in FIG. 62(b), for a biological sample flowing from the left toward the right direction, it will enter into the first chamber on the left (6233) and under go a first screening and separation. The biological sample can continue to flow towards the right, enter into the second chamber, the chamber on the right (6244), and undergo a second screening and further separation. In this way, through a multi-staged screening and separation process, the concentration of a diseased entity can be successively enhanced which can be helpful for a sensitive final or late stage detection. This type of device design and process could be very useful for defection of a biological sample with an initially very low concentration of diseased entity population, such as for the detection of circulating tumor cell (CTC) which is typically in the concentration of one part in one billion cells or 10 billion cells.

To significantly speed up the sorting, screening, probing and detection operations using the disclosed device and process, a high number of desired structures such as those discussed in FIG. 63 can be fabricated simultaneously on the same chip as shown in FIG. 63.

FIG. 64 shows another novel device layout for sorting, screening, separating, probing and detecting diseased biological entities, in which a desired component or multiple components through the middle channel into the middle chamber 6411 can play a wide range of roles. For example, the component flowing into the middle chamber could be a bio-marker which can be freshly added into the top chamber 6422 and bottom chamber 6433 when its (bio-marker) concentration needs to be adjusted. The timing, flow rate, and amount of component in the middle chamber 6411 need to be added into the top and bottom chambers (6422 and 6433) can be pre-programmed or controlled via a computer or software in real time. The component into the middle chamber 6412 could also be nano-particles or magnetic beads attached to bio-markers. In another novel embodiment, the component into the middle chamber 6411 could be a disturbing agent which will disturb the biological subject or samples to be detected in the top and bottom chambers.

FIG. 65 shows that, compared with multiple stand alone detection apparatuses (see FIG. 65(*a*), 6511, 6522, 6533, and 6544), an apparatus (6555) with multiple sub-units of different functions and technologies (6566) assembled or integrated has a significantly reduced apparatus volume or size (see FIG. 65(*b*)), therefore reduced costs since many common hardware (e.g., a sample handling unit, a sample measurement unit, a data analysis unit, a display, a printer, etc.) can be shared in an integrated apparatus. For example, such a multi-functional, integrated apparatus can include a bio-marker detector, an imaging based detector, a photo-detector, an x-ray detector, a nuclear magnetic resonance imaging detector, an electrical detector, and an acoustic detector all of which are assembled and integrated into the single apparatus, so that the apparatus can have improved detection functionality, sensitivity, detection versatility, and reduced volume and cost.

FIG. 66 shows that when multiple sub-units with different functions and technologies (2055) are assembled into one apparatus, a more diverse functionality, improved detection functionality, sensitivity, detection versatility, and reduced volume and cost can be achieved, where a number of common utilities including, e.g., input hardware, output hardware, sample handling unit, sample measurement unit, data analysis unit and data display unit (6611, 6633, and 6644) can be shared. For example, when a range of detection units utilizing various detection technologies are assembled into one apparatus, many functions and hardware such as sample handling unit, sample measurement unit, data transmission unit, data analysis unit, computer, and display unit can be shared, thereby significantly reducing the apparatus' equipment volume or size, costs, and complexity while improving measurement functionality and sensitivity.

Tests were carried out in the laboratory with the apparatus of this invention on certain cancerous tissue samples (with multiple samples for each type of cancer) although the apparatus of this invention can be used for detection of other types of cancer or other types of treatment. In the tests, healthy control samples were obtained from animals with no known cancer disease at the time of collection and no history of malignant disease. Both cancerous samples and healthy control samples were collected and cultured in the same type of culture solution. The cultured samples were then mixed with a dilution buffer and diluted to the same concentration. The diluted samples were maintained at the room temperature for different time intervals and processed within a maximum of 6 hours after being recovered. The diluted samples were tested at the room temperature (20~23° C.) and in the humidity of 30%~40%. The samples were tested with an apparatus of this invention under the same conditions and stimulated by the same pulse signal.

The tests show that, in general, the control groups' tested (measured) values (i.e., measured values in relative units for the testing parameter) were lower than the cancerous or diseased groups. Under the same stimulation (in terms of stimulation type and level) with a stimulating or probing signal applied by a probing unit of the tested apparatus of this invention, the difference shown in the measured values between the control groups and the cancerous groups became much more significant, e.g., ranging from 1.5 times to almost 8 times in terms of level of increase in such difference, compared with that without simulation. In other words, the cancerous groups' response to the stimulating signal was much higher than that of the control groups. Thus, the apparatus of this invention have been proven to be able to significantly enhance the relative sensitivity and specificity in the detection and measurement of diseased cells, in comparison to the control or healthy cells.

Further, the test results show that in terms of the novel parameter utilized by the apparatus of this invention, the cancerous group and the control group showed significantly different response. Such difference is significantly greater than the measurement noise. There was a large window to separate the control groups from the cancerous groups, showing a high degree of sensitivity of the novel measurement method and apparatus.

While for the purposes of demonstration and illustration, the above cited novel, detailed examples show how microelectronics and/or nano-fabrication techniques and associated process flows can be utilized to fabricate highly sensitive, multi-functional, powerful, and miniaturized detection devices, the principle and general approaches of employing microelectronics and nano-fabrication technologies in the design and fabrication of high performance detection devices have been contemplated and taught, which can and should be expanded to various combination of fabrication processes including but not limited to thin film deposition, patterning (lithography and etch), planarization (including chemical mechanical polishing), ion implantation, diffusion, cleaning, various materials, combination of processes and steps, and various process sequences and flows. For example, in alternative detection device design and fabrication process flows, the number of materials involved can be fewer than or exceed four materials (which have been utilized in the above example), and the number of process steps can be fewer or more than those demonstrated process sequences, depending on specific needs and performance targets. For example, in some disease detection applications, a fifth material such as a biomaterial-based thin film can be used to coat a metal detection tip to enhance contact between the detection tip and a biological subject being measured, thereby improving measurement sensitivity.

Applications for the detection apparatus and methods of this invention include detection of diseases (e.g., in their early stage), particularly for serious diseases like cancer. Since cancer cell and normal cell differ in a number of ways including differences in possible microscopic properties such as electrical potential, surface charge, density, adhesion, and pH, novel micro-devices disclosed herein are capable of detecting these differences and therefore applicable for enhanced capability to detect diseases (e.g., for cancer), particularly in their early stage. In addition micro-devices for measuring electrical potential and electrical charge parameters, micro-devices capable of carrying out mechanical property measurements (e.g., density) can also be fabricated and used as disclosed herein. In mechanical property measurement for early stage disease detection, the focus will be on the mechanical properties that likely differentiate disease or cancerous cells from normal cell. As an example, one can differentiate cancerous cells from normal cells by using a detection apparatus of this invention that is integrated with micro-devices capable of carrying out micro-indentation measurements.

Although specific embodiments of this invention have been illustrated herein, it will be appreciated by those skilled in the art that any modifications and variations can be made without departing from the spirit of the invention. The examples and illustrations above are not intended to limit the scope of this invention. Any combination of detection apparatus, micro-devices, fabrication processes, and applications of this invention, along with any obvious their extension or analogs, are within the scope of this invention. Further, it is intended that this invention encompass any arrangement, which is calculated to achieve that same purpose, and all such variations and modifications as fall within the scope of the appended claims.

All publications or patent applications referred to above are incorporated herein by reference in their entireties. All the features disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example of a generic series of equivalent or similar features.

Other Embodiments

It is to be understood that while the invention has been described in conjunction with the detailed description thereof and accompanying figures, the foregoing description and accompanying figures are only intended to illustrate, and not limit the scope of the invention, which is defined by the scope of the appended claims. Other aspects, advantages, and modifications are within the scope of the following claims. All publications referenced herein are incorporated by reference in their entireties.

What is claimed is:

1. An apparatus for detecting a disease in a biological subject, comprising a delivery system and at least two sub-equipment units which are combined or integrated in the apparatus, wherein the delivery system configured to deliver the biological subject to at least one of the sub-equipment units and each sub-equipment unit is configured to detect at least one property of the biological subject;
wherein at least one of the sub-equipment units comprises
(a) a first layer of material having an exterior surface and an interior surface, wherein the interior surface defines one or more inter-unit channels in which the biological subject flows through the sub-equipment unit;
(b) a first sorting unit comprising a first sensor, wherein first sorting unit is configured to detect a property of the biological subject at the microscopic level by the first sensor, and sort the biological subject by the detected property;
(c) a first detection unit comprising a second sensor, configured to detect the same or different property of the sorted biological subject at the microscopic level; wherein the first sorting unit and the first detection unit are integrated into the first layer of material and positioned to be at least partially exposed in the inter-unit channel; and
(d) a second sorting unit comprising a third sensor, wherein the biological subject flows by or through the first sorting unit before reaching the second sorting unit, and the second sorting unit is configured to detect by the third sensor the same or different property of the biological subject as the first sorting unit and sorts the biological subject by the property detected by the third sensor,
wherein each of the first and second sorting units sorts the biological subject based on the property detected by its sensor; the biological subject passing through each sorting unit is separated into at least two flows, including one flow that contains a suspected component for further detection or sorting; and the at least two flows continue to flow through different inter-unit channels in different directions;
wherein the sensor in at least one of the first and second sorting units is an electrical sensor; and the at least one of the first and second sorting units detects an electrical property of the biological subject by its electrical sensor, and sorts the biological subject based on the detected electrical property, into at least two separate flows which continue to flow through different inter-unit channels in different directions, wherein one of the inter-unit channels is connected between the first or second sorting unit and an inlet of the first detection unit, and the inlet of the first detection unit is configured to receive the sorted biological subject flowing out of the first or second sorting unit; and wherein the apparatus further comprises a circulating inter-unit channel connected between an outlet of the first detection unit and the first or second sorting unit, and when a valve controlling the circulating inter-unit channel is open, a loop system is formed, allowing the circulating inter-unit channel is configured to transport the biological subject that flows out of the outlet of the first detection unit back to the first or second sorting unit for further sorting and detection of the same or a different property at the microscopic level.

2. The apparatus of claim 1, wherein the sub-equipment further comprises a second detection unit, wherein the biological subject flows by or through the first detection unit before reaching the second detection unit, and the second detection unit is configured to detect the same or different property of the biological subject as the first detection unit.

3. The apparatus of claim 1, wherein a portion of the biological subject flowing through the sorting unit continues to flow to the detection unit, while the rest of the biological subject is directed to another direction for separate disposal.

4. The apparatus of claim 1, wherein each property to be detected by a sub-equipment unit or a detection unit or a sorting unit is independently a thermal, optical, acoustical, biological, chemical, physical-chemical, electro-mechanical, electro-chemical, electro-chemical-mechanical, biophysical, bio-chemical, bio-mechanical, bio-electrical, electro-optical, bio-electro-optical, bio-thermal optical, electro-chemical optical, bio-physical-chemical, bio-electro-physical, bio-electro-mechanical, bio-electro-chemical, bio-chemical-mechanical, bio-electro-physical-chemical, bio-electro-physical-mechanical, bio-electro-chemical-mechanical, electric, magnetic, electro-magnetic, physical, or mechanical property of the biologic subject or cells contained therein.

5. The apparatus of claim 4, wherein the thermal property is temperature or vibrational frequency; the optical property is optical absorption, optical transmission, optical reflection, optical-electrical property, brightness, or fluorescent emission; the radiation property is radiation emission, signal triggered by radioactive material, or information probed by radioactive material; the chemical property is pH value, chemical reaction, bio-chemical reaction, bio-electro-chemical reaction, reaction speed, reaction energy, speed of reaction, oxygen concentration, oxygen consumption rate, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property is density, shape, volume, or surface area; the electrical property is surface charge, surface potential, resting potential, electrical current, electrical field distribution, surface charge distribution, cell electronic properties, cell surface electronic properties, dynamic changes in electronic properties, dynamic changes in cell electronic properties, dynamic changes in cell surface electronic properties, dynamic changes in surface electronic properties, electronic properties of cell membranes, dynamic changes in electronic properties of membrane surface, dynamic changes in electronic properties of cell membranes, electrical dipole, electrical quadruple, oscillation in electrical signal, electrical current, capacitance, three-dimensional electrical or charge cloud distribution, electrical properties at telomere of DNA and chromosome, capacitance, or impedance; the biological property is surface shape, surface area, surface charge, surface biological property, surface chemical property, pH, electrolyte, ionic strength, resistivity, cell concentration, or biological, electrical, physical or chemical property of solution; the acoustic property is frequency, speed of acoustic waves, acoustic frequency and intensity spectrum distribution, acoustic intensity, acoustical absorption, or acoustical resonance; the mechanical property is internal pressure, hardness, flow rate, viscosity, fluid mechanical properties, shear strength, elongation strength, fracture stress, adhesion, mechanical resonance frequency, elasticity, plasticity, or compressibility.

6. The apparatus of claim 1, wherein at least one of the sub-equipment units comprises an additional sensor positioned to be partially in the inter-unit channel of the sub-equipment unit and configured to detect a property of the biological subject at the microscopic level.

7. The apparatus of claim 6, wherein the sorting unit and the detection unit each comprise an additional sensor positioned to be partially in the inter-unit channel and configured to detect a property of the biological subject at the microscopic level, wherein the property to be detected by the sensors in the sorting unit and the detection unit can be the same or different.

8. The apparatus of claim 7, wherein at least one of the sub-equipment units comprises at least one more sensor positioned to be partially in the inter-unit channel of the sub-equipment unit and configured to detect the same or different property of the biological subject at the microscopic level as the first sensor.

9. The apparatus of claim 1, wherein each sensor in the sub-equipment is independently a thermal sensor, optical sensor, acoustical sensor, biological sensor, chemical sensor, electro-mechanical sensor, electro-chemical sensor, electro-optical sensor, electro-thermal sensor, electro-chemical-mechanical sensor, bio-chemical sensor, bio-mechanical sensor, bio-optical sensor, electro-optical sensor, bio-electro-optical sensor, bio-thermal optical sensor, electro-chemical optical sensor, bio-thermal sensor, bio-physical sensor, bio-electro-mechanical sensor, bio-electro-chemical sensor, bio-electro-optical sensor, bio-electro-thermal sensor, bio-mechanical-optical sensor, bio-mechanical thermal sensor, bio-thermal-optical sensor, bio-electro-chemical-optical sensor, bio-electro-mechanical optical sensor, bio-electro-thermal-optical sensor, bio-electro-chemical-mechanical sensor, physical sensor, mechanical sensor, piezo-electrical sensor, piezo-electro photronic sensor, piezo-photronic sensor, piezo-electro optical sensor, bio-electrical sensor, bio-marker sensor, electrical sensor, magnetic sensor, electro-magnetic sensor, image sensor, or radiation sensor.

10. The apparatus of claim 9, wherein the thermal sensor comprises a resistive temperature micro-sensor, a micro-thermocouple, a thermo-diode and thermo-transistor, and a surface acoustic wave (SAW) temperature sensor; the image sensor comprises a charge coupled device (CCD) or a CMOS image sensor (CIS); the radiation sensor comprises a photoconductive device, a photovoltaic device, a pyro-electrical device, or a micro-antenna; the mechanical sensor comprises a pressure micro-sensor, micro-accelerometer, flow meter, viscosity measurement tool, micro-gyrometer, or micro flow-sensor; the magnetic sensor comprises a magneto-galvanic micro-sensor, a magneto-resistive sensor, a magneto diode, or magneto-transistor; the biochemical sensor comprises a conductimetric device, a bio-marker, a bio-marker attached to a probe structure, or a potentiometric device.

11. The apparatus of claim 1, wherein the sensors in the device include at least one probing sensor that can apply a probing or disturbing signal to the biological subject.

12. The apparatus of claim 11, wherein the sensors in the device include at least another sensor, different from the probing sensor, being a detection sensor that detects a response from the biological subject upon which the probing or disturbing signal is applied.

13. The apparatus of claim 1, wherein the sorting unit or the detection unit comprise two panels, at least one of the two panels is fabricated by microelectronic technologies and comprises a read-out circuitry and a sensor, and the sensor is positioned on the interior surface which defines the inter-unit channel.

14. The apparatus of claim 13, wherein the sorting unit or the detection unit further comprises two micro-cylinders that are placed between and bonded with the two panels, wherein each of the micro-cylinders is solid, hollow, or porous, and optionally fabricated by microelectronics technologies.

15. The apparatus of claim 13, wherein the micro-cylinders are solid and at least one of them comprises a sensor fabricated by microelectronics technologies.

16. The apparatus of claim 13, wherein the sensor in the micro-cylinder applies a probing signal to the biological subject.

17. The apparatus of claim 13, wherein at least one of the micro-cylinders comprises at least two sensors fabricated by microelectronics technologies, and every two of the at least two sensors are so located in the micro-cylinder to form an array of the sensors on the panel.

18. The apparatus of claim 17, wherein the two sensors in the micro-cylinder are apart by a distance ranging from 0.1 micron to 500 microns, from 0.1 micron to 50 microns, form 1 micron to 100 microns, from 2.5 microns to 100 microns, or from 5 microns to 250 microns.

19. The apparatus of claim 18, wherein at least one of the panels comprises at least two sensors that are arranged in at least two arrays each separated by at least a micro sensor in a cylinder.

20. The apparatus of claim 1, wherein the interior surface defines at least one additional inter-unit channel for transporting and sorting or detecting the biological subject.

21. The apparatus of claim 20, wherein at least one of the sub-equipment units has numerous inter-unit channels for transporting and sorting or detecting the biological subject.

22. The apparatus of claim 1, wherein the inter-unit channel has a diameter or height or width ranging from 0.1 micron to 150 microns, from 0.5 micron to 5 microns, from 1 micron to 2.5 microns, from 3 microns to 15 microns, from 5 microns to 25 microns, from 5 microns to 50 microns, from 25 microns to 50 microns, or from 50 microns to 80 microns; and the inter-unit channel has a length ranging from 0.5 micron to 50,000 microns.

23. The apparatus of claim 1, wherein the sub-equipment unit or the sorting unit or the detection unit comprises and is capable of releasing a bio-marker, an enzyme, a protein, a light emitting component, an radio-active material, a dye, a polymer component, an organic component, a catalyst, an oxidant, a reducing agent, an ionic component, a nano-particle, a magnetic particle, or a nano-particle attached to a bio-marker, or a combination thereof, for mixing with and sorting or detecting the biological subject.

24. The apparatus of claim 23, wherein the nano-particle attached to a bio-marker is a magnetic nano-particle; and one or more magnetic nano-particles are mixed with the biological subject for separating and detecting the biological subject.

25. The apparatus of claim 23, wherein the bio-marker is attached with a light emitting item and mixed with the biological subject.

26. The apparatus of claim 25, wherein the light emitting item is a florescence generating component.

27. The apparatus of claim 26, wherein the mixed biological subject flows through an inter-unit channel; a signal of the mixed biological subject is detected and collected by a sensor in a sorting or detection unit; and the signal is an electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical or mechanical signal, or a combination thereof.

28. The apparatus of claim 1, wherein the biological subject flows through the first inter-unit channel and, after the sorting unit, is separated into the suspected component and an unsuspected component, and the two components continue to flow through the inter-unit channel in two different directions.

29. The apparatus of claim 28, wherein the sub-equipment unit further comprises one or more additional inter-unit channels each of which is defined by the interior surface of the first or additional layer of material and is integrated to the first channel, and the separated suspected component or unsuspected component flows through the additional channel(s) for further separation.

30. The apparatus of claim 28, wherein the sub-equipment unit comprises multiple sorting inter-unit channels arranged in a parallel manner, configured to divide the biological subject into multiple divided flows, wherein each sorting inter-unit channel includes one or more sorting units positioned to be at least partially exposed in the sorting inter-unit channel, wherein the divided flows simultaneously flow through the respective sorting inter-unit channels, and the divided flows are simultaneously sorted and separated in the respective sorting inter-unit channels.

31. The apparatus of claim 30, wherein the first inter-unit channel is centrally positioned in the sub-equipment unit as compared to the other additional inter-unit channels and is connected to at least two other inter-unit channels; and a designed component injected into the first inter-unit channel flows from this first inter-unit channel to the other connected inter-unit channels.

32. The apparatus of claim 31, wherein the designed component is a bio-marker, a nano-particle, a magnetic particle, an enzyme, a protein, a light emitting component, an radio-active material, a dye, a polymer component, an organic component, a catalyst, an oxidant, a reducing agent, an ionic component, or a nano-particle attached to a bio-marker, a disturbing fluid, or a combination thereof.

33. The apparatus of claim 1, wherein the sub-equipment unit further comprising a probing unit which is configured to apply a probing signal to the biological subject or a media in which the biological subject is contained, thereby changing the nature or value of a property of the biological subject or of the media.

34. The apparatus of claim 33, wherein the probing signal or the property to be detected is independently a thermal, optical, acoustical, biological, chemical, electro-mechanical, electro-chemical, electro-chemical optical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, electrical, magnetic, electromagnetic, physical or mechanical property, or a combination thereof.

35. The apparatus of claim 1, wherein the sub-equipment unit further comprises a pre-screening unit which is configured to pre-screen a diseased biological subject from a non-diseased biological subject based on the difference in a property between a diseased biological subject and a non-diseased biological subject.

36. The apparatus of claim 1, wherein the delivery system comprises a layer of material having an interior surface, wherein the interior surface defines an intra-unit channel in which the biological subject flows to the inter-unit channel or inter-unit channels of one or more desired sub-equipment units.

37. The apparatus of claim 1, further comprising a central control unit that is connected to each sub-equipment unit, and capable of controlling the biological subject to be transported to and detected by one or more desired sub-equipment units, and reading and analyzing the detected data from each sub-equipment unit.

38. The apparatus of claim 37, wherein the central control unit further comprises a controlling circuitry, an addressing unit, an amplifier circuitry, a logic processing circuitry, an analog device, a memory unit, an application specific chip, a signal transmitter, a signal receiver, or a sensor.

39. The apparatus of claim 38, wherein the central control unit comprises a pre-amplifier, a lock-in amplifier, an electrical meter, a thermal meter, a switching matrix, a system bus, a nonvolatile storage device, or a random access memory.

40. The apparatus of claim 38, wherein the sensor comprises a thermal sensor, a flow meter, an optical sensor, an acoustic detector, a current meter, an electrical sensor, a pH meter, a hardness measurement sensor, an imaging device, a camera, a piezo-electrical sensor, a piezo-photronic sensor, a piezo-electro photronic sensor, an electro-optical sensor, an electro-thermal sensor, a bio-electrical sensor, a bio-marker sensor, a bio-chemical sensor, a chemical sensor, an ion emission sensor, a photo-detector, an x-ray sensor, a radiation material sensor, an electrical sensor, a magnetic sensor, an electro-magnetic sensor, a voltage meter, a thermal sensor, a flow meter, or a piezo-meter.

41. The apparatus of claim 37, further comprising a system for distributing the biological subject, a distribution channel, a pre-processing unit, a re-charging unit, a detection device, a global positioning system, a motion device, a signal transmitter, a signal receiver, a sensor, a memory storage unit, a logic processing unit, an application specific chip, a unit for recycling and reclaiming the biological subject, a micro-electro-mechanical device, a multi-functional device, or a micro-instrument to perform surgery, drug delivery, cleaning, or medical function.

42. The apparatus of claim 1, wherein the layer of that defines the inter-unit or intra-unit channel comprises a biocompatible material on its interior surface.

43. The apparatus of claim 42, wherein the biocompatible material is a synthetic polymeric material, phosphate based material, carbone based material, carbone oxide based material, carbone oxynitride based material, or naturally occurring biological material.

44. The apparatus of claim 1, wherein the disease is a cancer.

45. The apparatus of claim 44, wherein the cancer is breast cancer, lung cancer, esophageal cancer, intestine cancer, cancer related to blood, liver cancer, stomach cancer, cervical cancer, ovarian cancer, rectum cancer, or circulating tumor cells.

46. The apparatus of claim 1, wherein the sub-equipment unit or the sorting unit or the detection unit further comprises an optical device, imaging device, camera, viewing station, acoustic detector, piezo-electrical detector, piezo-photronic detector, piezo-electro photronic detector, electro-optical detector, electro-thermal detector, electrical detector, bio-electrical detector, bio-marker detector, bio-chemical detector, chemical sensor, thermal detector, ion emission detector, photo-detector, x-ray detector, radiation material detector, electrical detector, or thermal recorder, each of which is integrated into the a panel or a micro cylinder.

* * * * *